(12) United States Patent
Breinlinger et al.

(10) Patent No.: US 9,744,533 B2
(45) Date of Patent: Aug. 29, 2017

(54) MOVEMENT AND SELECTION OF MICRO-OBJECTS IN A MICROFLUIDIC APPARATUS

(71) Applicant: Berkeley Lights, Inc., Emeryville, CA (US)

(72) Inventors: Keith J. Breinlinger, San Rafael, CA (US); Eric D. Hobbs, Livemore, CA (US); Daniele Malleo, El Cerrito, CA (US); J. Tanner Nevill, El Cerrito, CA (US); Mark P. White, San Francisco, CA (US)

(73) Assignee: Berkeley Lights, Inc., Emeryville, CA (US)

( * ) Notice: Subject to any disclaimer, the term of this patent is extended or adjusted under 35 U.S.C. 154(b) by 0 days.

(21) Appl. No.: 14/965,721

(22) Filed: Dec. 10, 2015

(65) Prior Publication Data

US 2016/0199837 A1 Jul. 14, 2016

Related U.S. Application Data

(60) Provisional application No. 62/090,303, filed on Dec. 10, 2014.

(51) Int. Cl.
*B01L 3/00* (2006.01)
*G01N 1/40* (2006.01)

(52) U.S. Cl.
CPC ..... *B01L 3/502761* (2013.01); *B01L 3/50273* (2013.01); *B01L 3/502715* (2013.01); *G01N 1/4077* (2013.01); *B01L 2200/0668* (2013.01); *B01L 2300/0816* (2013.01); *B01L 2300/0819* (2013.01); *B01L 2300/0848* (2013.01); *B01L 2300/0877* (2013.01); *B01L 2400/0424* (2013.01); *B01L 2400/0427* (2013.01); *B01L 2400/0454* (2013.01); *B01L 2400/0457* (2013.01); *B01L 2400/086* (2013.01); *G01N 2001/4083* (2013.01)

(58) Field of Classification Search
CPC .................................... B01L 3/00; G01N 1/40
USPC .................. 422/502; 435/308.1; 436/63, 165
See application file for complete search history.

(56) References Cited

U.S. PATENT DOCUMENTS

| | | |
|---|---|---|
| 6,294,063 B1 | 9/2001 | Becker et al. |
| 6,942,776 B2 | 9/2005 | Medoro |
| (Continued) | | |

FOREIGN PATENT DOCUMENTS

WO 2013185125 A1 6/2013

OTHER PUBLICATIONS

Yi, Amalytica Chimica Acta 560;1-23 (2006).
(Continued)

*Primary Examiner* — Arlen Soderquist
(74) *Attorney, Agent, or Firm* — Kenneth E. Horton; Kirton McConkie

(57) ABSTRACT

A microfluidic apparatus is provided having one or more sequestration pens configured to isolate one or more target micro-objects by changing the orientation of the microfluidic apparatus with respect to a globally active force, such as gravity. Methods of selectively directing the movements of micro-objects in such a microfluidic apparatus using gravitational forces are also provided. The micro-objects can be biological micro-objects, such as cells, or inanimate micro-objects, such as beads.

33 Claims, 26 Drawing Sheets

(56) References Cited

U.S. PATENT DOCUMENTS

| | | | |
|---|---|---|---|
| 7,442,339 B2* | 10/2008 | Sundararajan | C12Q 1/6827 356/301 |
| 2003/0224528 A1 | 12/2003 | Chiou et al. | |
| 2004/0072278 A1 | 4/2004 | Chou et al. | |
| 2004/0229349 A1* | 11/2004 | Daridon | G02B 21/32 435/305.2 |
| 2005/0175981 A1 | 8/2005 | Voldman et al. | |
| 2006/0078888 A1* | 4/2006 | Griffiths | B01F 3/0807 435/6.11 |
| 2006/0099705 A1* | 5/2006 | Wikswo | B01L 3/5027 435/288.5 |
| 2007/0095669 A1 | 5/2007 | Lau et al. | |
| 2008/0085556 A1 | 4/2008 | Graefing et al. | |
| 2008/0223721 A1* | 9/2008 | Cohen | B01L 3/5025 204/451 |
| 2009/0005254 A1* | 1/2009 | Griffiths | B01F 5/0646 506/7 |
| 2009/0170186 A1 | 7/2009 | Wu et al. | |
| 2010/0003666 A1 | 1/2010 | Lee et al. | |
| 2010/0101960 A1 | 4/2010 | Ohta et al. | |
| 2010/0219076 A1 | 9/2010 | Yamakawa et al. | |
| 2010/0263599 A1* | 10/2010 | Yanik | A61K 49/0008 119/216 |
| 2011/0117634 A1 | 5/2011 | Halamish et al. | |
| 2011/0262906 A1 | 10/2011 | Dimov et al. | |
| 2012/0122084 A1* | 5/2012 | Wagner | C12N 5/0612 435/6.1 |
| 2012/0156675 A1 | 6/2012 | Lueerssen et al. | |
| 2013/0086980 A1 | 4/2013 | Gadini et al. | |
| 2013/0118905 A1 | 5/2013 | Morimoto et al. | |
| 2013/0171628 A1* | 7/2013 | Di Carlo | B01L 3/502746 435/6.1 |
| 2013/0190212 A1* | 7/2013 | Handique | B01L 3/502715 506/37 |
| 2013/0204076 A1 | 8/2013 | Han et al. | |
| 2014/0116881 A1* | 5/2014 | Chapman | B01L 3/502761 204/451 |
| 2014/0212881 A1* | 7/2014 | Handique | C12Q 1/686 435/6.12 |
| 2014/0248621 A1* | 9/2014 | Collins | G01N 15/1031 435/6.12 |
| 2015/0079676 A1* | 3/2015 | Wright | A61D 19/02 435/366 |
| 2015/0151298 A1* | 6/2015 | Hobbs | B01L 3/502761 435/7.1 |
| 2015/0306598 A1* | 10/2015 | Khandros | B03C 5/026 204/547 |
| 2015/0306599 A1* | 10/2015 | Khandros | B03C 5/026 204/547 |
| 2015/0352547 A1* | 12/2015 | Breinlinger | C12M 23/16 435/395 |
| 2015/0375228 A1* | 12/2015 | Sohn | G01N 15/0272 435/30 |
| 2016/0158748 A1* | 6/2016 | Wu | B01L 3/502715 422/504 |
| 2016/0158757 A1* | 6/2016 | Breinlinger | B01L 3/502761 422/504 |
| 2016/0160259 A1* | 6/2016 | Du | B01L 3/502792 702/19 |
| 2016/0171686 A1* | 6/2016 | Du | G01N 15/1434 382/130 |
| 2016/0257918 A1* | 9/2016 | Chapman | C12M 21/06 |
| 2016/0312165 A1* | 10/2016 | Lowe, Jr. | C12M 29/10 |
| 2016/0370266 A1* | 12/2016 | White | G01N 1/34 |

OTHER PUBLICATIONS

Di Carlo, Analytical Chemistry, 7918-25 (2006).

Ku, Guolin et al., Recent Trends in Dielectrophoresis, Informacije MIDEM, 2010, vol. 40, Issue No. 4, pp. 253-262.

Chung et al., Imaging Single-cell Signaling Dynamics with a Deterministic High-Density Single-Cell Trap Array, Anal. Chem. 83 (18):7044-7052 (2011).

Chen et al., Microfluidic Approaches for Cancer Cell Detection, Characterization, and Separation, Lab on a Chip 12:173 (2012).

European Patent Office, International Search Report and Written Opinion for PCT Application Serial No. PCT/US2015/065085 (Jun. 13, 2016), 25 pages.

* cited by examiner

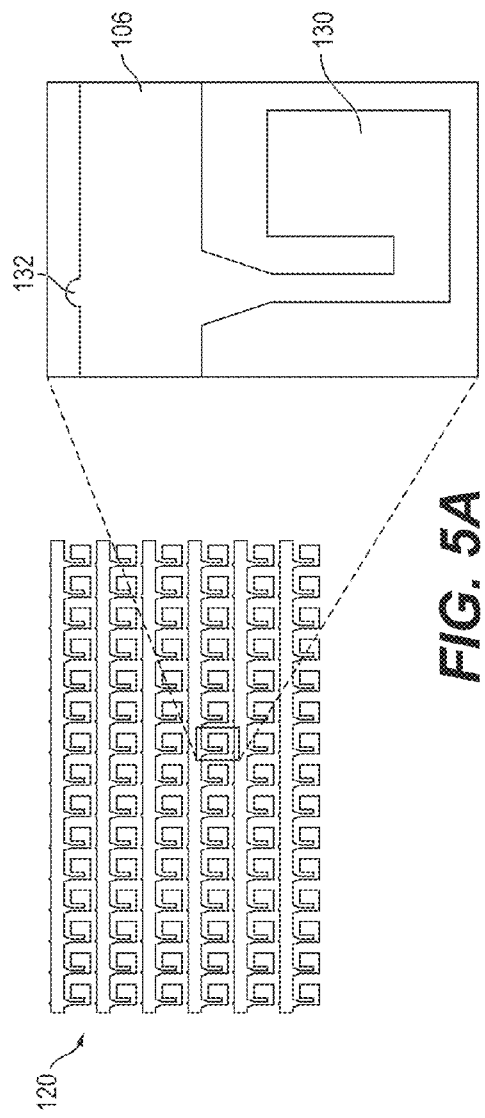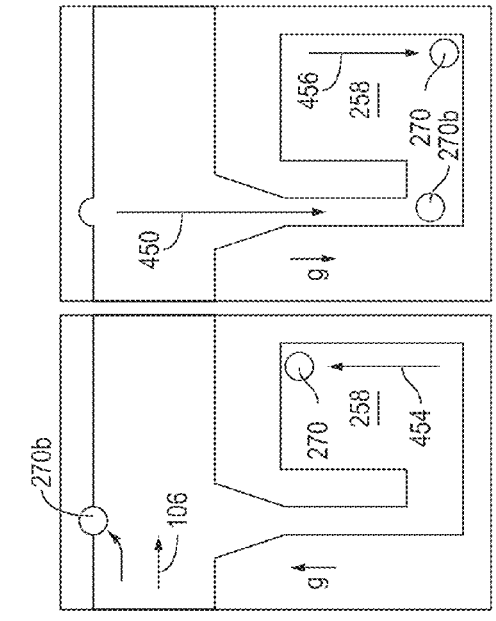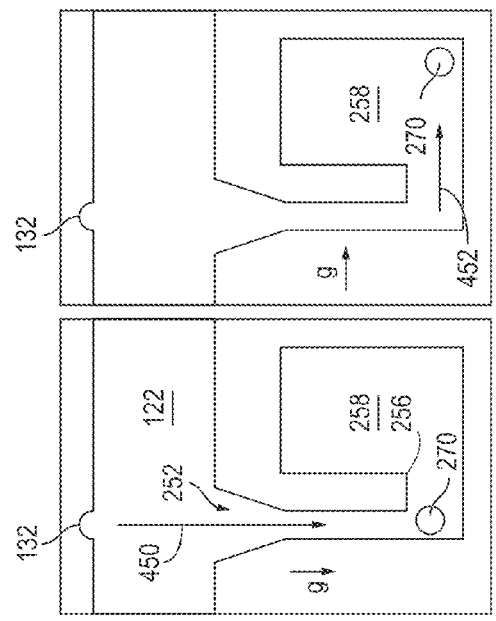

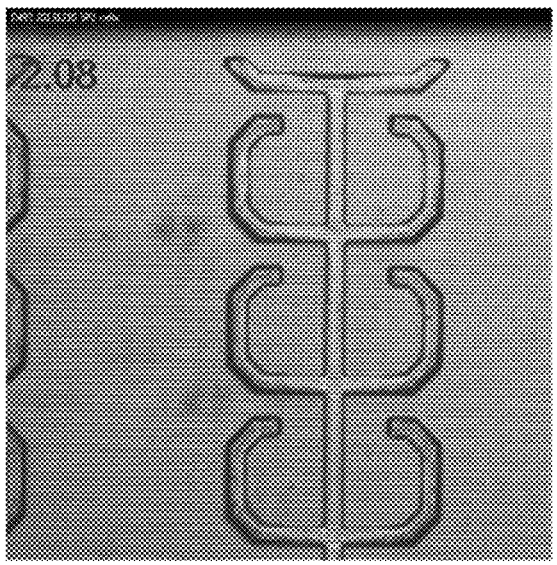 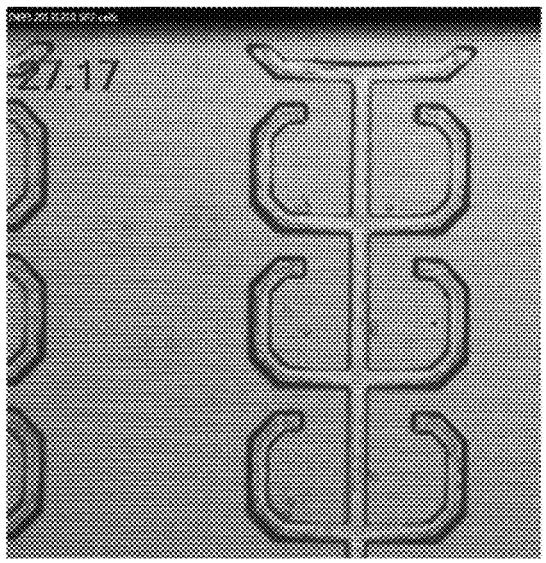
FIG. 17A  FIG. 17B
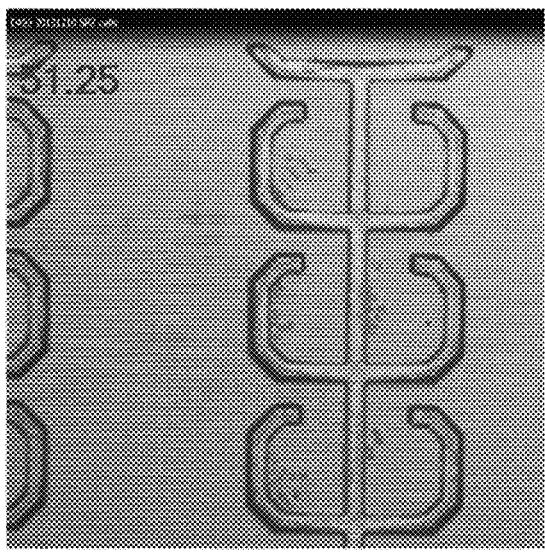 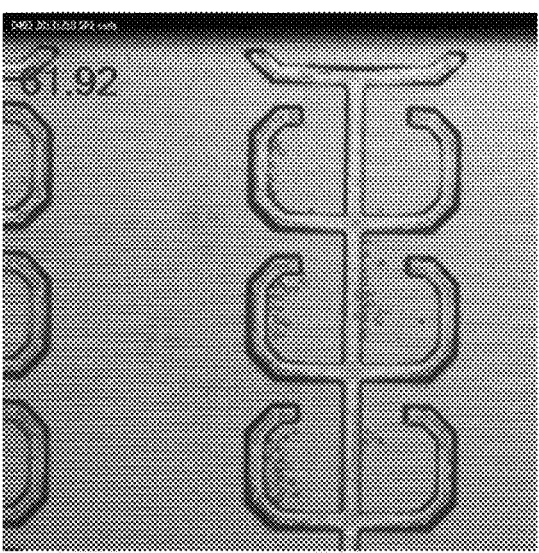
FIG. 17C  FIG. 17D

MOVEMENT AND SELECTION OF MICRO-OBJECTS IN A MICROFLUIDIC APPARATUS

CROSS REFERENCE TO RELATED APPLICATION(S)

This application is a non-provisional of, and thus claims the benefit of and/or priority to, U.S. provisional patent application Ser. No. 62/090,303, filed on Dec. 10, 2014, the entire contents of which are incorporated herein by reference.

FIELD OF THE INVENTION

The present invention generally relates to microfluidic devices designed to make use of globally active forces, such as gravity. In particular, the microfluidic devices and related methods allow for the selective manipulation of micro-objects through changes in the position of the devices relative to the orientation of globally active forces.

BACKGROUND OF THE INVENTION

As the field of microfluidics continues to progress, microfluidic devices have become convenient platforms for processing and manipulating micro-objects such as biological cells. Some embodiments of the present invention are directed to improvements in microfluidic devices and methods of operating microfluidic devices in which the spatial orientation of a microfluidic device is manipulated to select, collect, isolate, and/or retain desired micro-objects within a microfluidic device. Some embodiments of the present invention utilize gravitational force, alone or in combination with dielectrophoretic (DEP) or optoelectronic tweezer (OET) forces, to accomplish such selection, collection, isolation, and/or retention.

SUMMARY

The invention provides, in some embodiments, a microfluidic device (e.g. having a microfluidic circuit) that includes a flow region, such as a microfluidic channel, and one or more microfluidic sequestration pens having various features for using a globally active force, such as gravity, to collect and retain micro-objects. The flow region and sequestration pens can be configured to contain a fluidic medium. The flow region, which can be a microchannel, can further include one or more micro-object traps which are configured to collect micro-objects from fluidic medium as it flows by and then release the collected micro-objects such that they can settle into a sequestration pen when the microfluidic device is tilted.

In some embodiments, a system comprising a tilting device is provided for use with the microfluidic device. The tilting device can be configured to manipulate the microfluidic device between horizontal and vertical orientations. The tilting device can be configured to rotate the microfluidic device about one or more axes, such as an x-axis and/or a y-axis. Thus, the tilting device can manipulate the microfluidic device's angle of incline so as to spatially reposition or relocate elements within the microfluidic device relative to the gravitational force vector operating on the microfluidic device.

In some embodiments, methods for selecting and capturing a target micro-object are provided. The methods can include repositioning the microfluidic device one or more times such that a target micro-object moves along a pre-selected path within the microfluidic device. The methods can also include selecting a single target micro-object, moving the selected micro-object away from other micro-objects, and/or isolating the selected micro-object in an isolation region of a sequestration pen in the microfluidic device. The other micro-objects initially located alongside the selected micro-object can be moved to a separate region of the microfluidic device, such as the flow region (e.g., a channel).

In some embodiments, the microfluidic sequestration pens of the microfluidic device can have a nautilus-like shape, a boot-like shape, or a funnel-like shape. The microfluidic sequestration pens can have at least one opening which includes a constriction to prevent passage of more than one target micro-object at a time. The microfluidic sequestration pens can include a primary isolation region and a secondary isolation region, wherein only a portion of the primary isolation region is in fluid communication with the secondary isolation region. The secondary isolation region can be in a different plane of the microfluidic device than the first isolation region.

In some embodiments, the microfluidic device can include an enclosure and a plurality of electrodes for implementing electrokinetic forces within the enclosure. The enclosure can contain the flow region and the one or more sequestration pens, and conductors, such as transistors or electrodes, for implementing the electrokinetic forces can be present in the flow region and/or one or more of the sequestration pens. The electrokinetic forces can include dielectrophoretic (DEP) forces, such as produced by optoelectronic tweezers (OET). The electrokinetic forces can be used in conjunction with gravitational force to manipulate a position of one or more micro-objects.

Accordingly, in one aspect, the invention provides a microfluidic device having an enclosure which includes: a flow path configured to contain a flow of a fluidic medium; and a microfluidic sequestration pen comprising an isolation region and a connection region fluidically connecting the isolation region to the flow path, wherein, when the microfluidic device is tilted such that the flow path is located below the sequestration pen, target micro-objects located in the isolation region are retained in the isolation region, while target micro-objects located in the connection region settle into the flow path. The sequestration pens can be shaped, for example, like a boot or a nautilus.

In certain embodiments, the connection region of the sequestration pens can include an opening to the isolation region that has a width that is smaller than five times (e.g., smaller than four times, three times, two times, etc.) the diameter of a target micro-object. For example, the opening of the connection region to the isolation region can have a width of about 20 microns to about 100 microns (e.g., about 20 microns to about 50 microns). In certain embodiments, the connection region can include a beveled or a chamfered opening (e.g., a beveled or chamfered proximal opening).

In certain embodiments, the isolation region can include an opening that interfaces with the connection region, wherein there is an obstruction or a constriction located at the interface. The obstruction or constriction can have a width that is smaller than five times (e.g., smaller than four times, three times, two times, etc.) the diameter of a target micro-object. For example, obstruction or constriction can have a width that is about 20 microns to about 100 microns (e.g., about 20 microns to about 50 microns).

In certain embodiments, the isolation region (or a distal end thereof) can have a volume configured to receive a single target micro-object. The isolation region (or distal end thereof) can have a length equivalent to at least about 1.5 diameters (e.g., about 2, 2.5, 3, 4, 5, or more diameters) of a target micro-object. For example, the isolation region can have a length of at least about 10 microns (e.g., at least about 15, 20, 25, 30, 35, 40, 45, 50 microns). The isolation region (or the distal end thereof) can have a volume of about 10,000 $\mu m^3$ to about 20,000 $\mu m^3$, or about 20,000 $\mu m^3$ to about 100,000 $\mu m^3$.

In certain embodiments, the sequestration pen can include a plurality of isolation regions. Each isolation region can extend laterally from the connection region. Alternatively, one isolation region of the plurality can extend distally from a distal end of the connection region, and the other isolation region(s) of the plurality can extend laterally from a side (e.g., a single common side) of the connection region. The openings to each isolation region of the plurality can have substantially the same width or cross-sectional area. Alternatively, the opening to at least one isolation region of the plurality can have a width or cross-sectional area that is smaller than the width or cross-sectional area of the openings to the other isolation regions of the plurality. The isolation regions of the plurality can have substantially the same volume. Alternatively, one isolation region of the plurality can have a volume that is smaller or larger than the volumes of the other isolation regions of the plurality. Each isolation region of the plurality (or each distal end of each isolation region of the plurality) can have a volume configured to receive a single target micro-object.

The microfluidic device can comprise a plurality of sequestration pens, each having a corresponding isolation region and a corresponding connection region fluidically connecting the corresponding isolation region to the flow path. The sequestration pens can have any of the configurations described herein. Each of the sequestration pens of the plurality can open off of a common flow path.

In some embodiments, the sequestration pen can include a secondary isolation region fluidically connected with a first (or primary) isolation region. The secondary isolation region can be connected to the primary isolation region such that, upon tilting the microfluidic device, a micro-object located within the primary isolation region is able to settle into the secondary isolation region. The tilting of the microfluidic device can include turning the microfluidic device upside down or otherwise inverting the microfluidic device. The secondary isolation chamber can be located proximate to and in fluid communication with a plurality of isolation regions. The plurality of isolation regions can be located in the same sequestration pen or different sequestration pens (e.g., adjacent sequestration pens).

In certain embodiments, the flow path of the microfluidic device is a channel. The flow path (or channel) can include, for example, a trap designed to capture micro-objects as they flow through the channel. The trap can be formed in a wall of the channel (e.g., opposite an opening to a sequestration pen) or can be formed in a structure located within the flow path. The trap can have a volume approximately equal to at least the volume of a single target micro-object, and can include an opening having a width that is approximately equal to or greater than the diameter of a target micro-object. The trap can also include a side passage having a diameter that is less than the diameter of a target micro-object. The microfluidic device can include a plurality of traps. Each such trap can be formed in the wall of a channel (e.g., opposite an opening to a sequestration pen) or in a structure (e.g., a column) disposed within the flow path.

In certain embodiments, a sequestration pen can include an isolation region and a plurality of connection regions, each connection region fluidically connecting the isolation region to the flow path. Each connection region of the plurality can include a proximal opening to the flow path having a width (or cross-sectional area) sufficient to receive a target micro-object. The widths (or cross-sectional areas) of the proximal openings of the connection regions can be as described herein, and can be of substantially equal in size. Alternatively, the widths (or cross-sectional areas) of the proximal openings of the connection regions can be substantially non-equal in size.

In certain embodiments, the microfluidic device can further include a support structure and a microfluidic structure. The support structure and the microfluidic structure can together define the enclosure. In addition, the support structure and/or the microfluidic structure can be configured to support the generation of an electrokinetic force within at least a portion of the enclosure (e.g., in one or more sequestration pens and/or the flow path). The support structure can include an electrode connected to an array of transistors. The transistors of the array can be, for example, phototransistors. The microfluidic structure can include walls and a cover. The cover can be transparent and can include an electrode.

In certain embodiments, a surface of the sequestration pen can include a functional moiety. The functional moiety can specifically bind to target micro-objects. The target micro-objects can be, for example, biological cells. The functional moiety can include a polymer, a carbohydrate, an antibody, an extracellular matrix component or derivative thereof, or any combination thereof.

In another aspect, the invention provides methods for loading a target micro-object into a microfluidic sequestration pen. The methods can include: flowing a fluidic medium containing target micro-objects into a flow path of a microfluidic device; repositioning (or tilting) the microfluidic device from a starting position (e.g., a level position) to a first loading position such that a first portion of fluidic medium in the flow path is located above an opening of a sequestration pen; and allowing gravity to act on the target micro-objects located in the first portion of fluidic medium, for an amount of time sufficient for any target micro-objects therein to settle into the sequestration pen. The method can include slowing or substantially stopping the flow of fluidic medium through the flow path (e.g., prior to positioning the microfluidic device into the first loading position).

In certain embodiments, repositioning the microfluidic device into the first loading position involves tilting the microfluidic device along an axis parallel to an axis of the flow path. The sequestration pen can include an isolation region and a connection region configured such that target micro-objects that settled into said sequestration pen collect (e.g., primarily or exclusively) in the connection region.

In certain embodiments, the method includes: optionally repositioning the microfluidic device; and moving one or more target micro-objects located in the connection region into the isolation region. The repositioning can involve returning the microfluidic device to a level (or starting) position. Moving the one or more target micro-objects into the isolation region can involve: detecting the one or more target micro-objects located in the connection region; selecting a single target micro-object from the one or more target micro-objects; moving the selected target micro-object from the connection region into the isolation region; and moving any micro-objects remaining in the connection region back into the flow path. The selected target micro-object can be selected manually or automatically, and can be moved using electrokinetic force (e.g., dielectrophoresis (DEP) and/or optoelectronic tweezers (OET)).

In other embodiments, moving the one or more target micro-objects into the isolation region can include: repositioning the microfluidic device into a second loading position such that a first portion of the connection region is located above an opening from the isolation region to the connection region; and allowing gravity to act on target micro-objects located in the first portion of the connection region for an amount of time sufficient for any target micro-objects in the first portion of the connection region to settle into the isolation region. In certain related embodiments, repositioning the microfluidic device into the second loading position involves tilting the microfluidic device along an axis substantially perpendicular to an axis defined by the opening from the isolation region to the connection region. For example, the axis can be substantially perpendicular (or normal) to a plane that defines the opening between the isolation region and the connection region. In other related embodiments, repositioning the microfluidic device into the second loading position comprises tilting the microfluidic device along an axis substantially perpendicular to the axis of the flow path. In still other related embodiments, repositioning the microfluidic device into the second loading position comprises tilting the microfluidic device along an axis substantially perpendicular to the support structure of the microfluidic device. In certain embodiments, the methods further include: detecting one or more target micro-objects located in the isolation region; selecting a single target micro-object from the one or more target micro-objects; moving any micro-objects other than the selected micro-object out of the isolation region and back into the connection region; and moving any target micro-objects returned to the connection region back into the flow path. The selected micro-object can be selected manually or automatically, and moving unselected micro-objects back into the connection region can be accomplished using electrokinetic force (e.g., dielectrophoresis (DEP) and/or optoelectronic tweezers (OET)).

In certain embodiments, moving any micro-objects remaining in the connection region back into the flow path can include: positioning the microfluidic device into an unloading position, such that the first portion of fluidic medium in the flow path is located beneath the opening of the sequestration pen to the flow path; and allowing gravity to act on any micro-objects remaining in the connection region for an amount of time sufficient for the remaining micro-objects to settle into the first portion of fluidic medium in the flow path.

In certain embodiments, the microfluidic device includes a plurality of sequestration pens, and the plurality of sequestration pens are loaded with target micro-objects in parallel. The fluidic medium containing target micro-objects (e.g., in the flow region at the beginning of the methods) can contain about $1.0 \times 10^6$ micro-objects/mL to about $5.0 \times 10^7$ micro-objects/mL. The fluidic medium containing target micro-objects can have a target micro-object density such that at least about 13% (or at least about 35%) of the sequestration pens in the microfluidic device lack a target micro-object after allowing gravity to act on the target micro-objects for an amount of time sufficient for any target micro-objects located in the first portion of said flow path to settle into the sequestration pen. Alternatively, the fluidic medium containing target micro-objects can have a target micro-object density such that less than about 35% (or less than about 13%) of the sequestration pens in the microfluidic device lack a target micro-object after allowing gravity to act on the target micro-objects for an amount of time sufficient for any target micro-objects located in the first portion of said flow path to settle into the sequestration pen. In certain embodiments, the method is repeated at least once so as to achieve super-Poisson loading of the sequestration pens.

In any of the foregoing methods, the micro-objects can be magnetic beads. In such embodiments, a magnet can be used to induce micro-object movements rather than repositioning the microfluidic device. For example, the magnet can be moved relative to the microfluidic device such that the magnet pulls on the magnetic micro-particles in the same direction as gravity would have pulled on the micro-particles if the microfluidic device was repositioned.

In another aspect, the invention provides a method for loading target micro-objects into a microfluidic sequestration pen including the steps of: flowing a fluidic medium containing target micro-objects into a flow path of a microfluidic device; substantially stopping the flow of fluidic medium; and applying centrifugal force to the microfluidic device and any target micro-objects contained therein for an amount of time sufficient for any target micro-objects located in the flow path (e.g., a first portion thereof) to settle into a sequestration pen that opens off of the flow path.

In another aspect, the invention provides methods for achieving a substantially uniform micro-object density in a flow path of a microfluidic device. The methods can include: flowing a first fluidic medium containing micro-objects into a flow path of the microfluidic device; positioning the microfluidic device into a loading position such that the flow path is located above the openings of a plurality of pens; allowing gravity to act on the micro-objects in the first fluidic medium for an amount of time sufficient for the micro-objects to settle into and substantially fill the pens; flowing a second fluidic medium that does not contain micro-objects into the flow path at a flow rate sufficiently slow such that micro-objects which have settled into the pens are substantially not swept into the flow path; repositioning the microfluidic device into an unloading position such that the flow path is located beneath the openings of the pens; and allowing gravity to act on the micro-objects in the pens for an amount of time sufficient for the micro-objects to settle into the flow path, thereby generating a fluidic medium having a substantially uniform micro-object density. The pens can be identically sized, and can open off a common side of the flow path. The pens can be defined by lateral walls that are oriented substantially perpendicular to the flow of fluidic medium in the flow path.

In another aspect, the invention provides methods for concentrating micro-objects in a microfluidic device. The methods can comprise: flowing a fluidic medium comprising micro-objects into a flow path of a microfluidic device having a concentration chamber opening off one side of the flow path; arresting the flow of the fluidic medium within the flow path; repositioning the microfluidic device such that the flow path is located about the concentration chamber; and allowing gravity to act on the micro-objects in the fluidic medium for an amount of time sufficient for the micro-objects to settle into and substantially fill a distal end of the concentration chamber. The concentration chamber can have a chamfered opening, and the distal end can have a volume that is smaller than the volume of the chamfered opening. The microfluidic device can include a plurality of such concentration chambers.

In another aspect, the invention provides methods for culturing micro-objects in a microfluidic device. The method can comprise: disposing one or more cells in a sequestration pen of a microfluidic device; positioning the microfluidic device such that (i) an axis perpendicular to the plane of said microfluidic device (e.g., the plane of the microfluidic circuit or the support structure/base) is skewed relative to the gravitational force vector acting on the microfluidic device, and (ii) the force of gravity acting on the one or more cells tends to retain the cells within the sequestration pen; and incubating the one or more cells within the sequestration pen while the microfluidic device is so positioned. The sequestration pens can be configured in any of the manners disclosed herein. For example, the sequestration pen can include a connection region and an isolation region, and the one or more cells can be disposed in the isolation region. The perpendicular axis, can be skewed relative to the gravitational force vector, for example, by about 0.1 to about 90 degrees (e.g., about 0.5 to about 90 degrees, about 0.5 to about 45 degrees, about 0.5 to about 30 degrees, about 0.5 to about 15 degrees, about 0.5 to about 10 degrees, about 0.5 to about 5 degrees, or about 1 to about 2 degrees). In certain embodiments, the microfluidic device can include a plurality of sequestration pens, and one or more (e.g., a majority or each) of the sequestration pens can have one or more cells disposed therein. In certain embodiments, the methods further comprise, while incubating the one or more cells in the sequestration pen, continuously or periodically perfusing cell culture medium through a flow path (or channel) off of which the sequestration pen opens. During the incubation, the microfluidic device can be maintained at a specific temperature (e.g., at least 25° C., or between about 30° C. and 38° C.). In certain embodiments, the one or more cells can divide during the incubation. In certain related embodiments, a single cell can be disposed in the sequestration pen, and the incubating step can take place for a sufficient amount of time such that the single cell divides one or more times to form a clonal population of cells.

In another aspect, the invention provides a system for manipulating micro-objects within a microfluidic device. The system can include: a support configured to hold a microfluidic device in an orientation such that an axis perpendicular to the plane of the microfluidic device (e.g., the plane of the microfluidic circuit or the support structure/base) is skewed relative to a gravitational force vector acting on the microfluidic device; an optical train configured to (1) receive light from a first light source and focus the received light on at least a portion of a microfluidic device held by the support, and (2) receive light that is reflected or emitted from the microfluidic device, and any fluid and micro-objects contained within the microfluidic device, and direct at least a portion of the reflected or emitted light on a detector; and an AC voltage source configured to apply a voltage potential to the microfluidic device and thereby generate an electrokinetic force within an enclosure of said microfluidic device. The perpendicular axis, can be skewed relative to the gravitational force vector, for example, by about 0.1 to about 90 degrees (e.g., about 0.5 to about 90 degrees, about 0.5 to about 45 degrees, about 0.5 to about 30 degrees, about 0.5 to about 15 degrees, about 0.5 to about 10 degrees, about 0.5 to about 5 degrees, or about 1 to about 2 degrees).

In certain embodiments, the support is configured to rotate about at least one axis such that the microfluidic device can be held in a horizontal orientation, a vertical orientation, an inverted orientation, or any orientation therebetween.

In certain embodiments, the system further comprises the first light source, the detector, the microfluidic device, or any combination thereof. The microfluidic device can be any microfluidic device described herein. The system can further comprise a controller for controlling the activation of individual conductors (or electrodes) or subsets of conductors (or electrodes) in the microfluidic device (e.g., while the voltage potential and/or other signals (e.g., light) is being applied to the microfluidic device). The system can further comprise a spatial light modulator and a controller for controlling said spatial light modulator, and the optical train can be further configured to receive modulated light from the spatial light modulator and focus the modulated light onto at least a portion of a microfluidic device held by the support. The spatial light modulator can include a digital mirror device (DMD), a liquid crystal display, or the like. The system can further include a second light source. The second light source can, for example, provides unstructured light to the spatial light modulator.

In certain embodiments, the microfluidic device can include an array of phototransistors.

In certain embodiments, the detector can include an imaging device. The imaging device can include a charge-coupled device (CCD) or a camera.

In another aspect, the invention provides a machine readable storage device for storing non-transitory machine readable instructions for causing control equipment to perform a process in a microfluidic device that includes a flow path configured to contain a flow of a fluidic medium, and a microfluidic sequestration pen, wherein the sequestration pen has an opening in fluid communication with said flow path. The process can include: controlling the flow of the fluidic medium through the flow path; and repositioning (or tilting) the microfluidic device to alter the orientation of a gravitational force vector in relation to the flow path and the sequestration pen, thereby enabling micro-objects in the fluidic medium to exit the flow path and enter into an interior of the sequestration pen under the force of gravity. In certain embodiments, controlling the flow of the fluidic medium through the flow path includes synchronizing the flow with the tilting of the microfluidic device. For example, the flow can be stopped prior to tilting the microfluidic device.

BRIEF DESCRIPTION OF THE DRAWINGS

FIGS. 5A-5F provide various cross-section, schematic views of a microfluidic device having a microfluidic channel and a sequestration pen, and a process by which a target micro-object is trapped and transferred to the sequestration pen according to some embodiments of the invention.

FIGS. 17A-17D show time elapsed photographs of cell division and growth in sequestration pens that have been tilted according to a specific embodiment of the invention.

DETAILED DESCRIPTION OF EXEMPLARY EMBODIMENTS

Figure 1:
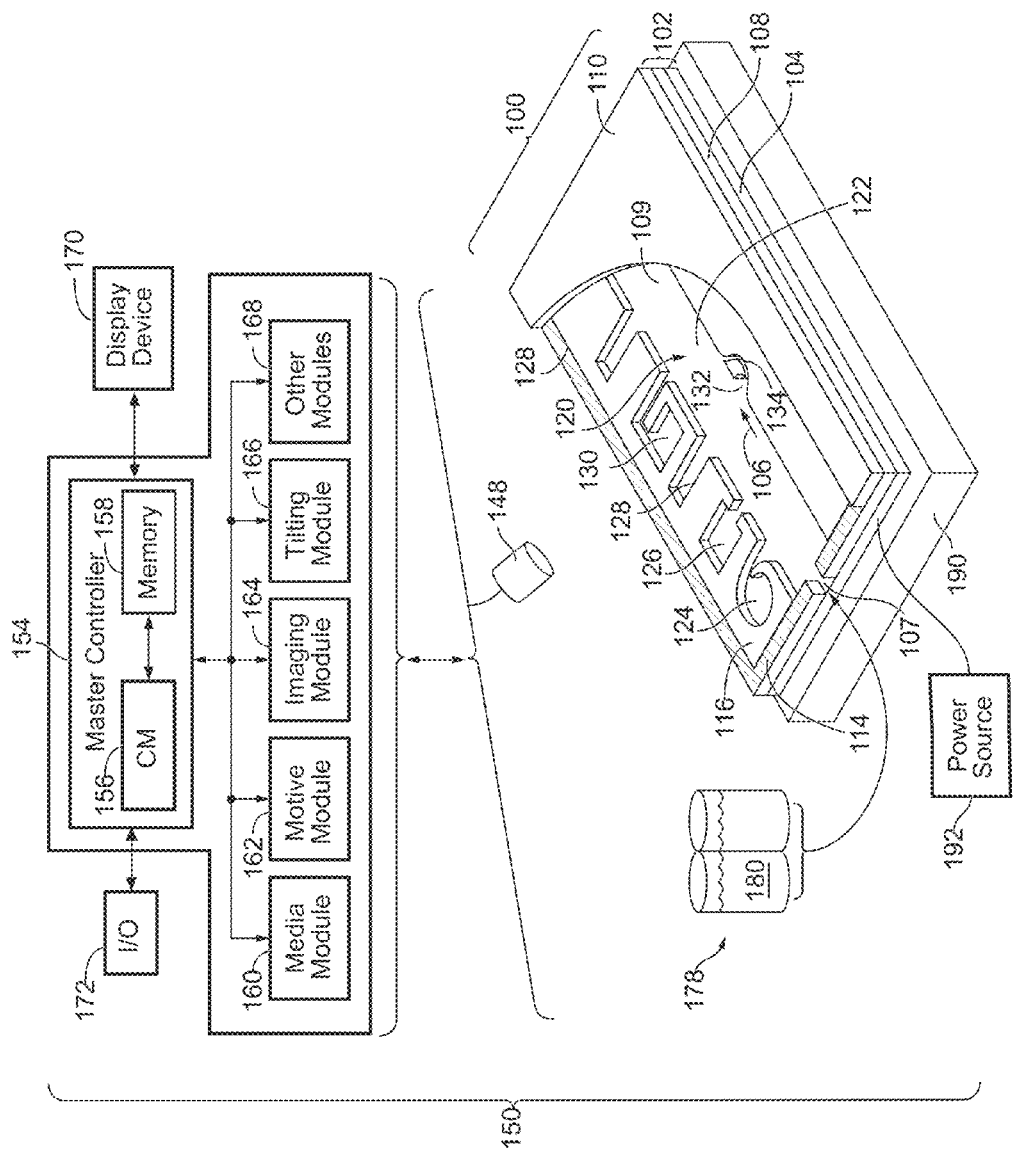
FIG. 1 illustrates an example of a system for use with a microfluidic device and associated control equipment according to some embodiments of the invention.

This specification describes exemplary embodiments and applications of the invention. The invention, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. In addition, where reference is made to a list of elements (e.g., elements a, b, c), such reference is intended to include any one of the listed elements by itself, any combination of less than all of the listed elements, and/or a combination of all of the listed elements.

Section divisions in the specification are for ease of review only and do not limit any combination of elements discussed.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

As used herein, the term "ones" means more than one. As used herein, the term "plurality" can be 2, 3, 4, 5, 6, 7, 8, 9, 10, or more.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least two ports configured to allow the fluid (and, optionally, micro-objects suspended in the fluid) to flow into and/or out of the microfluidic device. Typically, a microfluidic circuit of a microfluidic device will include at least one microfluidic channel and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 µL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 µL.

As used herein, a "nanofluidic device" or "nanofluidic apparatus" is a type of microfluidic device having a microfluidic circuit that contains at least one circuit element configured to hold a volume of fluid of less than about 1 µL, e.g., less than about 750, 500, 250, 200, 150, 100, 75, 50, 25, 20, 15, 10, 9, 8, 7, 6, 5, 4, 3, 2, 1 nL or less. Typically, a nanofluidic device will comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements is configured to hold a volume of fluid of about 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is in the range of from about 100,000 microns to about 500,000 microns, including any range therebetween. In some embodiments, the horizontal dimension is in the range of from about 100 microns to about 1000 microns (e.g., about 150 to about 500 microns) and the vertical dimension is in the range of from about 25 microns to about 200 microns, e.g., from about 40 to about 150 microns. It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, a microfluidic sequestration pen and a microfluidic channel, or a connection region and an isolation region of a microfluidic sequestration pen.

As used herein, the term "constriction" refers generally to a narrowing of a width of a circuit element (or an interface between two circuit elements) in a microfluidic device. The constriction can be located, for example, at the interface between a microfluidic sequestration pen and a microfluidic channel, or at the interface between an isolation region and a connection region of a microfluidic sequestration pen.

As used herein, the term "transparent" refers to a material which allows visible light to pass through without substantially altering the light as is passes through.

As used herein, the term "micro-object" refers generally to any microscopic object that may be isolated and collected in accordance with the present invention. Non-limiting examples of micro-objects include: inanimate micro-objects such as microparticles; microbeads (e.g., polystyrene beads, Luminex™ beads, or the like); magnetic beads; microrods; microwires; quantum dots, and the like; biological micro-objects such as cells (e.g., embryos, oocytes, sperm cells, cells dissociated from a tissue, eukaryotic cells, protist cells, animal cells, mammalian cells, human cells, immunological cells, hybridomas, cultured cells, cells from a cell line, cancer cells, infected cells, transfected and/or transformed cells, reporter cells, prokaryotic cell, and the like); biological organelles; vesicles, or complexes; synthetic vesicles; liposomes (e.g., synthetic or derived from membrane preparations); lipid nanorafts (as described in Ritchie et al. (2009) "Reconstitution of Membrane Proteins in Phospholipid Bilayer Nanodiscs," Methods Enzymol., 464:211-231), and the like; or a combination of inanimate micro-objects and biological micro-objects (e.g., microbeads attached to cells, liposome-coated micro-beads, liposome-coated magnetic beads, or the like). Beads may further have other moieties/molecules covalently or non-covalently attached, such as fluorescent labels, proteins, small molecule signaling moieties, antigens, or chemical/biological species capable of use in an assay.

As used herein, the term "maintaining (a) cell(s)" refers to providing an environment comprising both fluidic and gaseous components and, optionally a surface, that provides the conditions necessary to keep the cells viable and/or expanding.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result.

The phrase "substantially no flow" refers to a rate of flow of a fluidic medium that, averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

The capability of biological micro-objects (e.g., biological cells) to produce specific biological materials (e.g., proteins, such as antibodies) can be assayed in such a microfluidic device. In a specific embodiment of an assay, sample material comprising biological micro-objects (e.g., cells) to be assayed for production of an analyte of interest can be loaded into a swept region of the microfluidic device. Ones of the biological micro-objects (e.g., mammalian cells, such as human cells) can be selected for particular characteristics and disposed in unswept regions. The remaining sample material can then be flowed out of the swept region and an assay material flowed into the swept region. Because the selected biological micro-objects are in unswept regions, the selected biological micro-objects are not substantially affected by the flowing out of the remaining sample material or the flowing in of the assay material. The selected biological micro-objects can be allowed to produce the analyte of interest, which can diffuse from the unswept regions into the swept region, where the analyte of interest can react with the assay material to produce localized detectable reactions, each of which can be correlated to a particular unswept region. Any unswept region associated with a detected reaction can be analyzed to determine which, if any, of the biological micro-objects in the unswept region are sufficient producers of the analyte of interest.

Microfluidic Devices and Systems for Operating and Observing Such Devices.

FIG. 1 illustrates an example of a microfluidic device 100 and a system 150 which can be used in the practice of the present invention. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120. Although a single microfluidic circuit 120 is illustrated in FIG. 1, suitable microfluidic devices can include a plurality (e.g., 2 or 3) of such microfluidic circuits. Regardless, the microfluidic device 100 can be configured to be a nanofluidic device. In the embodiment illustrated in FIG. 1, the microfluidic circuit 120 comprises a plurality of microfluidic sequestration pens 124, 126, 128, and 130, each having one or more openings in fluidic communication with flow path 106. The microfluidic sequestration pens of the instant invention comprise various features and structures that have been optimized to collect and retain micro-objects under gravitational forces, even when a medium 180 is flowing through the flow path 106. Before turning to the foregoing, however, a brief description of microfluidic apparatus 100 and system 150 is provided.

As generally illustrated in FIG. 1, the microfluidic circuit 120 is defined by an enclosure 102. Although the enclosure 102 can be physically structured in different configurations, in the example shown in FIG. 1 the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120.

The support structure 104 can be at the bottom and the cover 110 at the top of the microfluidic circuit 120 as illustrated in FIG. 1. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110. Only one port 107 is illustrated in FIG. 1 but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow channels, chambers, pens, traps, and the like. In the microfluidic circuit 120 illustrated in FIG. 1, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example the frame 114 can comprise a metal material.

The microfluidic circuit material 116 can be patterned with cavities or the like to define circuit elements and interconnections of the microfluidic circuit 120. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can compose microfluidic circuit material 116 include molded glass, an etchable material such as silicone (e.g. photo-patternable silicone or "PPS"), photo-resist (e.g., SU8), or the like. In some embodiments, such materials—and thus the microfluidic circuit material 116—can be rigid and/or substantially impermeable to gas. Regardless, microfluidic circuit material 116 can be disposed on the support structure 104 and inside the frame 114.

The cover 110 can be an integral part of the frame 114 and/or the microfluidic circuit material 116. Alternatively, the cover 110 can be a structurally distinct element, as illustrated in FIG. 1. The cover 110 can comprise the same or different materials than the frame 114 and/or the microfluidic circuit material 116. Similarly, the support structure 104 can be a separate structure from the frame 114 or microfluidic circuit material 116 as illustrated, or an integral part of the frame 114 or microfluidic circuit material 116. Likewise the frame 114 and microfluidic circuit material 116 can be separate structures as shown in FIG. 1 or integral portions of the same structure.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. 2012/0325665 (Chiou et al.), the contents of which are incorporated herein by reference. In some embodiments, the cover 110 can be modified (e.g., by conditioning all or part of a surface that faces inward toward the microfluidic circuit 120) to support cell adhesion, viability and/or growth. The modification may include a coating of a synthetic or natural polymer. In some embodiments, the cover 110 and/or the support structure 104 can be transparent to light. The cover 110 may also include at least one material that is gas permeable (e.g., PDMS or PPS).

FIG. 1 also shows a system 150 for operating and controlling microfluidic devices, such as microfluidic device 100. System 150, as illustrated, includes an electrical power source 192, an imaging device 194, and a tilting device 190.

The electrical power source 192 can provide electric power to the microfluidic device 100 and/or tilting device 190, providing biasing voltages or currents as needed. The electrical power source 192 can, for example, comprise one or more alternating current (AC) and/or direct current (DC) voltage or current sources. The imaging device 194 can comprise a device, such as a digital camera, for capturing images inside microfluidic circuit 120. In some instances, the imaging device 194 further comprises a detector having a fast frame rate and/or high sensitivity (e.g. for low light applications). The imaging device 194 can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high pressure mercury lamp) or a Xenon arc lamp. As discussed with respect to FIG. 3, the imaging device 194 may further include a microscope (or an optical train), which may or may not include an eyepiece.

System 150 further comprises a tilting device 190 configured to rotate a microfluidic device 100 about one or more axes of rotation. In some embodiments, the tilting device 190 is configured to support and/or hold the enclosure 102 comprising the microfluidic circuit 120 about at least one axis such that the microfluidic device 100 (and thus the microfluidic circuit 120) can be held in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, the tilting device 190 can tilt the microfluidic device 100 at 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35°, 40°, 45°, 50°, 55°, 60°, 65°, 70°, 75°, 80°, 90° relative to the x-axis or any degree therebetween. The level orientation (and thus the x- and y-axes) is defined as normal to a vertical axis defined by the force of gravity. The tilting device can also tilt the microfluidic device 100 (and the microfluidic circuit 120) to any degree greater than 90° relative to the x-axis and/or y-axis, or tilt the microfluidic device 100 (and the microfluidic circuit 120) 180° relative to the x-axis or the y-axis in order to fully invert the microfluidic device 100 (and the microfluidic circuit 120). Similarly, in some embodiments, the tilting device 190 tilts the microfluidic device 100 (and the microfluidic circuit 120) about an axis of rotation defined by flow path 106 or some other portion of microfluidic circuit 120.

In some instances, the microfluidic device 100 is tilted into a vertical orientation such that the flow path 106 is positioned above or below one or more sequestration pens. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path). The term "below" as used herein denotes that the flow path 106 is positioned lower than the one or more sequestration pens on a vertical axis defined by the force of gravity (i.e. an object in a sequestration pen below a flow path 106 would have a lower gravitational potential energy than an object in the flow path).

In some instances, the tilting device 190 tilts the microfluidic device 100 about an axis that is parallel to the flow path 106. Moreover, the microfluidic device 100 can be tilted to an angle of less than 90° such that the flow path 106 is located above or below one or more sequestration pens without being located directly above or below the sequestration pens. In other instances, the tilting device 190 tilts the microfluidic device 100 about an axis perpendicular to the flow path 106. In still other instances, the tilting device 190 tilts the microfluidic device 100 about an axis that is neither parallel nor perpendicular to the flow path 106.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1. Alternatively, the media source 178 can be located in whole or in part inside the enclosure 102 of the microfluidic device 100. For example, the media source 178 can comprise reservoirs that are part of the microfluidic device 100.

FIG. 1 also illustrates simplified block diagram depictions of examples of control and monitoring equipment 152 that constitute part of system 150 and can be utilized in conjunction with a microfluidic device 100. As shown, examples of such control and monitoring equipment 152 include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device 194 (e.g., a camera, microscope, light source or any combination thereof) for capturing images (e.g., digital images), and a tilting module 166 for controlling a tilting device 190. The control equipment 152 can also include other modules 168 for controlling, monitoring, or performing other functions with respect to the microfluidic device 100. As shown, the equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively or in addition, the control module 156 can comprise hardwired digital circuitry and/or analog circuitry. The media module 160, motive module 162, imaging module 164, tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, tilting module 166, and/or other modules 168 configured as discussed above. Similarly, the master controller 154, media module 160, motive module 162, imaging module 164, tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. For example, in some embodiments media module 160 stops the flow of media 180 in the flow path 106 and through the enclosure 102 prior to the tilting module 166 causing the tilting device 190 to tilt the microfluidic device 100 to a desired angle of incline.

The motive module 162 can be configured to control selection, trapping, and movement of micro-objects (not shown) in the microfluidic circuit 120. As discussed below with respect to FIGS. 2A and 2B, the enclosure 102 can comprise a dielectrophoresis (DEP), optoelectronic tweezers (OET) and/or opto-electrowetting (OEW) configuration (not shown in FIG. 1), and the motive module 162 can control the activation of electrodes and/or transistors (e.g., phototransistors) to select and move micro-objects (not shown) and/or droplets of medium (not shown) in the flow path 106 and/or sequestration pens 124, 126, 128, 130.

The imaging module 164 can control the imaging device 194. For example, the imaging module 164 can receive and process image data from the imaging device 194. Image data from the imaging device 194 can comprise any type of information captured by the imaging device 194 (e.g., the presence or absence of micro-objects, droplets of medium, accumulation of label, such as fluorescent label, etc.). Using the information captured by the imaging device 194, the imaging module 164 can further calculate the position of objects (e.g., micro-objects, droplets of medium) and/or the rate of motion of such objects within the microfluidic device 100.

The tilting module 166 can control the tilting motions of tilting device 190. Alternatively or in addition, the tilting module 166 can control the tilting rate and timing to optimize transfer of micro-objects to the one or more sequestration pens via gravitational forces. The tilting module 166 is communicatively coupled with the imaging module 164 to receive data describing the motion of micro-objects and/or droplets of medium in the microfluidic circuit 120. Using this data, the tilting module 166 may adjust the tilt of the microfluidic circuit 120 in order to adjust the rate at which micro-objects and/or droplets of medium move in the microfluidic circuit 120. The tilting module 166 may also use this data to iteratively adjust the position of a micro-object and/or droplet of medium in the microfluidic circuit 120.

In the example shown in FIG. 1, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. In some instances, pens 124, 126, 128, 130 are configured to physically corral one or more micro-objects within the microfluidic circuit 120. Sequestration pens in accordance with the present invention can comprise various shapes, surfaces and features that are optimized for use with DEP, OET, OEW, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful in performing assays (e.g. culturing and retaining micro-objects used in assays). In some embodiments, the microfluidic circuit 120 comprises a plurality of identical microfluidic sequestration pens. In some embodiments, the microfluidic circuit 120 comprises a plurality of microfluidic sequestration pens, wherein two or more of the sequestration pens comprise differing structures and/or features. For example, the sequestration pens can provide differing benefits with regard to performing assays.

In the embodiment illustrated in FIG. 1, a single channel 122 and flow path 106 is shown. However, other embodiments may contain multiple channels 122, each configured to comprise a flow path 106. The microfluidic circuit 120 further comprises an inlet valve or port 107 in fluid communication with the flow path 106 and fluidic medium 180, whereby fluidic medium 180 can access channel 122 via the inlet port 107. In some instances, the flow path 106 comprises a single path. In some instances, the single path is arranged in a zigzag pattern whereby the flow path 106 travels across the microfluidic device 100 two or more times in alternating directions.

In some instances, microfluidic circuit 120 comprises a plurality of parallel channels 122 and flow paths 106, wherein the fluidic medium 180 within each flow path 106 flows in the same direction. In some instances, the fluidic medium within each flow path 106 flows in at least one of a forward or reverse direction. In some instances, a plurality of sequestration pens are configured (e.g., relative to a channel 122) such that they can be loaded with target micro-objects in parallel.

In some embodiments, microfluidic circuit 120 further comprises one or more micro-object traps 132. The traps 132 are generally formed in a wall forming the boundary of a channel 122, and may be positioned opposite an opening of one or more of the microfluidic sequestration pens 124, 126, 128, 130. In some embodiments, the traps 132 are configured to receive or capture a single micro-object from the flow path 106. In some embodiments, the traps 132 are configured to receive or capture a plurality of micro-objects from the flow path 106. In some instances, the traps 132 comprise a volume approximately equal to the volume of a single target micro-object.

The traps 132 may further comprise an opening which is configured to assist the flow of targeted micro-objects into the traps 132. In some instances, the traps 132 comprise an opening having a height and width that is approximately equal to the dimensions of a single target micro-object, whereby larger micro-objects are prevented from entering into the micro-object trap. The traps 132 may further comprise other features configured to assist in retention of targeted micro-objects within the trap 132. In some instances, the trap 132 is aligned with and situated on the opposite side of a channel 122 relative to the opening of a microfluidic sequestration pen, such that upon tilting the microfluidic device 100 about an axis parallel to the channel 122, the trapped micro-object exits the trap 132 at a trajectory that causes the micro-object to settle into the opening of the sequestration pen. In some instances, the trap 132 comprises a side passage 134 that is smaller than the target micro-object in order to facilitate flow through the trap 132 and thereby increase the likelihood of capturing a micro-object in the trap 132.

In some embodiments, dielectrophoretic (DEP) forces are applied across the fluidic medium 180 (e.g., in the flow path and/or in the sequestration pens) via one or more electrodes (not shown) to manipulate, transport, separate and sort micro-objects located therein. For example, in some embodiments, DEP forces are applied to one or more portions of microfluidic circuit 120 in order to transfer a single micro-object from the flow path 106 into a desired microfluidic sequestration pen. In some embodiments, DEP forces are used to prevent a micro-object within a sequestration pen (e.g., sequestration pen 124, 126, 128, or 130) from being displaced therefrom. Further, in some embodiments, DEP forces are used to selectively remove a micro-object from a sequestration pen that was previously collected in accordance with the teachings of the instant invention. In some embodiments, the DEP forces comprise optoelectronic tweezer (OET) forces.

In other embodiments, optoelectrowetting (OEW) forces are applied to one or more positions in the support structure 104 (and/or the cover 110) of the microfluidic device 100 (e.g., positions helping to define the flow path and/or the sequestration pens) via one or more electrodes (not shown) to manipulate, transport, separate and sort droplets located in the microfluidic circuit 120. For example, in some embodiments, OEW forces are applied to one or more positions in the support structure 104 (and/or the cover 110) in order to transfer a single droplet from the flow path 106 into a desired microfluidic sequestration pen. In some embodiments, OEW forces are used to prevent a droplet within a sequestration pen (e.g., sequestration pen 124, 126, 128, or 130) from being displaced therefrom. Further, in some embodiments, OEW forces are used to selectively remove a droplet from a sequestration pen that was previously collected in accordance with the teachings of the instant invention.

In some embodiments, DEP and/or OEW forces are combined with other forces, such as flow and/or gravitational force, so as to manipulate, transport, separate and sort micro-objects and/or droplets within the microfluidic circuit 120. For example, the enclosure 102 can be tilted (e.g., by tilting device 190) to position the flow path 106 and micro-objects located therein above the microfluidic sequestration pens, and the force of gravity can transport the micro-objects and/or droplets into the pens. In some embodiments, the DEP and/or OEW forces can be applied prior to the other forces. In other embodiments, the DEP and/or OEW forces can be applied after the other forces. In still other instances, the DEP and/or OEW forces can be applied at the same time as the other forces or in an alternating manner with the other forces.

Figure 2A:
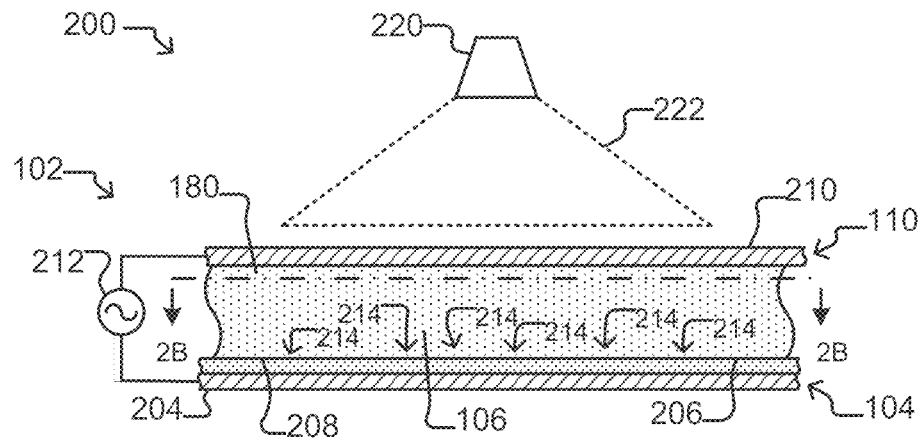
FIGS. 2A and 2B illustrate a microfluidic device according to some embodiments of the invention.

FIGS. 2A-2F illustrates various embodiments of microfluidic devices that can be used in the practice of the present invention. FIG. 2A depicts an embodiment in which the microfluidic device 200 is configured as an optically-actuated electrokinetic device. A variety of optically-actuated electrokinetic devices are known in the art, including devices having an optoelectronic tweezer (OET) configuration and devices having an opto-electrowetting (OEW) configuration. Examples of suitable OET configurations are illustrated in the following U.S. patent documents, each of which is incorporated herein by reference in its entirety: U.S. Pat. No. RE 44,711 (Wu et al.) (originally issued as U.S. Pat. No. 7,612,355); and U.S. Pat. No. 7,956,339 (Ohta et al.). Examples of OEW configurations are illustrated in U.S. Pat. No. 6,958,132 (Chiou et al.) and U.S. Patent Application Publication No. 2012/0024708 (Chiou et al.), both of which are incorporated by reference herein in their entirety. Yet another example of an optically-actuated electrokinetic device includes a combined OET/OEW configuration, examples of which are shown in U.S. Patent Publication Nos. 20150306598 (Khandros et al.) and 20150306599 (Khandros et al.) and their corresponding PCT Publications WO2015/164846 and WO2015/164847, all of which are incorporated herein by reference in their entirety.

Motive Microfluidic Device Configurations.

As described above, the control and monitoring equipment of the system can comprise a motive module 162 for selecting and moving objects, such as micro-objects or droplets, in the microfluidic circuit of a microfluidic device. The microfluidic device can have a variety of motive configurations, depending upon the type of object being moved and other considerations. For example, a dielectrophoresis (DEP) configuration can be utilized to select and move micro-objects in the microfluidic circuit. Thus, the support structure 104 and/or cover 110 of the microfluidic device 100 can comprise a DEP configuration for selectively inducing DEP forces on micro-objects in a fluidic medium 180 in the microfluidic circuit 120 and thereby select, capture, and/or move individual micro-objects or groups of micro-objects. Alternatively, the support structure 104 and/or cover 110 of the microfluidic device 100 can comprise an electrowetting (EW) configuration for selectively inducing EW forces on droplets in a fluidic medium 180 in the microfluidic circuit 120 and thereby select, capture, and/or move individual droplets or groups of droplets.

Figure 2B:
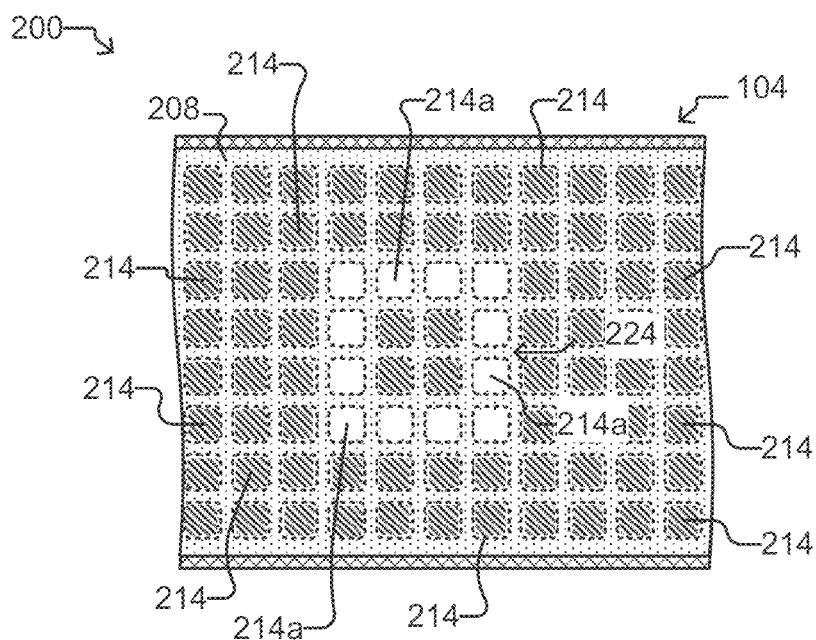

One example of a microfluidic device 200 comprising a DEP configuration is illustrated in FIGS. 2A and 2B. While for purposes of simplicity FIGS. 2A and 2B show a side cross-sectional view and a top cross-sectional view, respectively, of a portion of an enclosure 102 of the microfluidic device 200 having an open region/chamber 202, it should be understood that the region/chamber 202 may be part of a fluidic circuit element having a more detailed structure, such as a growth chamber, a sequestration pen, a flow region, or a flow channel. Furthermore, the microfluidic device 200 may include other fluidic circuit elements. For example, the microfluidic device 200 can include a plurality of growth chambers or sequestration pens and/or one or more flow regions or flow channels, such as those described herein with respect to microfluidic device 100. A DEP configuration may be incorporated into any such fluidic circuit elements of the microfluidic device 200, or select portions thereof. It should be further appreciated that any of the above or below described microfluidic device components and system components may be incorporated in and/or used in combination with the microfluidic device 200. For example, system 150 including control and monitoring equipment 152, described above, may be used with microfluidic device 200, including one or more of the media module 160, motive module 162, imaging module 164, tilting module 166, and other modules 168.

As seen in FIG. 2A, the microfluidic device 200 includes a support structure 104 having a bottom electrode 204 and an electrode activation substrate 206 overlying the bottom electrode 204, and a cover 110 having a top electrode 210, with the top electrode 210 spaced apart from the bottom electrode 204. The top electrode 210 and the electrode activation substrate 206 define opposing surfaces of the region/chamber 202. A medium 180 contained in the region/chamber 202 thus provides a resistive connection between the top electrode 210 and the electrode activation substrate 206. A power source 212 configured to be connected to the bottom electrode 204 and the top electrode 210 and create a biasing voltage between the electrodes, as required for the generation of DEP forces in the region/chamber 202, is also shown. The power source 212 can be, for example, an alternating current (AC) power source.

In certain embodiments, the microfluidic device 200 illustrated in FIGS. 2A and 2B can have an optically-actuated DEP configuration. Accordingly, changing patterns of light 222 from the light source 220, which may be controlled by the motive module 162, can selectively activate and deactivate changing patterns of DEP electrodes at regions 214 of the inner surface 208 of the electrode activation substrate 206. (Hereinafter the regions 214 of a microfluidic device having a DEP configuration are referred to as "DEP electrode regions.") As illustrated in FIG. 2B, a light pattern 222 directed onto the inner surface 208 of the electrode activation substrate 206 can illuminate select DEP electrode regions 214a (shown in white) in a pattern, such as a square. The non-illuminated DEP electrode regions 214 (cross-hatched) are hereinafter referred to as "dark" DEP electrode regions 214. The relative electrical impedance through the DEP electrode activation substrate 206 (i.e., from the bottom electrode 204 up to the inner surface 208 of the electrode activation substrate 206 which interfaces with the medium 180 in the flow region 106) is greater than the relative electrical impedance through the medium 180 in the region/chamber 202 (i.e., from the inner surface 208 of the electrode activation substrate 206 to the top electrode 210 of the cover 110) at each dark DEP electrode region 214. An illuminated DEP electrode region 214a, however, exhibits a reduced relative impedance through the electrode activation substrate 206 that is less than the relative impedance through the medium 180 in the region/chamber 202 at each illuminated DEP electrode region 214a.

With the power source 212 activated, the foregoing DEP configuration creates an electric field gradient in the fluidic medium 180 between illuminated DEP electrode regions 214a and adjacent dark DEP electrode regions 214, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 214 at the inner surface 208 of the region/chamber 202 by changing light patterns 222 projected from a light source 220 into the microfluidic device 200. Whether the DEP forces attract or repel nearby micro-objects can depend on such parameters as the frequency of the power source 212 and the dielectric properties of the medium 180 and/or micro-objects (not shown).

The square pattern 224 of illuminated DEP electrode regions 214a illustrated in FIG. 2B is an example only. Any pattern of the DEP electrode regions 214 can be illuminated (and thereby activated) by the pattern of light 222 projected into the device 200, and the pattern of illuminated/activated DEP electrode regions 214 can be repeatedly changed by changing or moving the light pattern 222.

In some embodiments, the electrode activation substrate 206 can comprise or consist of a photoconductive material. In such embodiments, the inner surface 208 of the electrode activation substrate 206 can be featureless. For example, the electrode activation substrate 206 can comprise or consist of a layer of hydrogenated amorphous silicon (a-Si:H). The a-Si:H can comprise, for example, about 8% to 40% hydrogen (calculated as 100*(the number of hydrogen atoms)/(the total number of hydrogen and silicon atoms)). The layer of a-Si:H can have a thickness of about 500 nm to about 2.0 In such embodiments, the DEP electrode regions 214 can be created anywhere and in any pattern on the inner surface 208 of the electrode activation substrate 208, in accordance with the light pattern 222. The number and pattern of the DEP electrode regions 214 thus need not be fixed, but can correspond to the light pattern 222. Examples of microfluidic devices having a DEP configuration comprising a photoconductive layer such as discussed above have been described, for example, in U.S. Pat. No. RE 44,711 (Wu et al.) (originally issued as U.S. Pat. No. 7,612,355), the entire contents of which are incorporated herein by reference.

In other embodiments, the electrode activation substrate 206 can comprise a substrate comprising a plurality of doped layers, electrically insulating layers (or regions), and electrically conductive layers that form semiconductor integrated circuits, such as is known in semiconductor fields. For example, the electrode activation substrate 206 can comprise a plurality of phototransistors, including, for example, lateral bipolar phototransistors, each phototransistor corresponding to a DEP electrode region 214. Alternatively, the electrode activation substrate 206 can comprise electrodes (e.g., conductive metal electrodes) controlled by phototransistor switches, with each such electrode corresponding to a DEP electrode region 214. The electrode activation substrate 206 can include a pattern of such phototransistors or phototransistor-controlled electrodes. The pattern, for example, can be an array of substantially square phototransistors or phototransistor-controlled electrodes arranged in rows and columns, such as shown in FIG. 2B. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 214 at the inner surface 208 of the electrode activation substrate 206 and the bottom electrode 210, and those electrical connections (i.e., phototransistors or electrodes) can be selectively activated and deactivated by the light pattern 222. When not activated, each electrical connection can have high impedance such that the relative impedance through the electrode activation substrate 206 (i.e., from the bottom electrode 204 to the inner surface 208 of the electrode activation substrate 206 which interfaces with the medium 180 in the region/chamber 202) is greater than the relative impedance through the medium 180 (i.e., from the inner surface 208 of the electrode activation substrate 206 to the top electrode 210 of the cover 110) at the corresponding DEP electrode region 214. When activated by light in the light pattern 222, however, the relative impedance through the electrode activation substrate 206 is less than the relative impedance through the medium 180 at each illuminated DEP electrode region 214, thereby activating the DEP electrode at the corresponding DEP electrode region 214 as discussed above. DEP electrodes that attract or repel micro-objects (not shown) in the medium 180 can thus be selectively activated and deactivated at many different DEP electrode regions 214 at the inner surface 208 of the electrode activation substrate 206 in the region/chamber 202 in a manner determined by the light pattern 222.

Examples of microfluidic devices having electrode activation substrates that comprise phototransistors have been described, for example, in U.S. Pat. No. 7,956,339 (Ohta et al.) (see, e.g., device 300 illustrated in FIGS. 21 and 22, and descriptions thereof), the entire contents of which are incorporated herein by reference. Examples of microfluidic devices having electrode activation substrates that comprise electrodes controlled by phototransistor switches have been described, for example, in U.S. Patent Publication No. 2014/0124370 (Short et al.) (see, e.g., devices 200, 400, 500, 600, and 900 illustrated throughout the drawings, and descriptions thereof), the entire contents of which are incorporated herein by reference.

In some embodiments of a DEP configured microfluidic device, the top electrode 210 is part of a first wall (or cover 110) of the enclosure 102, and the electrode activation substrate 206 and bottom electrode 204 are part of a second wall (or support structure 104) of the enclosure 102. The region/chamber 202 can be between the first wall and the second wall. In other embodiments, the electrode 210 is part of the second wall (or support structure 104) and one or both of the electrode activation substrate 206 and/or the electrode 210 are part of the first wall (or cover 110). Moreover, the light source 220 can alternatively be used to illuminate the enclosure 102 from below.

With the microfluidic device 200 of FIGS. 2A-2B having a DEP configuration, the motive module 162 can select a micro-object (not shown) in the medium 180 in the region/chamber 202 by projecting a light pattern 222 into the device 200 to activate a first set of one or more DEP electrodes at DEP electrode regions 214a of the inner surface 208 of the electrode activation substrate 206 in a pattern (e.g., square pattern 224) that surrounds and captures the micro-object. The motive module 162 can then move the captured micro-object by moving the light pattern 222 relative to the device 200 to activate a second set of one or more DEP electrodes at DEP electrode regions 214. Alternatively, the device 200 can be moved relative to the light pattern 222.

In other embodiments, the microfluidic device 200 can have a DEP configuration that does not rely upon light activation of DEP electrodes at the inner surface 208 of the electrode activation substrate 206. For example, the electrode activation substrate 206 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 214, thereby creating a net DEP force on a micro-object (not shown) in region/chamber 202 in the vicinity of the activated DEP electrodes. Depending on such characteristics as the frequency of the power source 212 and the dielectric properties of the medium (not shown) and/or micro-objects in the region/chamber 202, the DEP force can attract or repel a nearby micro-object. By selectively activating and deactivating a set of DEP electrodes (e.g., at a set of DEP electrodes regions 214 that forms a square pattern 224), one or more micro-objects in region/chamber 202 can be trapped and moved within the region/chamber 202. The motive module 162 in FIG. 1 can control such switches and thus activate and deactivate individual ones of the DEP electrodes to select, trap, and move particular micro-objects (not shown) around the region/chamber 202. Microfluidic devices having a DEP configuration that includes selectively addressable and energizable electrodes are known in the art and have been described, for example, in U.S. Pat. No. 6,294,063 (Becker et al.) and U.S. Pat. No. 6,942,776 (Medoro), the entire contents of which are incorporated herein by reference.

As yet another example, the microfluidic device 200 can have an electrowetting (EW) configuration, which can be in place of the DEP configuration or can be located in a portion of the microfluidic device 200 that is separate from the portion which has the DEP configuration. The EW configuration can be an opto-electrowetting configuration or an electrowetting on dielectric (EWOD) configuration, both of which are known in the art. In some EW configurations, the support structure 104 has an electrode activation substrate 206 sandwiched between a dielectric layer (not shown) and the bottom electrode 204. The dielectric layer can comprise a hydrophobic material and/or can be coated with a hydrophobic material. For microfluidic devices 200 that have an EW configuration, the inner surface 208 of the support structure 104 is the inner surface of the dielectric layer or its hydrophobic coating.

The dielectric layer (not shown) can comprise one or more oxide layers, and can have a thickness of about 50 nm to about 250 nm (e.g., about 125 nm to about 175 nm). In certain embodiments, the dielectric layer may comprise a layer of oxide, such as a metal oxide (e.g., aluminum oxide or hafnium oxide). In certain embodiments, the dielectric layer can comprise a dielectric material other than a metal oxide, such as silicon oxide or a nitride. Regardless of the exact composition and thickness, the dielectric layer can have an impedance of about 10 kOhms to about 50 kOhms.

In some embodiments, the surface of the dielectric layer that faces inward toward region/chamber 202 is coated with a hydrophobic material. The hydrophobic material can comprise, for example, fluorinated carbon molecules. Examples of fluorinated carbon molecules include perfluoro-polymers such as polytetrafluoroethylene (e.g., TEFLON®) or poly (2,3-difluoromethylenyl-perfluorotetrahydrofuran) (e.g., CYTOP™). Molecules that make up the hydrophobic material can be covalently bonded to the surface of the dielectric layer. For example, molecules of the hydrophobic material can be covalently bound to the surface of the dielectric layer by means of a linker, such as a siloxane group, a phosphonic acid group, or a thiol group. Thus, in some embodiments, the hydrophobic material can comprise alkyl-terminated siloxane, alkyl-termination phosphonic acid, or alkyl-terminated thiol. The alkyl group can be long-chain hydrocarbons (e.g., having a chain of at least 10 carbons, or at least 16, 18, 20, 22, or more carbons). Alternatively, fluorinated (or perfluorinated) carbon chains can be used in place of the alkyl groups. Thus, for example, the hydrophobic material can comprise fluoroalkyl-terminated siloxane, fluoroalkyl-terminated phosphonic acid, or fluoroalkyl-terminated thiol. In some embodiments, the hydrophobic coating has a thickness of about 10 nm to about 50 nm. In other embodiments, the hydrophobic coating has a thickness of less than 10 nm (e.g., less than 5 nm, or about 1.5 to 3.0 nm).

In some embodiments, the cover 110 of a microfluidic device 200 having an electrowetting configuration is coated with a hydrophobic material (not shown) as well. The hydrophobic material can be the same hydrophobic material used to coat the dielectric layer of the support structure 104, and the hydrophobic coating can have a thickness that is substantially the same as the thickness of the hydrophobic coating on the dielectric layer of the support structure 104. Moreover, the cover 110 can comprise an electrode activation substrate 206 sandwiched between a dielectric layer and the top electrode 210, in the manner of the support structure 104. The electrode activation substrate 206 and the dielectric layer of the cover 110 can have the same composition and/or dimensions as the electrode activation substrate 206 and the dielectric layer of the support structure 104. Thus, the microfluidic device 200 can have two electrowetting surfaces.

In some embodiments, the electrode activation substrate 206 can comprise a photoconductive material, such as described above. Accordingly, in certain embodiments, the electrode activation substrate 206 can comprise or consist of a layer of hydrogenated amorphous silicon (a-Si:H). The a-Si:H can comprise, for example, about 8% to 40% hydrogen (calculated as 100*(the number of hydrogen atoms)/(the total number of hydrogen and silicon atoms)). The layer of a-Si:H can have a thickness of about 500 nm to about 2.0 µm. Alternatively, the electrode activation substrate 206 can comprise electrodes (e.g., conductive metal electrodes) controlled by phototransistor switches, as described above. Microfluidic devices having an opto-electrowetting configuration are known in the art and/or can be constructed with electrode activation substrates known in the art. For example, U.S. Pat. No. 6,958,132 (Chiou et al.), the entire contents of which are incorporated herein by reference, discloses opto-electrowetting configurations having a photoconductive material such as a-Si:H, while U.S. Patent Publication No. 2014/0124370 (Short et al.), referenced above, discloses electrode activation substrates having electrodes controlled by phototransistor switches.

The microfluidic device 200 thus can have an opto-electrowetting configuration, and light patterns 222 can be used to activate photoconductive EW regions or photoresponsive EW electrodes in the electrode activation substrate 206. Such activated EW regions or EW electrodes of the electrode activation substrate 206 can generate an electrowetting force at the inner surface 208 of the support structure 104 (i.e., the inner surface of the overlaying dielectric layer or its hydrophobic coating). By changing the light patterns 222 (or moving microfluidic device 200 relative to the light source 220) incident on the electrode activation substrate 206, droplets (e.g., containing an aqueous medium, solution, or solvent) contacting the inner surface 208 of the support structure 104 can be moved through an immiscible fluid (e.g., an oil medium) present in the region/chamber 202.

In other embodiments, microfluidic devices 200 can have a EWOD configuration, and the electrode activation substrate 206 can comprise selectively addressable and energizable electrodes that do not rely upon light for activation. The electrode activation substrate 206 thus can include a pattern of such electrowetting (EW) electrodes. The pattern, for example, can be an array of substantially square EW electrodes arranged in rows and columns, such as shown in FIG. 2B. Alternatively, the pattern can be an array of substantially hexagonal EW electrodes that form a hexagonal lattice. Regardless of the pattern, the EW electrodes can be selectively activated (or deactivated) by electrical switches (e.g., transistor switches in a semiconductor substrate). By selectively activating and deactivating EW electrodes in the electrode activation substrate 206, droplets (not shown) contacting the inner surface 208 of the overlaying dielectric layer or its hydrophobic coating can be moved within the region/chamber 202. The motive module 162 in FIG. 1 can control such switches and thus activate and deactivate individual EW electrodes to select and move particular droplets around region/chamber 202. Microfluidic devices having a EWOD configuration with selectively addressable and energizable electrodes are known in the art and have been described, for example, in U.S. Pat. No. 8,685,344 (Sundarsan et al.), the entire contents of which are incorporated herein by reference.

Regardless of the configuration of the microfluidic device 200, a power source 212 can be used to provide a potential (e.g., an AC voltage potential) that powers the electrical circuits of the microfluidic device 200. The power source 212 can be the same as, or a component of, the power source 192 referenced in FIG. 1. Power source 212 can be configured to provide an AC voltage and/or current to the top electrode 210 and the bottom electrode 204. For an AC voltage, the power source 212 can provide a frequency range and an average or peak power (e.g., voltage or current) range sufficient to generate net DEP forces (or electrowetting forces) strong enough to trap and move individual micro-objects (not shown) in the region/chamber 202, as discussed above, and/or to change the wetting properties of the inner surface 208 of the support structure 104 (i.e., the dielectric layer and/or the hydrophobic coating on the dielectric layer) in the region/chamber 202, as also discussed above. Such frequency ranges and average or peak power ranges are known in the art. See, e.g., U.S. Pat. No. 6,958,132 (Chiou et al.), U.S. Pat. No. RE44,711 (Wu et al.) (originally issued as U.S. Pat. No. 7,612,355), and US Patent Application Publication Nos. US2014/0124370 (Short et al.), US2015/0306598 (Khandros et al.), and US2015/0306599 (Khandros et al.).

Sequestration Pens.

Figure 2C:
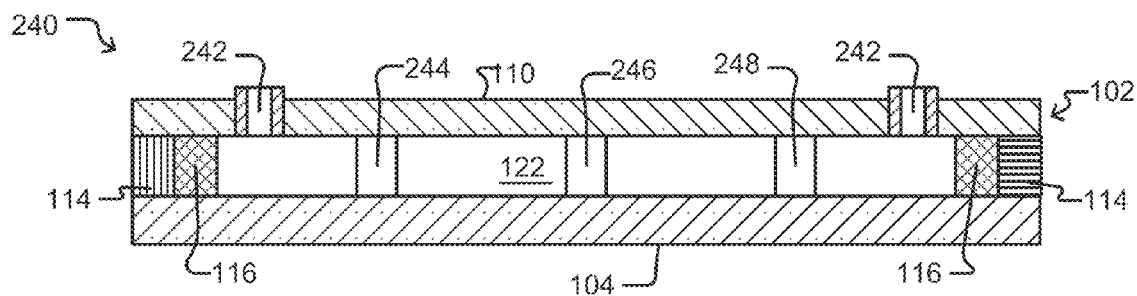
FIGS. 2C and 2D illustrate sequestration pens according to some embodiments of the invention.
Figure 2D:
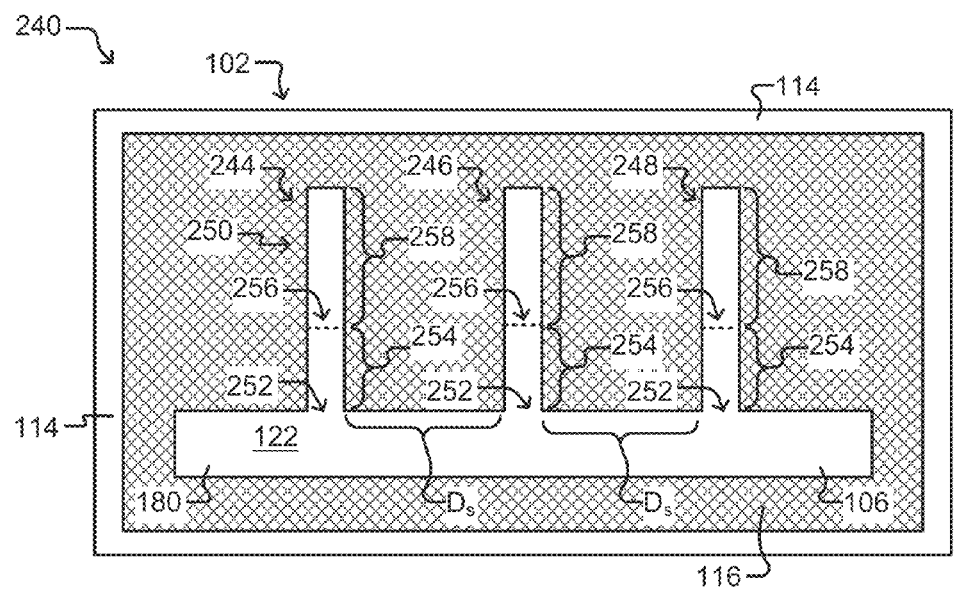

Non-limiting examples of generic sequestration pens 244, 246, and 248 are shown within the microfluidic device 240 depicted in FIGS. 2C and 2D. Each sequestration pen 244, 246, and 248 can comprise an isolation structure 250 defining an isolation region 258 and a connection region 254 fluidically connecting the isolation region 258 to a channel 122. The connection region 254 can comprise a proximal opening 252 to the channel 122 and a distal opening 256 to the isolation region 258. The connection region 254 can be configured so that the maximum penetration depth of a flow of a fluidic medium (not shown) flowing from the channel 122 into the sequestration pen 244, 246, 248 does not extend into the isolation region 258. Thus, due to the connection region 254, a micro-object (not shown) or other material (not shown) disposed in an isolation region 258 of a sequestration pen 244, 246, 248 can thus be isolated from, and not substantially affected by, a flow of medium 180 in the channel 122.

The channel 122 can thus be an example of a swept region, and the isolation regions 258 of the sequestration pens 244, 246, 248 can be examples of unswept regions. As noted, the channel 122 and sequestration pens 244, 246, 248 can be configured to contain one or more fluidic media 180. In the example shown in FIGS. 2C-2D, the ports 242 are connected to the channel 122 and allow a fluidic medium 180 to be introduced into or removed from the microfluidic device 240. Once the microfluidic device 240 contains the fluidic medium 180, the flow 260 of fluidic medium 180 in the channel 122 can be selectively generated and stopped. For example, as shown, the ports 242 can be disposed at different locations (e.g., opposite ends) of the channel 122, and a flow 260 of medium can be created from one port 242 functioning as an inlet to another port 242 functioning as an outlet.

Figure 2E:
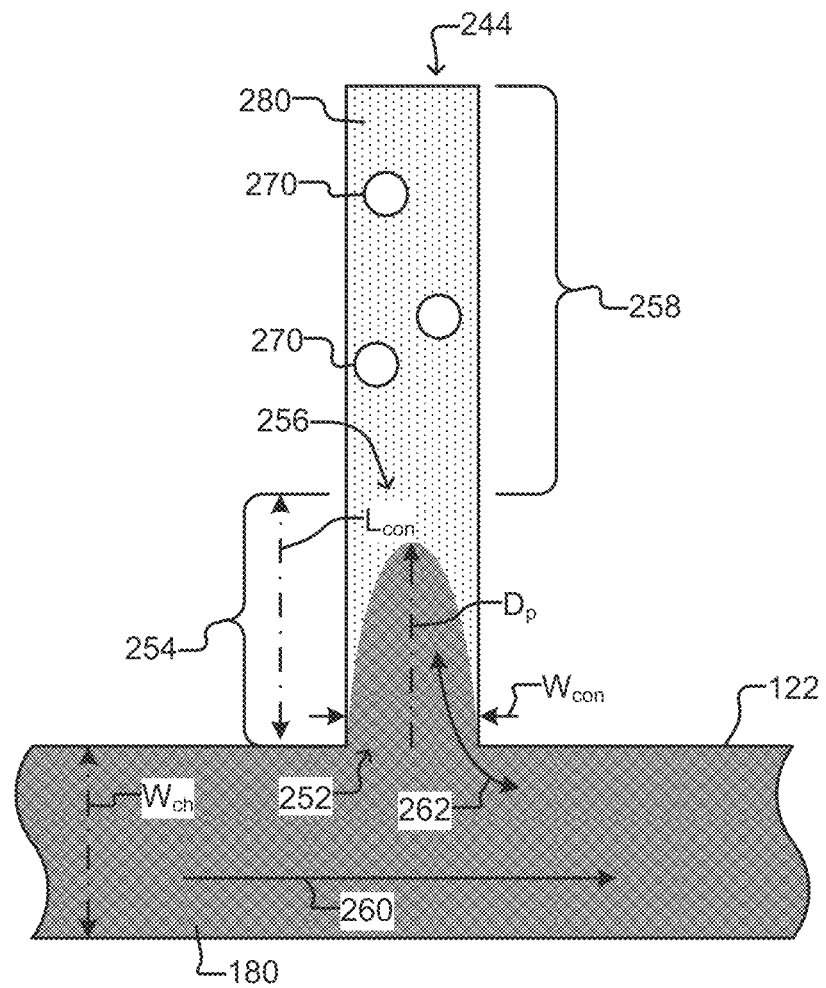
FIG. 2E provides a detailed illustration of a sequestration pen according to some embodiments of the invention.

FIG. 2E illustrates a detailed view of an example of a sequestration pen 244 according to the present invention. Examples of micro-objects 270 are also shown.

As is known, a flow 260 of fluidic medium 180 in a microfluidic channel 122 past a proximal opening 252 of sequestration pen 244 can cause a secondary flow 262 of the medium 180 into and/or out of the sequestration pen 244. To isolate micro-objects 270 in the isolation region 258 of a sequestration pen 244 from the secondary flow 262, the length $L_{con}$ of the connection region 254 of the sequestration pen 244 (i.e., from the proximal opening 252 to the distal opening 256) should be greater than the penetration depth $D_p$ of the secondary flow 262 into the connection region 254. The penetration depth $D_p$ of the secondary flow 262 depends upon the velocity of the fluidic medium 180 flowing in the channel 122 and various parameters relating to the configuration of the channel 122 and the proximal opening 252 of the connection region 254 to the channel 122. For a given microfluidic device, the configurations of the channel 122 and the opening 252 will be fixed, whereas the rate of flow 260 of fluidic medium 180 in the channel 122 will be variable. Accordingly, for each sequestration pen 244, a maximal velocity $V_{max}$ for the flow 260 of fluidic medium 180 in channel 122 can be identified that ensures that the penetration depth $D_p$ of the secondary flow 262 does not exceed the length $L_{con}$ of the connection region 254. As long as the rate of the flow 260 of fluidic medium 180 in the channel 122 does not exceed the maximum velocity $V_{max}$, the resulting secondary flow 262 can be limited to the channel 122 and the connection region 254 and kept out of the isolation region 258. The flow 260 of medium 180 in the channel 122 will thus not draw micro-objects 270 out of the isolation region 258. Rather, micro-objects 270 located in the isolation region 258 will stay in the isolation region 258 regardless of the flow 260 of fluidic medium 180 in the channel 122.

Moreover, as long as the rate of flow 260 of medium 180 in the channel 122 does not exceed $V_{max}$, the flow 260 of fluidic medium 180 in the channel 122 will not move miscellaneous particles (e.g., microparticles and/or nanoparticles) from the channel 122 into the isolation region 258 of a sequestration pen 244. Having the length $L_{con}$ of the connection region 254 be greater than the maximum penetration depth $D_p$ of the secondary flow 262 can thus prevent contamination of one sequestration pen 244 with miscellaneous particles from the channel 122 or another sequestration pen (e.g., sequestration pens 246, 248 in FIG. 2D).

Because the channel 122 and the connection regions 254 of the sequestration pens 244, 246, 248 can be affected by the flow 260 of medium 180 in the channel 122, the channel 122 and connection regions 254 can be deemed swept (or flow) regions of the microfluidic device 240. The isolation regions 258 of the sequestration pens 244, 246, 248, on the other hand, can be deemed unswept (or non-flow) regions. For example, components (not shown) in a first fluidic medium 180 in the channel 122 can mix with a second fluidic medium 280 in the isolation region 258 substantially only by diffusion of components of the first medium 180 from the channel 122 through the connection region 254 and into the second fluidic medium 280 in the isolation region 258. Similarly, components (not shown) of the second medium 280 in the isolation region 258 can mix with the first medium 180 in the channel 122 substantially only by diffusion of components of the second medium 280 from the isolation region 258 through the connection region 254 and into the first medium 180 in the channel 122. The first medium 180 can be the same medium or a different medium than the second medium 280. Moreover, the first medium 180 and the second medium 280 can start out being the same, then become different (e.g., through conditioning of the second medium 280 by one or more cells in the isolation region 258, or by changing the medium 180 flowing through the channel 122).

The maximum penetration depth $D_p$ of the secondary flow 262 caused by the flow 260 of fluidic medium 180 in the channel 122 can depend on a number of parameters, as mentioned above. Examples of such parameters include: the shape of the channel 122 (e.g., the channel can direct medium into the connection region 254, divert medium away from the connection region 254, or direct medium in a direction substantially perpendicular to the proximal opening 252 of the connection region 254 to the channel 122); a width $W_{ch}$ (or cross-sectional area) of the channel 122 at the proximal opening 252; and a width $W_{con}$ (or cross-sectional area) of the connection region 254 at the proximal opening 252; the velocity V of the flow 260 of fluidic medium 180 in the channel 122; the viscosity of the first medium 180 and/or the second medium 280, or the like.

In some embodiments, the dimensions of the channel 122 and sequestration pens 244, 246, 248 can be oriented as follows with respect to the vector of the flow 260 of fluidic medium 180 in the channel 122; the channel width $W_{ch}$ (or cross-sectional area of the channel 122) can be substantially perpendicular to the flow 260 of medium 180; the width $W_{con}$ (or cross-sectional area) of the connection region 254 at opening 252 can be substantially parallel to the flow 260 of medium 180 in the channel 122; and/or the length $L_{con}$ of the connection region can be substantially perpendicular to the flow 260 of medium 180 in the channel 122. The foregoing are examples only, and the relative position of the channel 122 and sequestration pens 244, 246, 248 can be in other orientations with respect to each other.

As illustrated in FIG. 2E, the width $W_{con}$ of the connection region 254 can be uniform from the proximal opening 252 to the distal opening 256. The width $W_{con}$ of the connection region 254 at the distal opening 256 can thus be in any of the ranges identified herein for the width $W_{con}$ of the connection region 254 at the proximal opening 252. Alternatively, the width $W_{con}$ of the connection region 254 at the distal opening 256 can be larger than the width $W_{con}$ of the connection region 254 at the proximal opening 252.

As illustrated in FIG. 2E, the width of the isolation region 258 at the distal opening 256 can be substantially the same as the width $W_{con}$ of the connection region 254 at the proximal opening 252. The width of the isolation region 258 at the distal opening 256 can thus be in any of the ranges identified herein for the width $W_{con}$ of the connection region 254 at the proximal opening 252. Alternatively, the width of the isolation region 258 at the distal opening 256 can be larger or smaller than the width $W_{con}$ of the connection region 254 at the proximal opening 252. Moreover, the distal opening 256 may be smaller than the proximal opening 252 and the width $W_{con}$ of the connection region 254 may be narrowed between the proximal opening 252 and distal opening 256. For example, the connection region 254 may be narrowed between the proximal opening and the distal opening, using a variety of different geometries (e.g. chamfering the connection region, beveling the connection region). Further, any part or subpart of the connection region 254 may be narrowed (e.g. a portion of the connection region adjacent to the proximal opening 252).

In various embodiments of sequestration pens (e.g. 124, 126, 128, 130, 244, 246 or 248), the isolation region (e.g. 258) is configured to contain a plurality of micro-objects. In other embodiments, the isolation region can be configured to contain only one, two, three, four, five, or a similar relatively small number of micro-objects. Accordingly, the volume of an isolation region can be, for example, at least $3 \times 10^3$, $6 \times 10^3$, $9 \times 10^3$, $1 \times 10^4$, $2 \times 10^4$, $4 \times 10^4$, $8 \times 10^4$, $1 \times 10^5$, $2 \times 10^5$, $4 \times 10^5$, $8 \times 10^5$, $1 \times 10^6$, $2 \times 10^6$, $4 \times 10^6$, $6 \times 10^6$ cubic microns, or more.

In various embodiments of sequestration pens, the width $W_{ch}$ of the channel 122 at a proximal opening (e.g. 252) can be within any of the following ranges: 50-1000 microns, 50-500 microns, 50-400 microns, 50-300 microns, 50-250 microns, 50-200 microns, 50-150 microns, 50-100 microns, 70-500 microns, 70-400 microns, 70-300 microns, 70-250 microns, 70-200 microns, 70-150 microns, 90-400 microns, 90-300 microns, 90-250 microns, 90-200 microns, 90-150 microns, 100-300 microns, 100-250 microns, 100-200 microns, 100-150 microns, and 100-120 microns. The foregoing are examples only, and the width $W_{ch}$ of the channel 122 can be in other ranges (e.g., a range defined by any of the endpoints listed above). Moreover, the $W_{ch}$ of the channel 122 can be selected to be in any of these ranges in regions of the channel other than at a proximal opening of a sequestration pen.

In some embodiments, a sequestration pen has a cross-sectional height of about 30 to about 200 microns, or about 50 to about 150 microns. In some embodiments, the sequestration pen has a cross-sectional area of about 100,000 to about 2,500,000 square microns, or about 200,000 to about 2,000,000 square microns. In some embodiments, a connection region has a cross-sectional height that matches the cross-sectional height of the corresponding sequestration pen. In some embodiments, the connection region has a cross-sectional width of about 50 to about 500 microns, or about 100 to about 300 microns.

In various embodiments of sequestration pens the height $H_{ch}$ of the channel 122 at a proximal opening 252 can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{ch}$ of the channel 122 can be in other ranges (e.g., a range defined by any of the endpoints listed above). The height $H_{ch}$ of the channel 122 can be selected to be in any of these ranges in regions of the channel other than at a proximal opening of a sequestration pen.

In various embodiments of sequestration pens a cross-sectional area of the channel 122 at a proximal opening 252 can be within any of the following ranges: 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the channel 122 at a proximal opening 252 can be in other ranges (e.g., a range defined by any of the endpoints listed above).

In various embodiments of sequestration pens, the length $L_{con}$ of the connection region 254 can be in any of the following ranges: 1-200 microns, 5-150 microns, 10-100 microns, 15-80 microns, 20-60 microns, 20-500 microns, 40-400 microns, 60-300 microns, 80-200 microns, and 100-150 microns. The foregoing are examples only, and length $L_{con}$ of a connection region 254 can be in a different ranges than the foregoing examples (e.g., a range defined by any of the endpoints listed above).

In various embodiments of sequestration pens the width $W_{con}$ of a connection region 254 at a proximal opening 252 can be in any of the following ranges: 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-250 microns, 50-200 microns, 50-150 microns, 50-100 microns, 50-80 microns, 60-200 microns, 60-150 microns, 60-100 microns, 60-80 microns, 70-150 microns, 70-100 microns, and 80-100 microns. The foregoing are examples only, and the width $W_{con}$ of a connection region 254 at a proximal opening 252 can be different than the foregoing examples (e.g., a range defined by any of the endpoints listed above).

In various embodiments of sequestration pens the width $W_{con}$ of a connection region 254 at a proximal opening 252 can be in any of the following ranges: 2-35 microns, 2-25 microns, 2-20 microns, 2-15 microns, 2-10 microns, 2-7 microns, 2-5 microns, 2-3 microns, 3-25 microns, 3-20 microns, 3-15 microns, 3-10 microns, 3-7 microns, 3-5 microns, 3-4 microns, 4-20 microns, 4-15 microns, 4-10 microns, 4-7 microns, 4-5 microns, 5-15 microns, 5-10 microns, 5-7 microns, 6-15 microns, 6-10 microns, 6-7 microns, 7-15 microns, 7-10 microns, 8-15 microns, and 8-10 microns. The foregoing are examples only and the width $W_{con}$ of a connection region 254 at a proximal opening 252 can be different than the foregoing examples (e.g., a range defined by any of the endpoints listed above).

In various embodiments of sequestration pens, a ratio of the length Lon of a connection region 254 to a width $W_{con}$ con of the connection region 254 at the proximal opening 252 can be greater than or equal to any of the following ratios: 0.5, 1.0, 1.5, 2.0, 2.5, 3.0, 3.5, 4.0, 4.5, 5.0, 6.0, 7.0, 8.0, 9.0, 10.0, or more. The foregoing are examples only, and the ratio of the length $L_{con}$ of a connection region 254 to a width $W_{con}$ of the connection region 254 at the proximal opening 252 can be different than the foregoing examples.

In various embodiments of microfluidic devices 100, 200, 240, 290, $V_{max}$ can be set around 0.2, 0.3, 0.4, 0.5, 0.6, 0.7, 0.8, 0.9, 1.0, 1.1, 1.2, 1.3, 1.4, or 1.5 µL/sec.

In various embodiments of microfluidic devices having sequestration pens, the volume of an isolation region 258 of a sequestration pen can be, for example, at least $3 \times 10^3$, $6 \times 10^3$, $9 \times 10^3$, $1 \times 10^4$, $2 \times 10^4$, $4 \times 10^4$, $8 \times 10^4$, $1 \times 10^5$, $2 \times 10^5$, $4 \times 10^5$, $8 \times 10^5$, $1 \times 10^6$, $2 \times 10^6$, $4 \times 10^6$, $6 \times 10^6$ cubic microns, or more. In various embodiments of microfluidic devices having sequestration pens, the volume of a sequestration pen may be about $5 \times 10^3$, $7 \times 10^3$, $1 \times 10^4$, $3 \times 10^4$, $5 \times 10^4$, $8 \times 10^4$, $1 \times 10^5$, $2 \times 10^5$, $4 \times 10^5$, $6 \times 10^5$, $8 \times 10^5$, $1 \times 10^6$, $2 \times 10^6$, $4 \times 10^6$, $8 \times 10^6$, $1 \times 10^7$, $3 \times 10^7$, $5 \times 10^7$, or about $8 \times 10^7$ cubic microns, or more. In some embodiments, the microfluidic device has sequestration pens wherein no more than $1 \times 10^2$ biological cells may be maintained, and the volume of a sequestration pen may be no more than $2 \times 10^6$ cubic microns. In some embodiments, the microfluidic device has sequestration pens wherein no more than $1 \times 10^2$ biological cells may be maintained, and a sequestration pen may be no more than $4 \times 10^5$ cubic microns. In yet other embodiments, the microfluidic device has sequestration pens wherein no more than 50 biological cells may be maintained, a sequestration pen may be no more than $4 \times 10^5$ cubic microns.

In various embodiment, the microfluidic device has sequestration pens configured as in any of the embodiments discussed herein where the microfluidic device has about 100 to about 500 sequestration pens; about 200 to about 1000 sequestration pens, about 500 to about 1500 sequestration pens, about 1000 to about 2000 sequestration pens, or about 1000 to about 3500 sequestration pens.

In some other embodiments, the microfluidic device has sequestration pens configured as in any of the embodiments discussed herein where the microfluidic device has about 1500 to about 3000 sequestration pens, about 2000 to about 3500 sequestration pens, about 2500 to about 4000 sequestration pens, about 3000 to about 4500 sequestration pens, about 3500 to about 5000 sequestration pens, about 4000 to about 5500 sequestration pens, about 4500 to about 6000 sequestration pens, about 5000 to about 6500 sequestration pens, about 5500 to about 7000 sequestration pens, about 6000 to about 7500 sequestration pens, about 6500 to about 8000 sequestration pens, about 7000 to about 8500 sequestration pens, about 7500 to about 9000 sequestration pens, about 8000 to about 9500 sequestration pens, about 8500 to about 10,000 sequestration pens, about 9000 to about 10,500 sequestration pens, about 9500 to about 11,000 sequestration pens, about 10,000 to about 11,500 sequestration pens, about 10,500 to about 12,000 sequestration pens, about 11,000 to about 12,500 sequestration pens, about 11,500 to about 13,000 sequestration pens, about 12,000 to about 13,500 sequestration pens, about 12,500 to about 14,000 sequestration pens, about 13,000 to about 14,500 sequestration pens, about 13,500 to about 15,000 sequestration pens, about 14,000 to about 15,500 sequestration pens, about 14,500 to about 16,000 sequestration pens, about 15,000 to about 16,500 sequestration pens, about 15,500 to about 17,000 sequestration pens, about 16,000 to about 17,500 sequestration pens, about 16,500 to about 18,000 sequestration pens, about 17,000 to about 18,500 sequestration pens, about 17,500 to about 19,000 sequestration pens, about 18,000 to about 19,500 sequestration pens, about 18,500 to about 20,000 sequestration pens, about 19,000 to about 20,500 sequestration pens, about 19,500 to about 21,000 sequestration pens, or about 20,000 to about 21,500 sequestration pens.

Figure 2F:
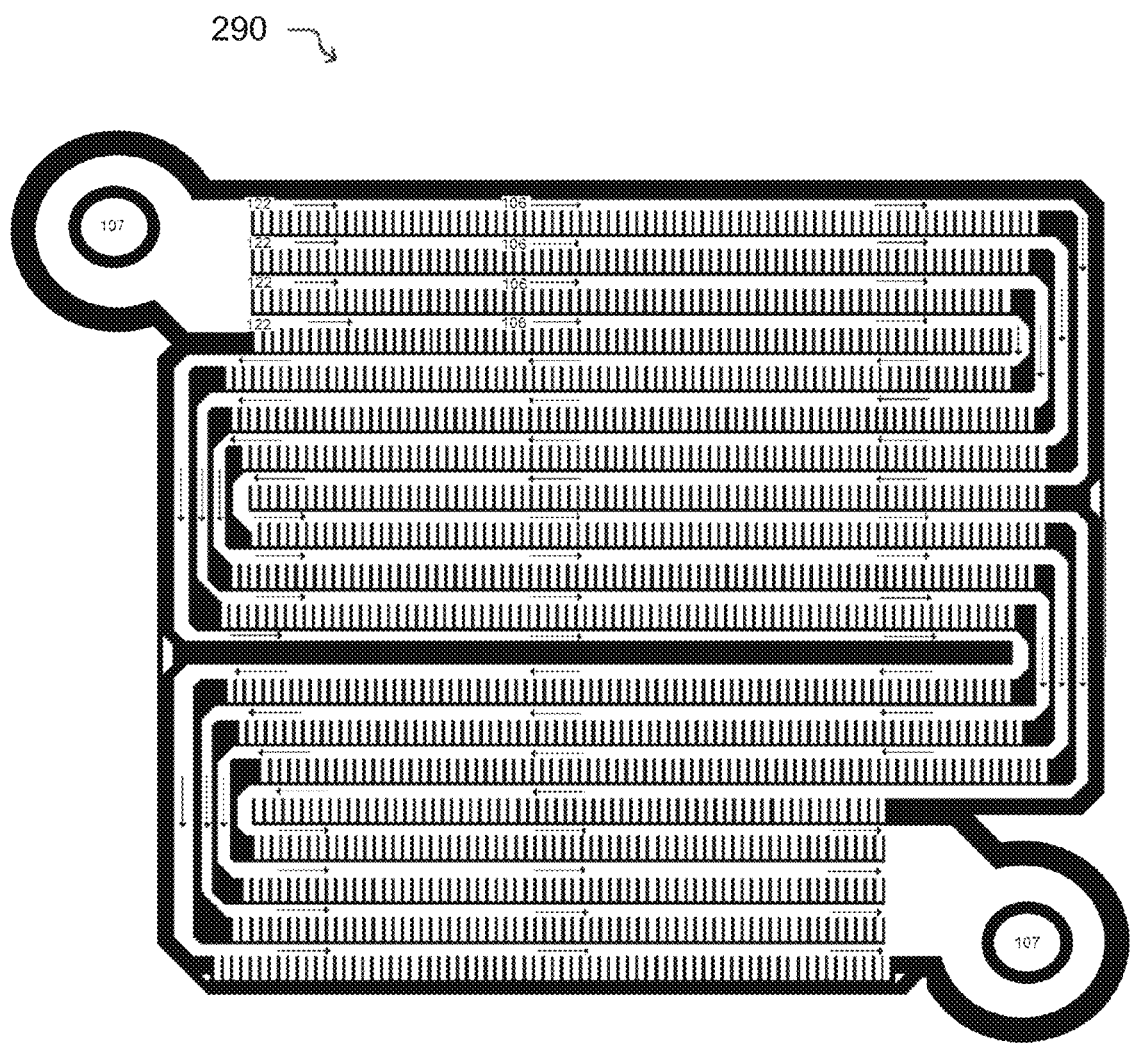
FIG. 2F illustrates a microfluidic device according to an embodiment of the invention.

FIG. 2F illustrates a microfluidic device 290 according to one embodiment. The microfluidic device 290 is illustrated in FIG. 2F is a stylized diagram of a microfluidic device 100. In practice the microfluidic device 290 and its constituent circuit elements (e.g. channels 122 and sequestration pens 128) would have the dimensions discussed herein. The microfluidic circuit 120 illustrated in FIG. 2F has two ports 107, four distinct channels 122 and four distinct flow paths 106. The microfluidic device 290 further comprises a plurality of sequestration pens opening off of each channel 122. In the microfluidic device illustrated in FIG. 2F, the sequestration pens have a geometry similar to the pens illustrated in FIG. 2E and thus, have both connection regions and isolation regions. Accordingly, the microfluidic circuit 120 includes both swept regions (e.g. channels 122 and portions of the connection regions 254 within the maximum penetration depth $D_p$ of the secondary flow 262) and non-swept regions (e.g. isolation regions 258 and portions of the connection regions 254 not within the maximum penetration depth $D_p$ of the secondary flow 262).

Figure 3A:
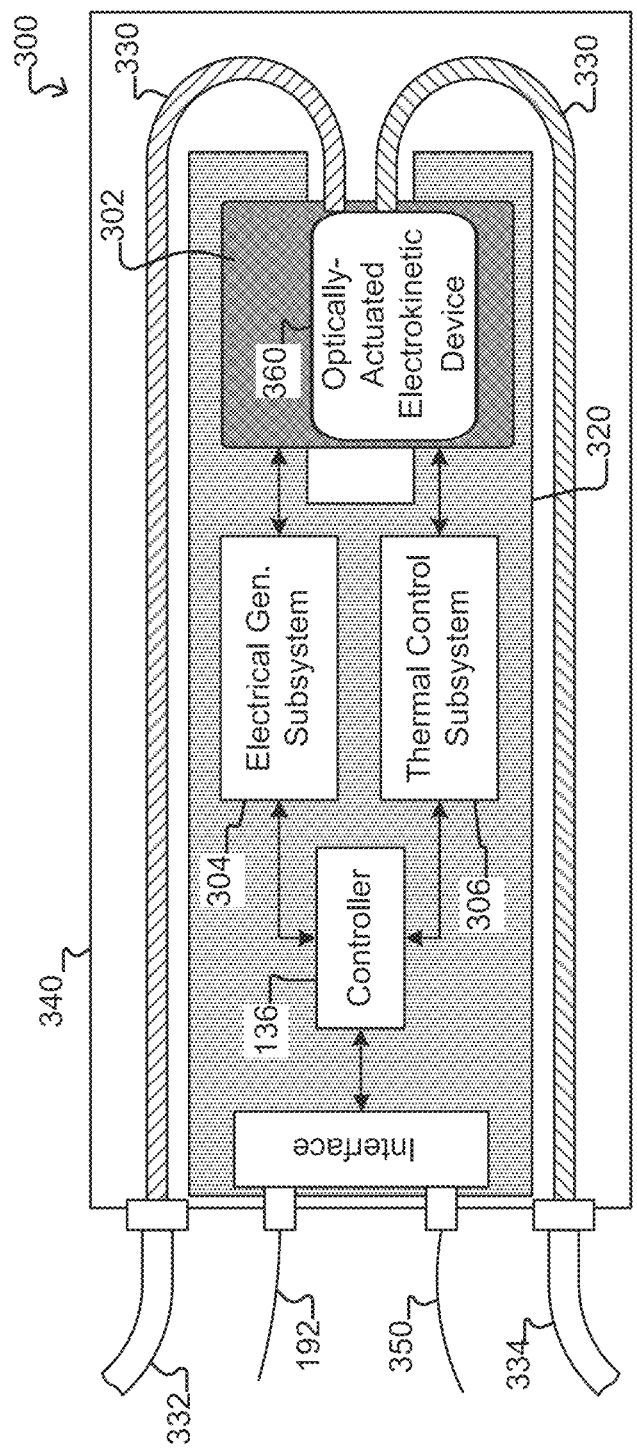
FIG. 3A illustrates a specific example of a system for use with a microfluidic device and associated control equipment according to some embodiments of the invention.
Figure 3B:
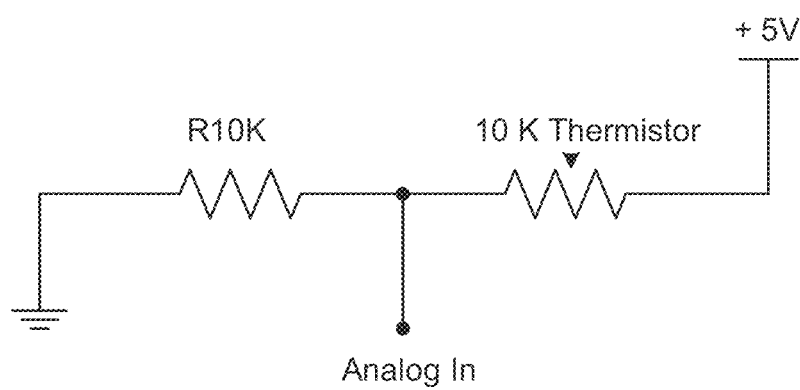
FIG. 3B illustrates an exemplary analog voltage divider circuit according to some embodiments of the invention.

FIGS. 3A through 3D shows various embodiments of system 150 which can be used to operate and observe microfluidic devices (e.g. 100, 200, 240, 290) according to the present invention. As illustrated in FIG. 3A, the system 150 can include a structure ("nest") 300 configured to hold a microfluidic device 100 (not shown), or any other microfluidic device described herein. The nest 300 can include a socket 302 capable of interfacing with the microfluidic device 360 (e.g., an optically-actuated electrokinetic device 100) and providing electrical connections from power source 192 to microfluidic device 360. The nest 300 can further include an integrated electrical signal generation subsystem 304. The electrical signal generation subsystem 304 can be configured to supply a biasing voltage to socket 302 such that the biasing voltage is applied across a pair of electrodes in the microfluidic device 360 when it is being held by socket 302. Thus, the electrical signal generation subsystem 304 can be part of power source 192. The ability to apply a biasing voltage to microfluidic device 360 does not mean that a biasing voltage will be applied at all times when the microfluidic device 360 is held by the socket 302. Rather, in most cases, the biasing voltage will be applied intermittently, e.g., only as needed to facilitate the generation of electrokinetic forces, such as dielectrophoresis or electro-wetting, in the microfluidic device 360.

As illustrated in FIG. 3A, the nest 300 can include a printed circuit board assembly (PCBA) 320. The electrical signal generation subsystem 304 can be mounted on and electrically integrated into the PCBA 320. The exemplary support includes socket 302 mounted on PCBA 320, as well.

Typically, the electrical signal generation subsystem 304 will include a waveform generator (not shown). The electrical signal generation subsystem 304 can further include an oscilloscope (not shown) and/or a waveform amplification circuit (not shown) configured to amplify a waveform received from the waveform generator. The oscilloscope, if present, can be configured to measure the waveform supplied to the microfluidic device 360 held by the socket 302. In certain embodiments, the oscilloscope measures the waveform at a location proximal to the microfluidic device 360 (and distal to the waveform generator), thus ensuring greater accuracy in measuring the waveform actually applied to the device. Data obtained from the oscilloscope measurement can be, for example, provided as feedback to the waveform generator, and the waveform generator can be configured to adjust its output based on such feedback. An example of a suitable combined waveform generator and oscilloscope is the Red Pitaya™.

In certain embodiments, the nest 300 further comprises a controller 308, such as a microprocessor used to sense and/or control the electrical signal generation subsystem 304. Examples of suitable microprocessors include the Arduino™ microprocessors, such as the Arduino Nano™. The controller 308 may be used to perform functions and analysis or may communicate with an external master controller 154 (shown in FIG. 1) to perform functions and analysis. In the embodiment illustrated in FIG. 3A the controller 308 communicates with a master controller 154 through an interface 310 (e.g., a plug or connector).

In some embodiments, the nest 300 can comprise an electrical signal generation subsystem 304 comprising a Red Pitaya™ waveform generator/oscilloscope unit ("Red Pitaya™ unit") and a waveform amplification circuit that amplifies the waveform generated by the Red Pitaya™ unit and passes the amplified voltage to the microfluidic device 100. In some embodiments, the Red Pitaya™ unit is configured to measure the amplified voltage at the microfluidic device 360 and then adjust its own output voltage as needed such that the measured voltage at the microfluidic device 360 is the desired value. In some embodiments, the waveform amplification circuit can have a +6.5V to –6.5V power supply generated by a pair of DC-DC converters mounted on the PCBA 320, resulting in a signal of up to 13 Vpp at the microfluidic device 360.

As illustrated in FIG. 3A, the nest 300 can further include a thermal control subsystem 306. The thermal control subsystem 306 can be configured to regulate the temperature of microfluidic device 360 held by the support structure 300. For example, the thermal control subsystem 306 can include a Peltier thermoelectric device (not shown) and a cooling unit (not shown). The Peltier thermoelectric device can have a first surface configured to interface with at least one surface of the microfluidic device 360. The cooling unit can be, for example, a cooling block (not shown), such as a liquid-cooled aluminum block. A second surface of the Peltier thermoelectric device (e.g., a surface opposite the first surface) can be configured to interface with a surface of such a cooling block. The cooling block can be connected to a fluidic path 330 configured to circulate cooled fluid through the cooling block. In the embodiment illustrated in FIG. 3A, the support structure 300 comprises an inlet 332 and an outlet 334 to receive cooled fluid from an external reservoir (not shown), introduce the cooled fluid into the fluidic path 330 and through the cooling block, and then return the cooled fluid to the external reservoir. In some embodiments, the Peltier thermoelectric device, the cooling unit, and/or the fluidic path 330 can be mounted on a casing 340 of the support structure 300. In some embodiments, the thermal control subsystem 306 is configured to regulate the temperature of the Peltier thermoelectric device so as to achieve a target temperature for the microfluidic device 360. Temperature regulation of the Peltier thermoelectric device can be achieved, for example, by a thermoelectric power supply, such as a Pololu™ thermoelectric power supply (Pololu Robotics and Electronics Corp.). The thermal control subsystem 306 can include a feedback circuit, such as a temperature value provided by an analog circuit. Alternatively, the feedback circuit can be provided by a digital circuit.

In some embodiments, the nest 300 can include a thermal control subsystem 306 with a feedback circuit that is an analog voltage divider circuit (shown in FIG. 3B) which includes a resistor (e.g., with resistance 1 kOhm+/–0.1%, temperature coefficient+/–0.02 ppm/C0) and a NTC thermistor (e.g., with nominal resistance 1 kOhm+/–0.01%). In some instances, the thermal control subsystem 306 measures the voltage from the feedback circuit and then uses the calculated temperature value as input to an on-board PID control loop algorithm. Output from the PID control loop algorithm can drive, for example, both a directional and a pulse-width-modulated signal pin on a Pololu™ motor drive (not shown) to actuate the thermoelectric power supply, thereby controlling the Peltier thermoelectric device.

Figure 3C:
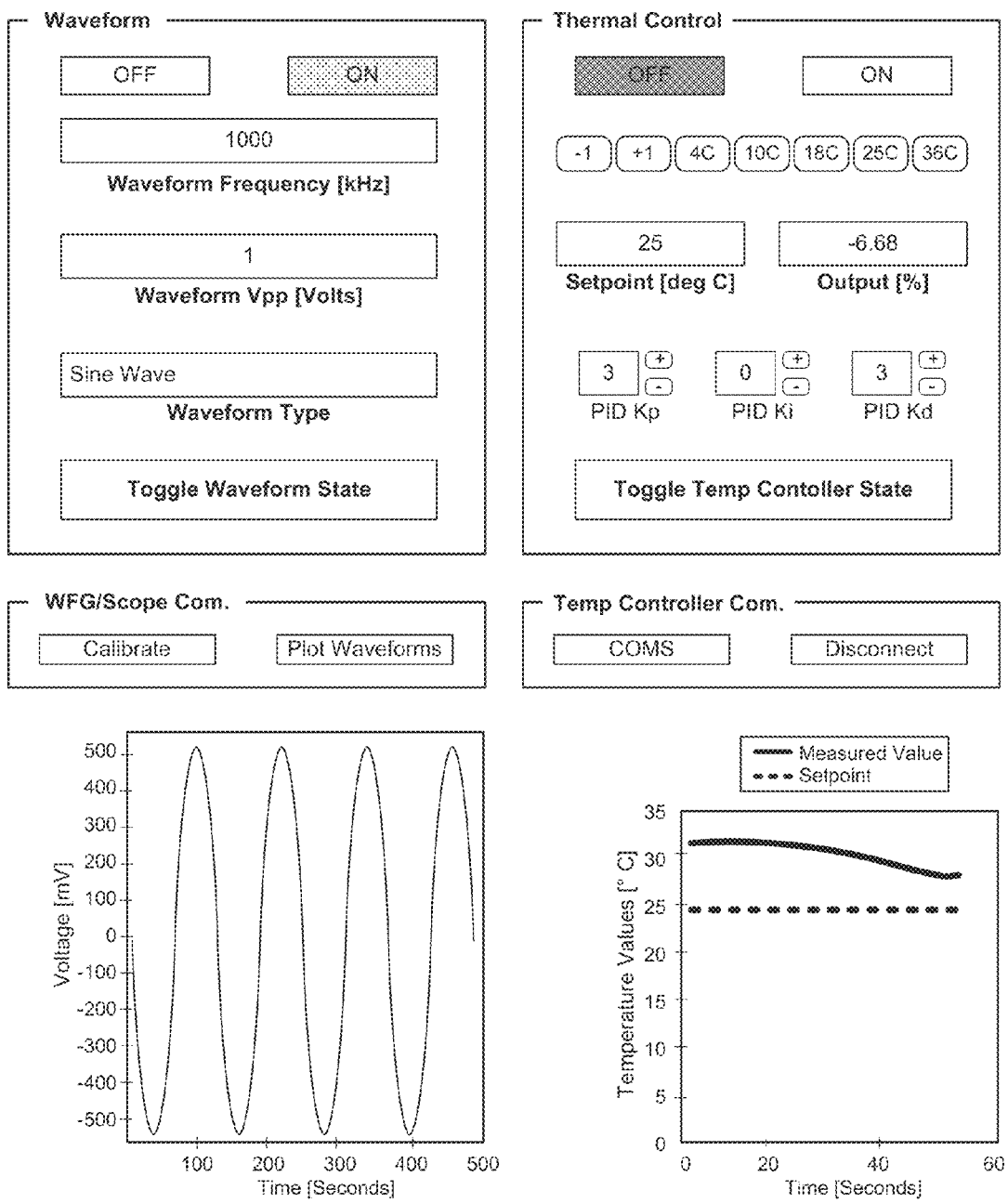
FIG. 3C illustrates an exemplary GUI configured to plot temperature and waveform data according to some embodiments of the invention.

The nest 300 can include a serial port 350 which allows the microprocessor of the controller 308 to communicate with an external master controller 154 via the interface 310. In addition, the microprocessor of the controller 308 can communicate (e.g., via a Plink tool (not shown)) with the electrical signal generation subsystem 304 and thermal control subsystem 306. Thus, via the combination of the controller 308, the interface 310, and the serial port 350, the electrical signal generation subsystem 308 and the thermal control subsystem 306 can communicate with the external master controller 154. In this manner, the master controller 154 can, among other things, assist the electrical signal generation subsystem 308 by performing scaling calculations for output voltage adjustments. A Graphical User Interface (GUI), one example of which is shown in FIG. 3C, provided via a display device 170 coupled to the external master controller 154, can be configured to plot temperature and waveform data obtained from the thermal control subsystem 306 and the electrical signal generation subsystem 308, respectively. Alternatively, or in addition, the GUI can allow for updates to the controller 308, the thermal control subsystem 306, and the electrical signal generation subsystem 304.

As discussed above, system 150 can include an imaging device 194. In some embodiments, the imaging device 194 comprises a light modulating subsystem 404. The light modulating subsystem 404 can include a digital mirror device (DMD) or a microshutter array system (MSA), either of which can be configured to receive light from a light source 402 and transmits a subset of the received light into an optical train of microscope 400. Alternatively, the light modulating subsystem 404 can include a device that produces its own light (and thus dispenses with the need for a light source 402), such as an organic light emitting diode display (OLED), a liquid crystal on silicon (LCOS) device, a ferroelectric liquid crystal on silicon device (FLCOS), or a transmissive liquid crystal display (LCD). The light modulating subsystem 404 can be, for example, a projector. Thus, the light modulating subsystem 404 can be capable of emitting both structured and unstructured light. One example of a suitable light modulating subsystem 404 is the Mosaic™ system from Andor Technologies™. In certain embodiments, imaging module 164 and/or motive module 162 of system 150 can control the light modulating subsystem 404.

In certain embodiments, the imaging device 194 further comprises a microscope 400. In such embodiments, the nest 300 and light modulating subsystem 404 can be individually configured to be mounted on the microscope 400. The microscope 400 can be, for example, a standard research-grade light microscope or fluorescence microscope. Thus, the nest 300 can be configured to be mounted on the stage 410 of the microscope 400 and/or the light modulating subsystem 404 can be configured to mount on a port of microscope 400. In other embodiments, the nest 300 and the light modulating subsystem 404 described herein can be integral components of microscope 400.

In certain embodiments, the microscope 400 can further include one or more detectors 422. In some embodiments, the detector 422 is controlled by the imaging module 164. The detector 422 can include an eye piece, a charge-coupled device (CCD), a camera (e.g., a digital camera), or any combination thereof. If at least two detectors 422 are present, one detector can be, for example, a fast-frame-rate camera while the other detector can be a high sensitivity camera. Furthermore, the microscope 400 can include an optical train configured to receive reflected and/or emitted light from the microfluidic device 360 and focus at least a portion of the reflected and/or emitted light on the one or more detectors 422. The optical train of the microscope can also include different tube lenses (not shown) for the different detectors, such that the final magnification on each detector can be different.

In certain embodiments, imaging device 194 is configured to use at least two light sources. For example, a first light source 402 can be used to produce structured light (e.g., via the light modulating subsystem 404) and a second light source 432 can be used to provide unstructured light. The first light source 402 can produce structured light for optically-actuated electrokinesis and/or fluorescent excitation, and the second light source 432 can be used to provide bright field illumination. In these embodiments, the motive module 162 can be used to control the first light source 404 and the imaging module 164 can be used to control the second light source 432. The optical train of the microscope 400 can be configured to (1) receive structured light from the light modulating subsystem 404 and focus the structured light on at least a first region in a microfluidic device, such as an optically-actuated electrokinetic device, when the device is being held by the support structure 200, and (2) receive reflected and/or emitted light from the microfluidic device and focus at least a portion of such reflected and/or emitted light onto detector 422. The optical train can be further configured to receive unstructured light from a second light source and focus the unstructured light on at least a second region of the microfluidic device, when the device is held by the support structure 300. In certain embodiments, the first and second regions of the microfluidic device can be overlapping regions. For example, the first region can be a subset of the second region.

Figure 3D:
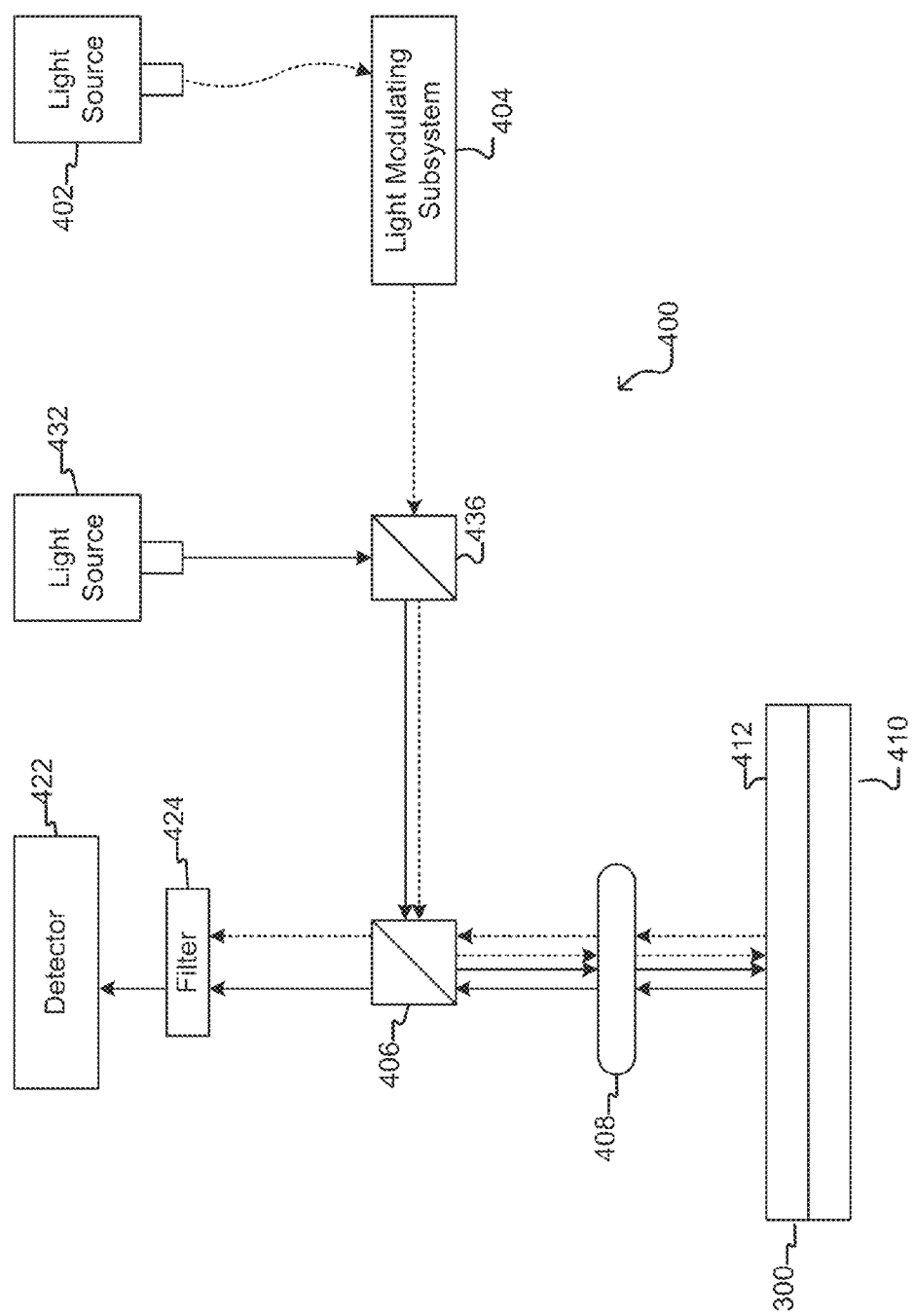
FIG. 3D illustrates an imaging device according to some embodiments of the invention.

In FIG. 3D, the first light source 402 is shown supplying light to a light modulating subsystem 404, which provides structured light to the optical train of the microscope 400. The second light source 432 is shown providing unstructured light to the optical train via a beam splitter 436. Structured light from the light modulating subsystem 404 and unstructured light from the second light source 432 travel from the beam splitter 436 through the optical train together to reach a second beam splitter (or dichroic filter 406, depending on the light provided by the light modulating subsystem 404) where the light gets reflected down through the objective 408 to the sample plane 412. Reflected and/or emitted light from the sample plane 412 then travels back up through the objective 408, through the beam splitter and/or dichroic filter 406, and to another dichroic filter 424. Only a fraction of the light reaching dichroic filter 424 passes through and reaches the detector 422.

In some embodiments, the second light source 432 emits blue light. With an appropriate dichroic filter 424, blue light reflected from the sample plane 412 is able to pass through dichroic filter 424 and reach the detector 422. In contrast, structured light coming from the light modulating subsystem 404 gets reflected from the sample plane 412, but does not pass through the dichroic filter 424. In this example, the dichroic filter 424 is filtering out visible light having a wavelength longer than 495 nm. Such filtering out of the light from the light modulating subsystem 404 would only be complete (as shown) if the light emitted from the light modulating subsystem did not include any wavelengths shorter than 495 nm. In practice, if the light coming from the light modulating subsystem 404 includes wavelengths shorter than 495 nm (e.g., blue wavelengths), then some of the light from the light modulating subsystem would pass through filter 424 to reach the detector 422. In such an embodiment, the filter 424 acts to change the balance between the amount of light that reaches the detector 422 from the first light source 402 and the second light source 432. This can be beneficial if the first light source 402 is significantly stronger than the second light source 432. In other embodiments, the second light source 432 can emit red light, and the dichroic filter 424 can filter out visible light other than red light (e.g., visible light having a wavelength shorter than 650 nm).

Figure 3E:
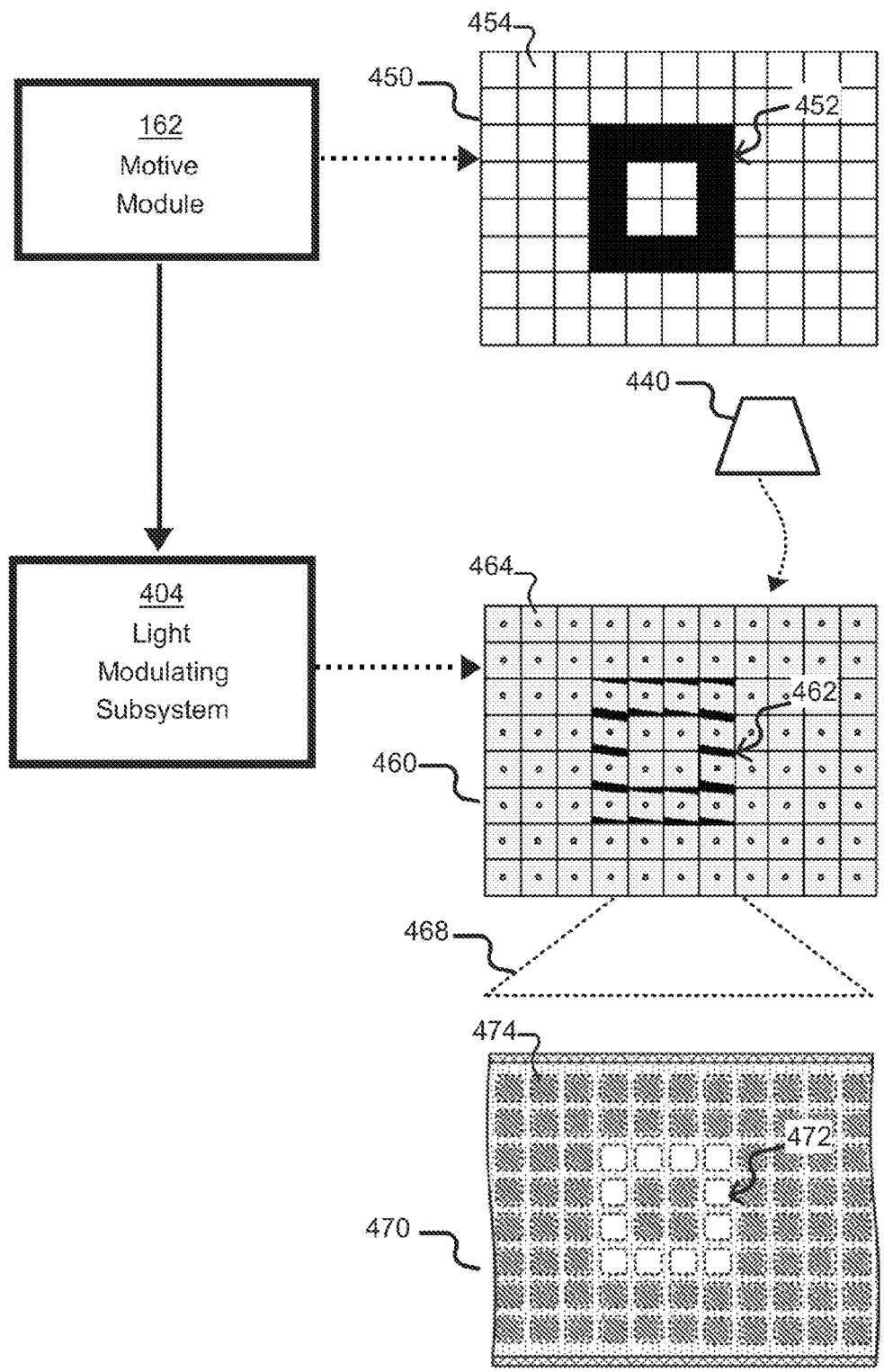
FIG. 3E illustrates communications between a motive module and a light modulating subsystem that control the projection of patterns of light on a microfluidic device, according to a specific embodiment of the invention.

FIG. 3E illustrates communications between the motive module 164 and the light modulating subsystem 404 to project patterns of light on a microfluidic device according to a specific embodiment of the invention. As discussed above with respect to FIG. 3D, the light modulating subsystem 404 may comprise an electrically-addressed spatial light modulator and/or an optically-addressed spatial light modulator. Electrically-addressed spatial light modulators (i.e. spatial light modulating elements) comprise an array of individually-addressable spatial light modulators that are controlled by electrodes. In FIG. 3E, the light modulating subsystem 404 is a Digital Mirror Device (DMD) 460 comprising an array of individually-addressable micro-mirrors 464 that are controlled by an electrodes. However, in other embodiments, the light modulating subsystem 404 can be a Liquid Crystal on Silicon (LCoS) device comprising an array of individually-addressable electrodes that correspond to pixels in a liquid crystal display.

In the embodiment illustrated in FIG. 3E, the light modulating subsystem 404 uses a separate light source 440 to receive and modulate light. However, in other embodiments, the light modulating subsystem 404 comprises its own light source.

As illustrated in FIG. 3E, the motive module 162 transmits information 450 specifying a specific pattern of light ("pattern information") to the light modulating subsystem 404. In some embodiments, the pattern information 450 can comprise a bitmap (or similar pixel-based data structure), vector data, or any combination thereof. For purposes of illustration, the pattern information 450 in FIG. 3E is illustrated as a bitmap comprising an array of pixels 454 and including a square pattern 452 of pixels. Depending on the embodiment, the pattern information 450 can be binary (i.e. specify whether or not to project a pattern of light) or contain values indicating an intensity of light to project. In instances where the spatial light modulators are micro-mirrors 464, the micro-mirrors 464 may create different intensities of light by rapidly switching the mirrors between an "on" and "off" state (i.e. "dithering" the micro-mirrors).

The light modulating subsystem 404 receives the pattern information 450 from the motive module 162 and uses the pattern information 450 to direct the projection of a pattern of light 468 onto DEP electrode regions 474 on the microfluidic device 470. In the embodiment illustrated in FIG. 3E, a DMD 460 rotates a plurality 462 of individually-addressable micro-mirrors 464 corresponding to the square pattern information 450 into an "on state." The square pattern of individual-addressable micro-mirrors 462 modulates the light from the light source 440 to project a pattern of light 468 onto the microfluidic device 470 that illuminates a square pattern of DEP electrode regions 472 in the array of DEP electrode regions 474 in the microfluidic device 470.

In some embodiments, there is a one-to-one correspondence between the array of individually-addressable spatial light modulating elements 464 that project light onto the microfluidic device 470 and the array of DEP electrode regions 474 in the microfluidic device 470. In this way, each individually-addressable spatial light modulating element 464 can project light to generate light-actuated DEP force at a corresponding DEP electrode region 474. In these embodiments, the motive module 162 can send pattern information 450 to the light modulating subsystem 404 that specifies the DEP electrode regions 474 to project light onto. For example, instead of sending bitmap and or vector data to the light modulating subsystem 404, the motive module 162 can communicate directly with the individually-addressable spatial light modulators to control which of the DEP electrode regions 474 are illuminated on the microfluidic device 470. Once illuminated the DEP electrode regions 474 may exert OET or OEW force on surrounding micro-objects.

As discussed above, in some embodiments, the spatial light modulating elements 464 can receive pattern information 450 specifying an intensity of light to project. In a specific embodiment, the pattern information 450 may specify a gradation of light to project over adjacent DEP electrode regions 474 in the microfluidic device. In some embodiments, the pattern information 450 may specify a gradation of light that decreases in intensity over adjacent DEP electrode regions 474. For example, the pattern information 450 may specify that about 100% of the maximum light intensity is to be projected at a first DEP electrode region 474, that 70% of the maximum light intensity is to be projected at a second DEP electrode region 474 adjacent to the first DEP electrode region 474, and that 10% of the maximum light intensity is to be projected at a third DEP electrode region 474 adjacent to the second DEP electrode region 474. Various combinations of light intensities may be used to project a gradation over various numbers of DEP electrode regions 474 (e.g. any decreasing combination of about 100%, about 90%, about 80%, about 70%, about 60%, about 50%, about 40%, about 30%, about 20%, and about 10%, and any values therebetween, of the maximum light intensity over any number of DEP electrode regions 474 and). Similarly, the pattern information 450 may specify a gradation of light that increases in intensity over any number of DEP electrode regions 474 or a gradation of light that both increases and decreases in intensity over any number of DEP electrode regions 474.

Use of Gravitational Force to Manipulate Micro-Objects in a Microfluidic Device.

Figure 4A:
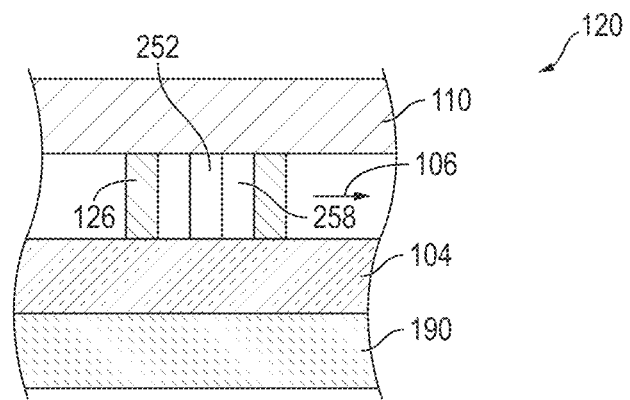
FIGS. 4A-4H provide various cross-section, schematic views of a microfluidic device having a microfluidic channel and a sequestration pen, and a process by which a target micro-object is trapped and transferred to the sequestration pen according to some embodiments of the invention.
Figure 4B:
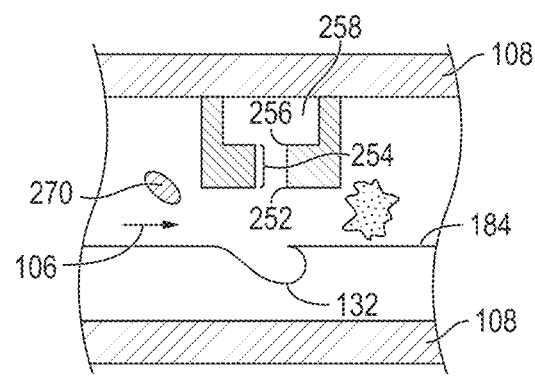

Referring now to FIGS. 4A-4H, a schematic representation of a method for capturing a targeted micro-object 270 using a tilting device 190 according to the present invention is shown. FIG. 4A is a cross-sectional side view of a sequestration pen 126 and flow path 106 of the microfluidic circuit 120, and FIG. 4B is a cross-sectional top view of the microfluidic circuit 120 of FIG. 4A. The sequestration pen 126 can comprises an isolation region 258, as shown, and the isolation region can have a volume sufficient to capture and retain at least one target micro-object 270. Sequestration pen 126 can further comprise a connection region 254 fluidically connecting isolation region 258 to flow path 106.

In some instances, isolation region 258 comprises a volume that is approximately equal to the volume of a single target micro-object 270. For example, the isolation region 258 can have a length (e.g., depth) of about 10 microns to about 25 microns. In some embodiments, isolation region 258 has a length of about 1-5 microns, 5-15 microns, 15-25 microns, 20-40 microns, 30-50 microns, 50-100 microns, or 100-150 microns. In some embodiments, isolation region 258 comprises a volume from approximately 1000 $\mu m^3$ to approximately 10,000 $\mu m^3$. In some embodiments, isolation region 258 comprises a volume of about 1000-5000 $\mu m^3$, 5000-10,000 $\mu m^3$, 10,000-15,000 $\mu m^3$, 10,000-20,000 $\mu m^3$, 15,000-30,000 $\mu m^3$, or 20,000-30,000 $\mu m^3$.

In some instances, connection region 254 comprises a width that is sufficiently reduced so as to prevent two or more target micro-objects 270 from moving side-by-side through proximal opening 252 and into isolation region 258. In some instances, connection region 254 comprises a constriction which reduces the width of at least a portion of connection region 254 so as to substantially prevent two target micro-objects from moving side-by-side though the constriction. Further, in some instances at least one of the connection region 254 and the proximal opening 252 comprises an obstruction which reduces the size of the region or opening so as to substantially prevent two target micro-objects from moving side-by-side through the opening. In some instances, sequestration pen 126 comprises a constriction having a width that is smaller than twice the diameter of a target micro-object 270.

In some instances, distal opening 256 comprises a constriction having a cross-sectional area of about 20-50 $\mu m^2$, 25-75 $\mu m^2$, 50-100 $\mu m^2$, 75-125 $\mu m^2$, 100-150 $\mu m^2$, 125-200 $\mu m^2$, 150-250 $\mu m^2$, 200-300 $\mu m^2$, 250-350 $\mu m^2$, 300-450 $\mu m^2$, 400-600 $\mu m^2$, 500-700 $\mu m^2$, 600-750 $\mu m^2$, 700-850 $\mu m^2$, 750-900 $\mu m^2$, 800-1000 $\mu m^2$, 900-1250 $\mu m^2$, 1000-1500 $\mu m^2$, 1250-1750 $\mu m^2$, 1500-2000 $\mu m^2$, 1750-2250 $\mu m^2$, 2000-2500 $\mu m^2$, 2250-2750 $\mu m^2$, 2500-3000 $\mu m^2$, 2750-3250 $\mu m^2$, 3000-3500 $\mu m^2$, 3250-3750 $\mu m^2$, 3500-4000 $\mu m^2$, 3750-4250 $\mu m^2$, 4000-4500 $\mu m^2$, 4250-4750 $\mu m^2$, or 4500-5000 $\mu m^2$. In some instances, sequestration pen 126 comprises a constriction having a width of about 20 microns.

In some embodiments, a distal portion of connection region 254 comprises a reduced width. For example, the distal portion of connection region 254 can have a width that is about 20%, 30%, 40%, 50%, 60%, 70%, 80%, 90% of the width of the proximal portion of the connection region 254. In some instances, the distal opening 256 comprises a reduced width that is equal to the reduced width of the distal portion of connection region 254. In some instances, distal opening 256 comprises at least a portion of the distal portion of connection region 254. In some instances, the distal portion of connection region 254 having the reduced width comprises a cross-sectional area of about 20-50 $\mu m^2$, 25-75 $\mu m^2$, 50-100 $\mu m^2$, 75-125 $\mu m^2$, 100-150 $\mu m^2$, 125-200 $\mu m^2$, 150-250 $\mu m^2$, 200-300 $\mu m^2$, 250-350 $\mu m^2$, 300-450 $\mu m^2$, 400-600 $\mu m^2$, 500-700 $\mu m^2$, 600-750 $\mu m^2$, 700-850 $\mu m^2$, 750-900 $\mu m^2$, 800-1000 $\mu m^2$, 900-1250 $\mu m^2$, 1000-1500 $\mu m^2$, 1250-1750 $\mu m^2$, 1500-2000 $\mu m^2$, 1750-2250 $\mu m^2$, 2000-2500 $\mu m^2$, 2250-2750 $\mu m^2$, 2500-3000 $\mu m^2$, 2750-3250 $\mu m^2$, 3000-3500 $\mu m^2$, 3250-3750 $\mu m^2$, 3500-4000 $\mu m^2$, 3750-4250 $\mu m^2$, 4000-4500 $\mu m^2$, 4250-4750 $\mu m^2$, or 4500-5000 $\mu m^2$.

In some embodiments, at least one of the distal opening 256 and the connection region 254 comprise a width of less than about 50, 40, 30, 25, 20 or 15 microns, or less. In some embodiments, distal opening 256 and/or connection region 254 comprise a width from 1 to 5 microns, from 1 to 10 microns, from 5 to 10 microns, from 5 to 15 microns, from 5 to 20 microns, from 10 to 15 microns, from 10 to 20 microns, from 10 to 25 microns, from 10 to 30 microns, from 15 to 20 microns, from 15 to 25 microns, from 15 to 30 microns, from 15 to 35 microns, from 20 to 25 microns, from 20 to 30 microns, from 20 to 35 microns, from 20 to 40 microns, from 25 to 40 microns, from 25 to 50 microns, from 40 to 80 microns, from 50 to 100 microns, from 80 to 125 microns, and from 100 to 150 microns.

Generally, the proximal opening 252 is perpendicular to the flow path 106 in the channel 122 such that the flow of medium 180 (and micro-objects therein) is not directed into the proximal opening 252, and thus into sequestration pen 126. In some embodiments, microfluidic circuit 120 comprises a micro-object trap 132 that is positioned in the flow path 106, such as at the periphery of channel 122. The micro-object trap 132 may be opposite a sequestration pen 126, either in a wall as illustrated in FIG. 4B or in a free-standing structure. Unlike the proximal opening 252, the trap 132 can comprise an upstream opening that is configured to encourage the reception of one or more target micro-objects. In some instances, the trap 132 can comprise a volume approximately equal to at least the volume of a single target micro-object. In other instances, trap 132 comprises a volume of about 2, 3, 4, 5 times, or more, the volume of a single target micro-object.

Figure 4C:
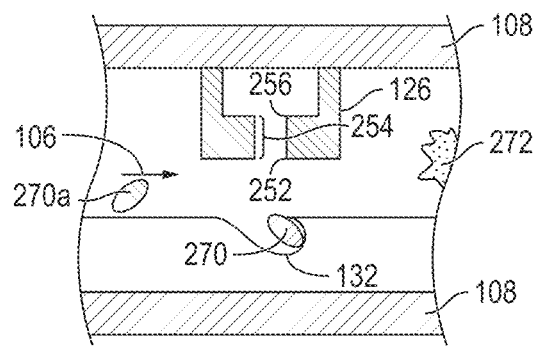
Figure 4D:
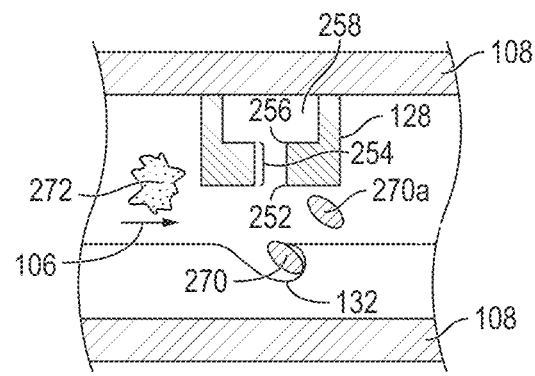
Figure 4E:
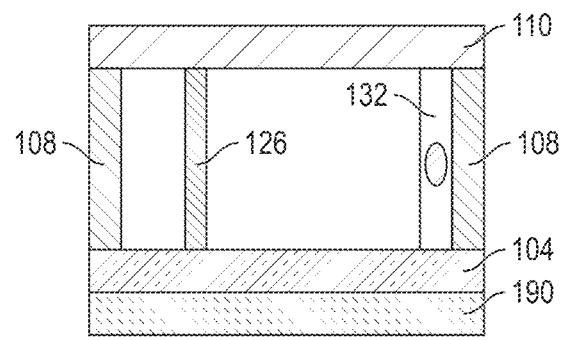
Figure 4F:
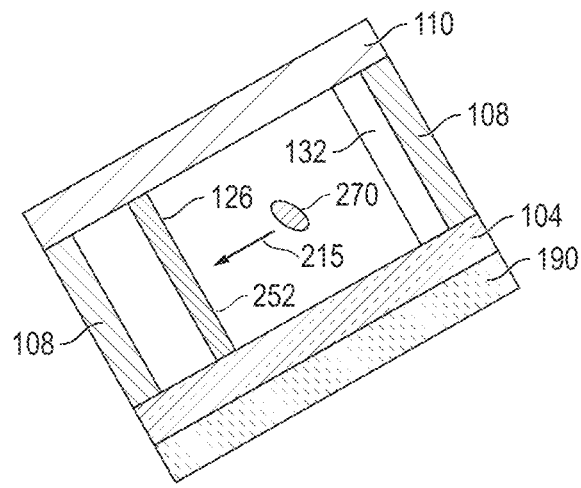
Figure 4G:
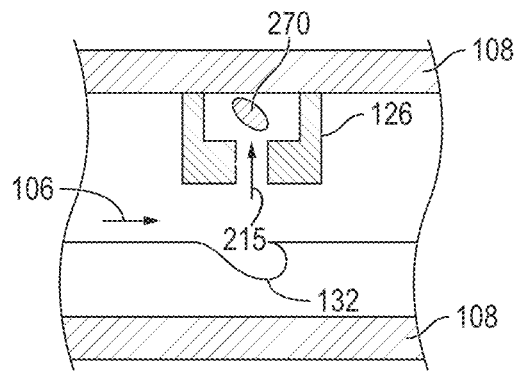

The trap 132 may be positioned directly opposite proximal opening 252, so as to be in an optimal position to transfer a captured target micro-object to the sequestration pen 126. For example, the trap 132 can receive and retain a target micro-object 270 from the fluidic medium 180 flowing through flow path 106, as shown in FIGS. 4C-4E. In some instances, the micro-object can then be transferred to the sequestration pen 126 using gravitational force. For example, the flow of fluidic medium 180 in the microfluidic circuit 120 can be stopped, and the microfluidic device 100 can be tilted so as to position the trap 132 above the sequestration pen 126. Gravitational force 215 can then displace the captured micro-object 270 from the trap 132 and cause the micro-object 270 to settle into the sequestration pen 126, as shown in FIGS. 4F-4G. The alignment of the trap 132 and the proximal opening 252 of the sequestration pen 126 can help to ensure that the micro-object 270 settles into the sequestration pen 126. Depending upon the configuration of the sequestration pen, and in particular the location of the isolation region 258 relative to the connection region 244, the gravitation force 215 can cause the micro-object 270 to settle into the isolation region 258, as shown in FIG. 4G. In some embodiments, DEP forces (e.g., OET) can be used, either alone or in combination with gravitational force, to transfer a captured target micro-object 270 from the trap 132 to the sequestration pen 126.

Figure 4H:
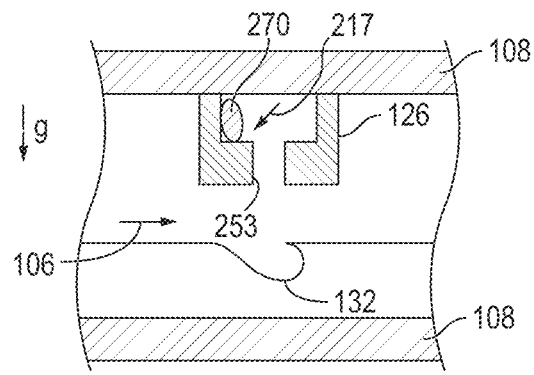

In some instances, after transferring a micro-object 270 to a sequestration pen 126, the microfluidic device 100 is subsequently tilted to a position wherein the sequestration pen 126 is above flow path 106 and trap 182. In such embodiments, a reduced width and/or a constriction of the connection region 254 and/or the distal opening 256 can prevent the micro-object 270 from exiting the pen 126 despite gravitational force. In some instances, microfluidic device 100 is tilted such that gravitational force 217 causes the target micro-object 270 to move to a location within the isolation region 258 that is unaligned with the connection region 254 and/or the distal opening 256. The microfluidic device 100 can then be further tilted such that the sequestration pen 126 is above flow path 106 and trap 132. As such, the gravitational forces on micro-object 270 may move micro-object 270 within the isolation region 258 and generally towards the flow path 106, but without causing the micro-object 270 to exit the sequestration pen 126, as shown in FIG. 4H.

In some embodiments, the micro-object 270 is removed from the sequestration pen 126 by tilting the microfluidic circuit 120 to cause the micro-object 270 to align with and exit the sequestration pen 126 via the connection region 254. In other instances, the micro-object 270 is removed from the sequestration pen 126 via DEP forces, such as OET, or a combination of DEP and gravitational forces.

Referring now to FIGS. 4C and 4D, in some instances a trap 132 comprises a volume that is at least as large as the volume of one target micro-object. As such, trap 132 may be capable of receiving and retaining only a single target micro-object 270. Subsequent target micro-objects 270a can thus be prevented from entering the trap 132, and therefore bypass the trap 132. Non-target micro-objects 272 also may be blocked by the retained micro-object 270. In some instances, the volume of the trap 132 prevents reception of larger non-target micro-objects 272, as shown in FIG. 4C. In some embodiments, smaller non-target micro-objects (not shown) are prevented from being retained within the trap 132 and are washed out of the trap 132 by fluidic medium flowing by the trap 132, due to poor spatial fitting between the small, non-target micro-object and the trap 132.

Referring now to FIGS. 5A-5D, a further schematic representation of a method for capturing targeted micro-objects within a microfluidic circuit 120 using gravitational force is shown. With reference to FIG. 5A, microfluidic circuit 120 may be scaled to include a plurality of microfluidic sequestration pens 130, a plurality of channels 122, and optionally a plurality of micro-object traps 132. Referring now to FIG. 5B, in some embodiments a flow path 106 for fluidic medium 180 is provided through channel 122. The fluidic medium can include a plurality of target micro-objects 270 (e.g., 270, 270a, 270b). Microfluidic circuit 120 can be tilted (but need not be) such that the gravitational force is directed towards trap 132, as shown. A first target micro-object 270a can be caught in trap 132. Depending on the size of the trap 132, a subsequent target micro-object 270a may be prevented from being captured in the trap 132 and can instead bypass the trap 132 and flow downstream. When some or all of the traps 132 have been filled with target micro-objects 270, the flow of medium in channel 122 can be slowed or stopped, and the microfluidic device 100 can be tilted such that gravity forces the micro-objects 270 to move in the direction 450 of the sequestration pen 130, as shown in FIG. 5C. In some instances, the tilting of the microfluidic device 100 occurs prior to slowing or stopping the flow of medium in channel 122. Regardless, micro-object 270 can be released from the trap 132 and can settle into isolation region 258 via connection region 254. Once a micro-object 270 has exited the connection region 254 and is unobstructed from entering the isolation region 258, the microfluidic device 100 can be tilted again, to change the direction of the gravitational force to be in the direction 452 of the isolation region 258, as shown in FIG. 5D.

Once micro-objects 270 have been positioned within the isolation regions 258 of a plurality of sequestration pens 130 (e.g., in the manner of FIG. 5D), additional micro-objects 570b can be loaded into the sequestration pens 130 of the microfluidic device 100, as described above. In this manner, supra-Poisson loading of the sequestration pens 130 in the microfluidic circuit 120 can be achieved and/or additional micro-objects 270b can be added to sequestration pens 130 that already have a micro-object 270, as shown in FIGS. 5E-5F. For example, once a micro-object 270 is loaded in the isolation region 258 of a sequestration pen 130, the microfluidic device 100 can be tilted yet again to change the direction 454 of the gravitational force towards the channel 122 and the trap 132, thereby causing micro-objects 270 to locate deep within isolation region 258, as shown in FIG. 5E. The flow of medium 180 in the channel 122 can then resume and a subsequent target micro-object 270b can be retained in the trap 132. Once some or all of the traps 132 have been filled with subsequent micro-objects 270b, the flow of medium 180 in the channel 122 can be stopped and the device 100 can be tilted to reverse the direction of the gravitational force to be in the direction 450 of the pen 130, as shown in FIG. 5F. Accordingly, target micro-objects 270 and 270b can both be displaced downwardly within the pen 130 (with micro-object 270 displaced downward in the isolation region 258 and micro-object 270b displaced downward in the connection region 254) by repeating the step shown in FIG. 5C. Micro-objects 270 and 270b can then be sequestered together in the isolation region 258 by repeating the step shown in FIG. 5D. Additional target micro-objects can be sequestered by repeating the steps shown in FIGS. 5B-5F. In some instances, steps 5B-5F are repeated a specific number of times to collect a specific number of micro-objects in each sequestration pen 130. In some embodiments, steps 5B-5D and 5E-5F can be performed with different types of micro-objects 270, 272, thereby allowing sequestration pens 130 to be filled with a mixture of different types of micro-objects.

Although in the foregoing descriptions of FIGS. 4A-H and 5A-F the microfluidic devices include traps, persons skilled in the art will appreciate that such traps need not be present and that the methods of loading micro-objects into the sequestration pens (and, e.g., the isolation regions thereof) can be performed reliably in the absence of such traps. For example, by providing a sufficient density of micro-objects (e.g., about $1.0 \times 10^5$ micro-objects/mL to about $5.0 \times 10^7$ micro-objects/mL) in the fluidic medium in the channel, there can be a high probability of having one or more micro-objects located above the proximal opening of the connection region when the microfluidic device is tilted along an axis substantially parallel to the axis of the flow path. Thus, there may be no need to capture micro-objects in traps to ensure that micro-objects get loaded into a high percentage of the sequestration pens in a microfluidic device.

Figure 6A:
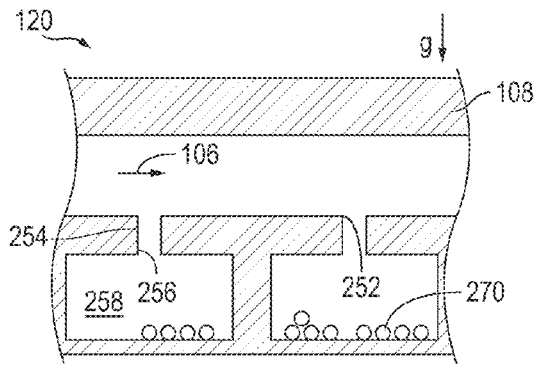
FIGS. 6A-6J provide cross-section views of microfluidic devices having a microfluidic channel and sequestration pens, the sequestration pens having various surfaces and features optimized for use in collecting micro-objects via gravitational forces according to some embodiments of the invention.
Figure 6B:
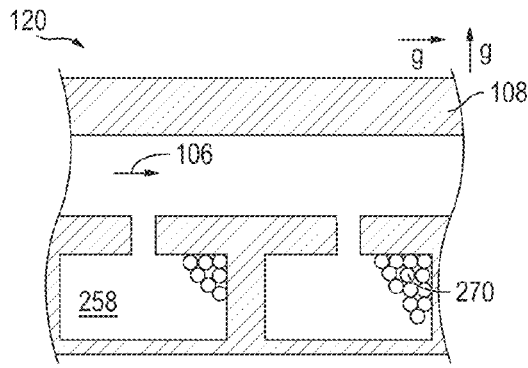

Referring now to FIGS. 6A-6I, various cross-sectional top views of non-limiting examples of sequestration pens are shown. A similarly shaped pen 126 is illustrated in FIG. 1. FIGS. 6A and 6B illustrate sequestration pens having a constricted proximal opening 252, connection region 254, constricted distal opening 256, and an expansive isolation region 258 having a volume configured to store a plurality of micro-objects 270. The combination of the constricted distal opening 256 and the expansive isolation region 258 encourages the micro-objects 270 to remain within isolation region 258, despite the degree to which the microfluidic device 100 may be tilted. Tilting of the microfluidic device 100 along two axes (e.g., first along an axis substantially parallel to the flow path 106, and second along an axis substantially parallel to the length of the connection region 254 from proximal to distal openings 252, 256), as shown in FIG. 6B, causes micro-objects 270 to collect within a corner of the isolation region 258, thereby further preventing loss of micro-objects 270 via the distal opening 256.

Figure 6C:
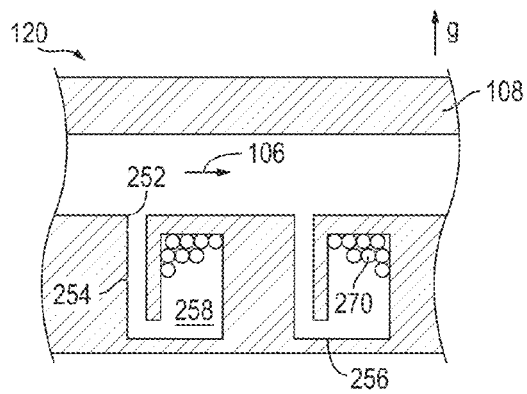

In FIG. 6C, the sequestration pen is shown as having a nautilus-like shape. A similarly shaped pen 130 is illustrates in FIG. 1. In this example, the nautilus-like shape is characterized by a connection region 254 comprising two regions oriented at right angles to one another, thus forming an "L" shape extending from the proximal opening 252 to the distal opening 256. In sequestration pens having a nautilus-like shape, the distal opening 256 can be perpendicular to the flow path 106. In the embodiment illustrated in FIG. 6C, the nautilus-like shape is characterized by a constricted proximal opening 252, a constricted distal opening 256, and connection region 254, wherein the cross-sectional area or width of the proximal opening 252, the distal opening 256, and/or connection region 254 are all substantially the same. Of course, this need not be the case, and the openings 252, 256 can have a cross-sectional area or width that is different from one another and/or the connection region 254. Regardless, the cross-sectional areas (or widths) can be selected to accommodate target micro-objects having a known diameter, width and/or cross-section area. In some instances, the nautilus-like shape further comprises an isolation region 258 having a volume configured to retain a plurality of target micro-objects 270.

Figure 6D:
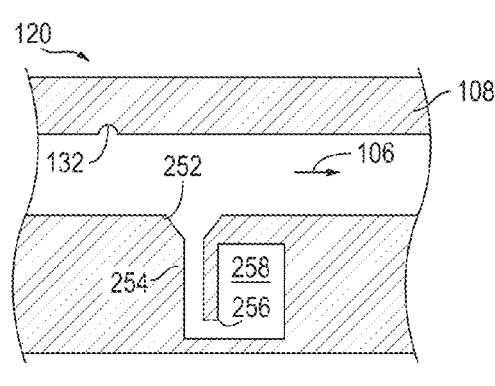

In some embodiments, a nautilus-like shaped sequestration pen can further comprise a widened proximal opening 252, which may be chamfered, as shown in FIG. 6D, or beveled. In some instances, the widened proximal opening 252 can be positioned opposite a micro-object trap 132, as discussed previously. The widened proximal opening 252 can assist in collecting micro-objects that are displaced from trap 132. The trap 132 need not be located directly across the channel 122 from the proximal opening 252, but can be located slightly upstream (as determined relative to the flow path 106).

Figure 6E:
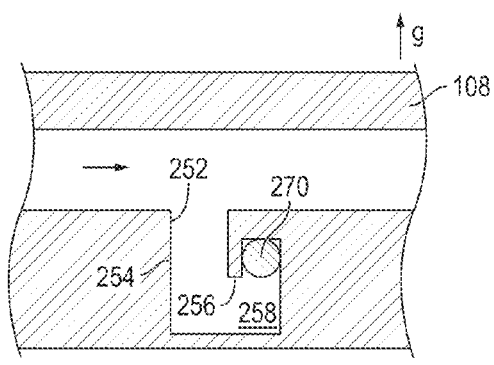

In some embodiments, a nautilus-like shaped sequestration pen can comprise an isolation region 258 having a volume configured to retain a single micro-object 270, as shown in FIG. 6E. The distal opening 256 and the connection region 254 can comprise a width that is at least equal to (or greater than) the diameter or width of the micro-object 270. For this embodiment, once the micro-object 270 is loaded into the isolation region 258, the microfluidic device 100 may be tipped on its side and rotated counter-clockwise about an axis perpendicular to the floor of the microfluidic circuit 120. By so doing, any micro-objects that are located within the distal opening 256 or connection region 254 will be displaced into flow path 106, while the position of the micro-object 270 within isolation region 258 can be maintained.

Figure 6F:
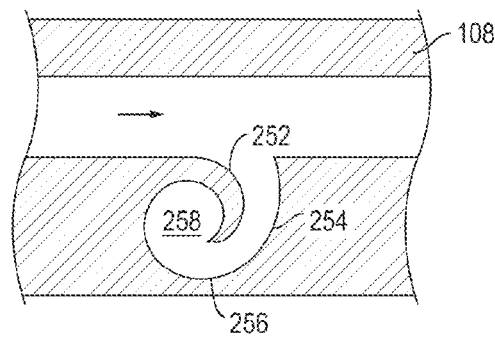
Figure 6G:
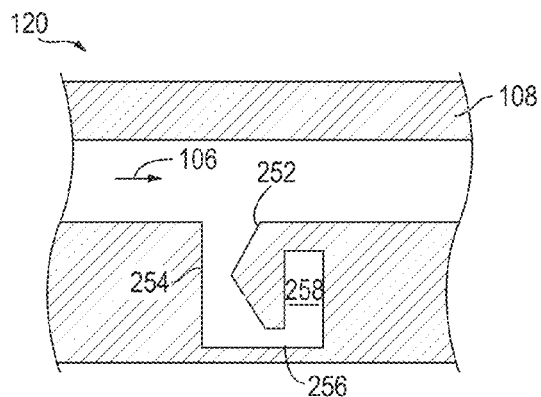

In some instances, the sequestration pen can comprise a curved profile, as shown in FIG. 6F and FIG. 1 (e.g., 124). In other instances, sequestration pens with a nautilus-like shape may be configured as shown in FIG. 6G, wherein the connection region 254 includes a constriction such that the proximal opening 252 is wider than the constricted portion of the connection region 254, and the distal portion of the connection region 254 is wider than the constricted portion, thereby giving the connection region 254 an hourglass-like shape. In some embodiments, the sequestration pen can comprise a boot-like shape characterized by an isolation region 258 extending laterally from the connection region 254. In such embodiments, the distal opening 256 can have a smaller width then either the connection region 254 or the isolation region 258, thus providing a constriction between the connection region 254 and the isolation region 258.

Figure 6H:
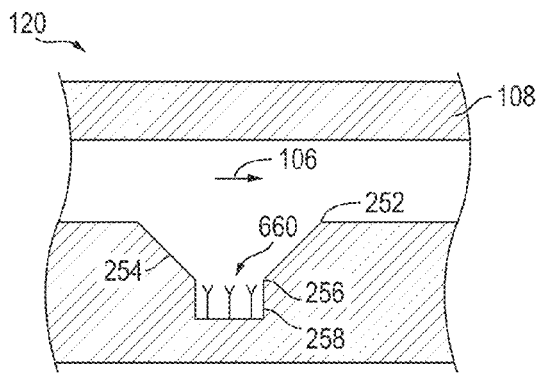

Referring now to FIG. 6H, in some embodiments, the sequestration pen comprises a funnel-like shape characterized by a widened proximal opening 252, a narrowed distal opening 256, and a beveled (or chamfered) connection region 254. In some instances, isolation region 258 comprises one or more functional moieties 660 for selective binding one or more target micro-objects. The functional moieties can be deposited on the microfluidic circuit structure 108 or, alternately, affixed to a region of the microfluidic circuit structure 108 (e.g., by covalent linkage or by inclusion in a polymer network). In some instances, functional moieties 660 can be affixed to magnetic beads and localized within the microfluidic circuit structure using magnetic forces (i.e. held to a bottom of the sequestration pen using magnetic force). Alternatively, the functional moieties 660 can be affixed to beads (e.g., non-magnetic beads, such as polystyrene beads) and localized within the microfluidic circuit structure using DEP forces (e.g., OET).

According to the embodiment, functional moieties 660 can comprise a reagent and/or analyte of interest for an assay. In some embodiments, the isolation region 258 comprises one or more antibodies that are configured to selectively bind a desired target micro-object. In some instances, a specific number of antibodies are provided with the intention of binding a specific number of micro-objects. Once binding is complete, the sequestration pen may be inverted to displace any unbound micro-objects for transport back into flow path 106. Unbound micro-objects may be removed, for example, using any combination of gravity, DEP, and OET, as discussed above. In instances where the functional moieties 660 are deposited on beads and held within a sequestration pen, the functional moieties 660 may also be displaced from the sequestration pen into the flow path 106. For example, magnetic beads can be displaced into the flow path 106 by eliminating the magnetic force and allowing the force of gravity to act on the functional moieties. Alternatively, the functionalized beads can be displaced into the flow path 106 using DEP, OET, and/or gravity.

Figure 6I:
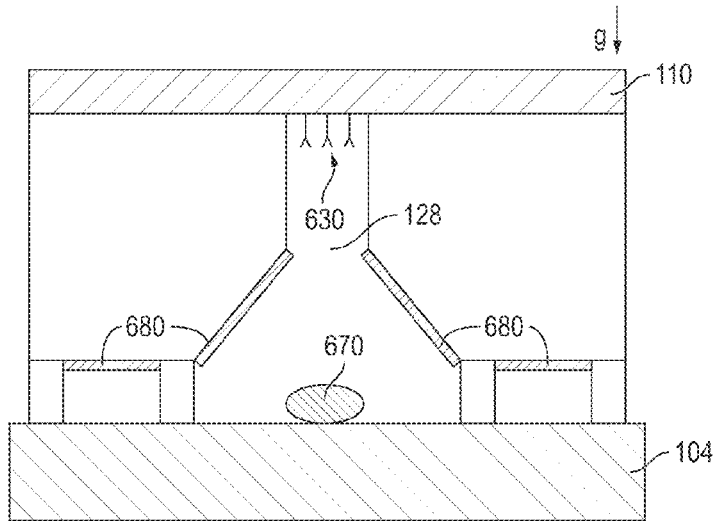

Referring now to FIG. 6I, in some instances a single micro-object is loaded into a sequestration pen having two or more functional moieties 660. In some instances, the two or more functional moieties are attached to the cover 110 of microfluidic circuit 120, while in other embodiments the functional moieties are attached to a surface of the sequestration pen, such as the inner surface of the support structure 104. In one embodiment, the functional moieties 660 are antibodies and a single cell 670 is loaded into a sequestration pen having two or more antibodies 630 located on the inside surface of the cover 110 within the sequestration pen. When the tilting apparatus is in the upright position, the cell 670 is prevented from coming into contact with the antibody. The cell 670 can be manipulated into and within the sequestration pen via gravity and/or DEP forces, such as optoelectronic tweezers (OET). Once in the sequestration pen, the cell 670 can undergo cellular cloning. The sequestration pen can further comprise indium tin oxide (ITO) electrodes, which may be located on various surfaces (e.g., 110, 680) of the pen and provide for taking spectro-electrochemical measurements to determine the progress of the cellular cloning process.

Once cloning is substantially complete, the tilting apparatus can be tilted relative to the x-axis (e.g. 10°, 15°, 20°, 25°) to change the direction of gravity, whereby the newly cloned cells can be brought into contact with the antibodies 630. Following the binding between the cells 470 and the antibodies 630, the microfluidic circuit 120 is again tilted to change the direction of gravity, whereby all unbound cells 670 can settle on the inner surface of the support structure 104, away from the cover. The unbound cells can then be removed, and the bound cells can be measured (such as with the ITO electrodes) and/or imaged through the transparent cover 110 with minimal background noise.

Figure 6J:
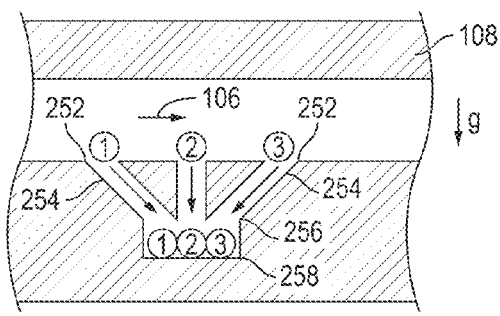

In some embodiments, a microfluidic sequestration pen is provided having a single isolation region 258 and a plurality of proximal openings 252, distal openings 256, and connection regions 254, as shown in FIG. 6J. In some embodiments, at least one of the proximal openings 252, distal openings 256, and connection regions 254 comprises a unique width to accommodate a unique target micro-object. In some embodiments, each proximal opening 252, distal opening 256, and connection region 254 is identical is size and is provided to reduce the loading time for isolation region 258 and/or increase the average number of micro-objects that are loaded into the isolation region 258 at any given time. Further still, in some embodiments the locations of the proximal openings 252 can be positioned to receive one or more micro-objects that have been presorted or isolated, such as by DEP or OET.

Figure 6K:
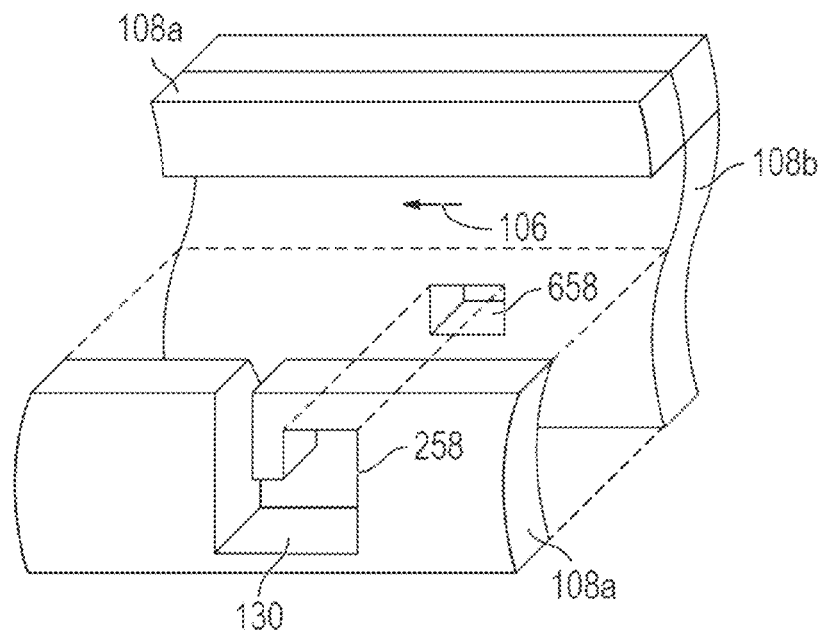
FIGS. 6K and 6L provide perspective, exploded views of sequestration pens having first and secondary isolation regions in accordance to some embodiments of the invention.
Figure 6L:
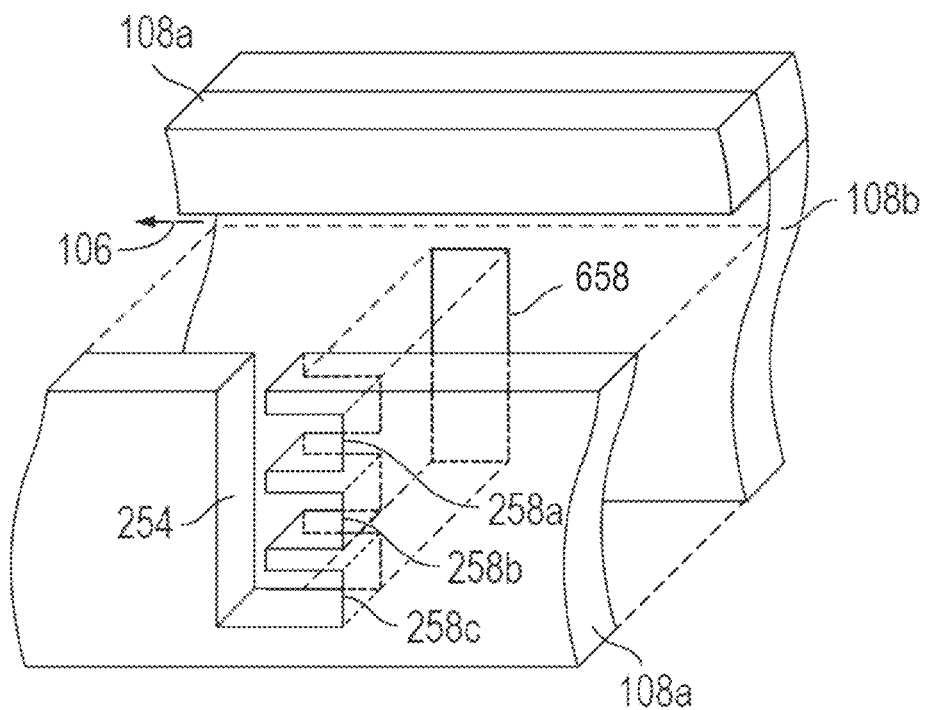

Referring now to FIGS. 6K and 6L, in some embodiments one or more portions of the isolation region 258 of a sequestration pen 130 is aligned with a secondary isolation region 658 that is located in a secondary layer 108b of the microfluidic circuit structure 108a. Accordingly, isolation regions 258 and 658 provide a three-dimensional pen shape. Referring now to the nautilus-like sequestration pen 130 of FIG. 6K, the upper most or inner most tip of the isolation region 258 overlaps the secondary isolation region 658 provided in the secondary layer 108b of the microfluidic circuit structure 108a. Thus, a micro-object within the isolation region 258 may access and enter the secondary isolation region 658 by being moved to the inner-most tip of isolation region 258. Once located within the inner-most tip of isolation region 258, microfluidic device 100 can be tilted to change the direction of the gravitational force in the downward direction, towards the secondary layer 108b, thereby permitting the micro-object to settle into the secondary isolation region 658.

The microfluidic device 100 of FIG. 6L comprises a sequestration pen having a plurality of isolation regions 258a, 258b, and 258c which extend laterally outward from connection region 254, whereby isolation regions 258a, 258b, and 258c are aligned in a row. Isolation regions 258a, 258b, and 258c overlap secondary isolation region 658 provided in the secondary layer 108b of the microfluidic circuit structure 108a. Thus, one or more micro-objects within isolation region 258a-c may access and enter the secondary isolation region 658 by tilting the microfluidic device 100 and changing the direction of the gravitational force in the downward direction towards the secondary layer 108b, thereby permitting the micro-objects to settle into the secondary isolation region 658.

The present invention further comprises various structures and methods for precise gravity loading of micro-objects. Some embodiments of the present invention are capable of providing Poisson loading with a distribution accuracy of lambda=1 or 2. For some methods of the instant invention, centrifugal forces and/or jarring, jerking, shaking, or off-tool movements (i.e. via human hands) may be substituted for gravitational forces. In other methods, off-tool movements may be substituted for tilting the microfluidic device 100.

Figure 7A:
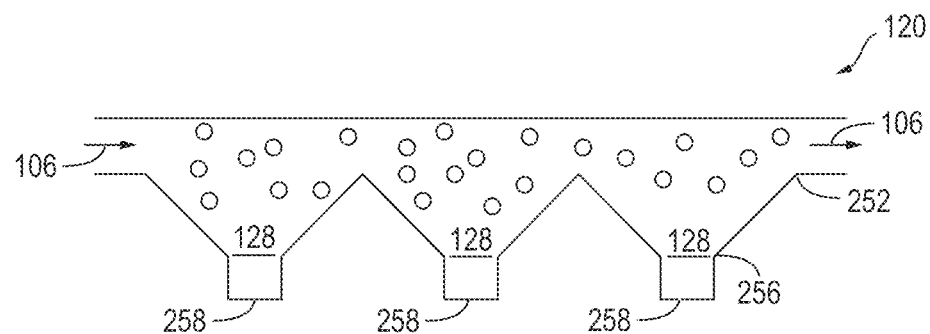
FIGS. 7A-7B provide cross-section views of a microfluidic device having a microfluidic channel and a set of concentration pens, showing a method for gravity loading according to some embodiments of the invention.
Figure 7B:
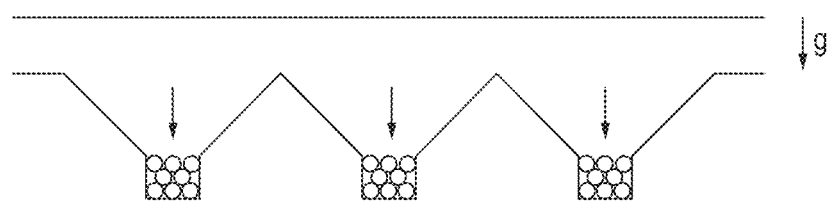

Referring now to FIGS. 7A and 7B, a portion of a microfluidic circuit 120 is shown comprising three sequestration pens 128 having a funnel-like shape, and each comprising an isolation region 258. Isolation regions 258 are in fluid communication with flow path 106 via the widened proximal openings 252, beveled (or chamfered) connection regions 245, and narrowed distal openings 256.

To load the sequestration pens 128, the flow of medium in the flow path 106 can be stopped and the microfluidic device 100 can be tilted to reposition the flow path 106 (and any micro-objects contained in the medium) above the pens. In repositioning the location of the flow path 106, the direction of the gravitational force is changed to be towards isolation regions 258. The micro-objects can be allowed to settle into the isolation regions 258 under the gravitational force, as shown in FIG. 7B. Because of the beveled (or chamfered) structure of the connection regions 254, micro-objects loaded in this manner can be concentrated.

Figure 8A:
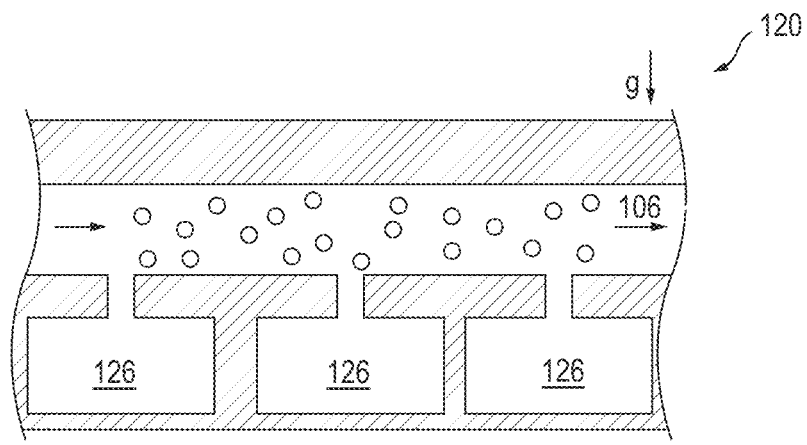
FIGS. 8A-8C provide cross-section views of a microfluidic device having a microfluidic channel and a set of sequestration pens showing a method for gravity loading according to some embodiments of the invention.
Figure 8B:
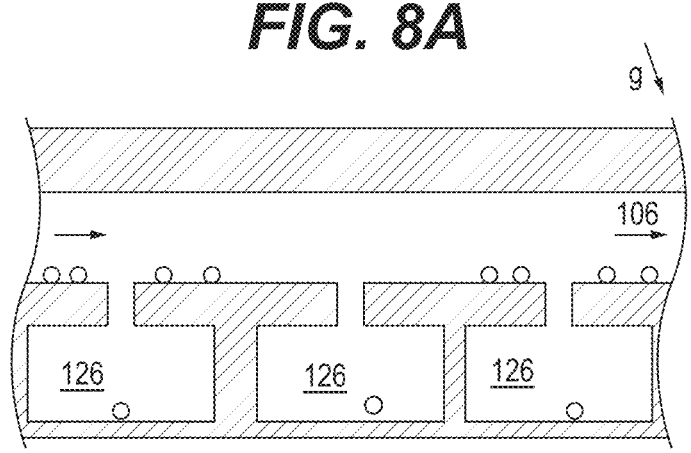
Figure 8C:
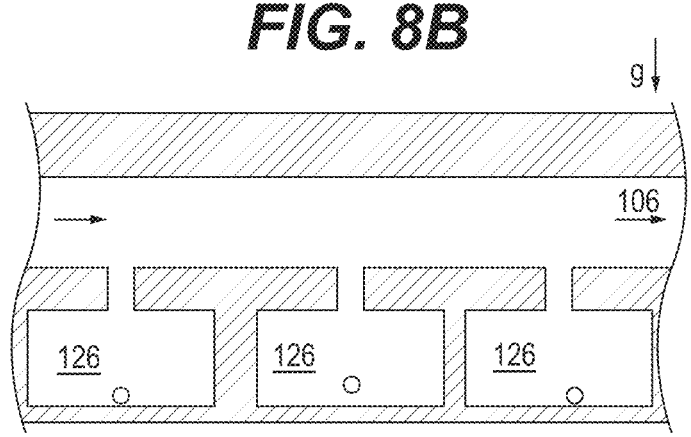

In some instances it may be desirable to load individual (or multiple) micro-objects. This can be accomplished by controlling the size of the proximal opening (and/or the distal opening) and the seeding density of the micro-objects in the flow path 106. In some embodiments, a plurality of micro-objects is passed through the flow path 106, as shown in FIG. 8A. The flow of micro-objects can be substantially homogeneous (e.g., at a known density or concentration). For example, in some instances the fluidic medium 180 comprises a target micro-object concentration from about $1.0 \times 10^5$ to about $5.0 \times 10^6$, about $2.5 \times 10^5$ to about $1.0 \times 10^7$, about $5.0 \times 10^5$ to about $2.0 \times 10^7$, or about $7.5 \times 10^5$ to about $3.0 \times 10^7$. When the desired density of micro-objects is provided in the flow path 106, the flow of micro-objects can be stopped and the microfluidic device 100 can be tilted to change the direction of the gravitational force towards the sequestration pens 126, as shown in FIG. 8B. Depending upon, e.g., the cell density and the size of the proximal opening of the sequestration pen, it is possible to accurately estimate the load for each sequestration pen. As shown in FIG. 8B, a high cell density and a narrow proximal opening can result in single-cell loading in a plurality (or even a majority) of the sequestration pens. Alternatively, a low cell density and a wider proximal opening can result in single-cell loading in a plurality (or even a majority) of the sequestration pens. Once the load is complete, the flow of fluidic medium 180 through the flow path 106 can resume, thereby removing any micro-objects within flow path 106, as shown in FIG. 8C. In some instances, the fluidic medium 180 comprises a target micro-object density such that more than 35%, or no more than 13% of the plurality of sequestration pens do not contain any target micro-objects after allowing gravity to act on the target micro-objects for an amount of time sufficient for any target micro-objects located in the first portion of the flow path to settle into the sequestration pen.

Figure 9A:
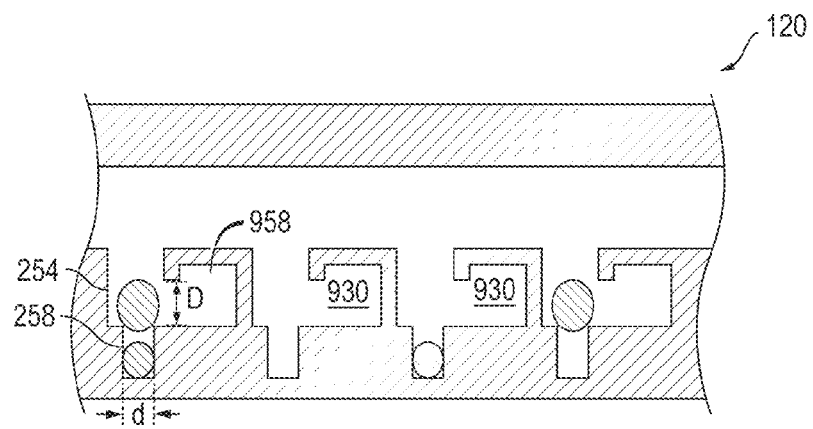
FIGS. 9A and 9B provide cross-section views of a microfluidic device having a microfluidic channel and a set of t-shaped sequestration pens, with each pen having multiple isolation regions, according to some embodiments of the invention.
Figure 9B:
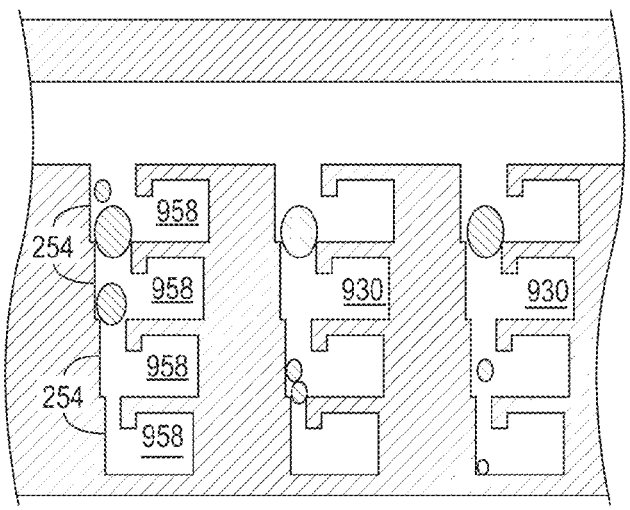

Referring now to FIGS. 9A and 9B, some embodiments of the present invention comprise a microfluidic sequestration pen having a plurality of isolation regions 258, 958. For example, in some embodiments a sequestration pen 930 is provided comprising a first isolation region 258, which may extend distally from the distal end of the connection region 254 (shown in FIG. 9A) or laterally from the end of the connection region, and can have an opening with a width "d" configured to receive a first micro-object having a diameter or width approximately equal to diameter "d". The sequestration pen 930 can further comprise a second isolation region 958 having an opening with a width "D" configured to receive a second micro-object having a diameter or width approximately equal to diameter "D". The second isolation region 958 can extend laterally from a side of the connection region 254. Thus, the sequestration pen 930 can have a "t-shape", as shown in FIG. 9A. Some embodiments of the present invention further comprise a single sequestration pen having a plurality of isolation regions 958, wherein the plurality of isolation regions 958 are laterally aligned along one side of the connection region 254, as shown in FIG. 9B. In some instances, the plurality of isolation regions 958 is two. In some embodiments, the isolation regions of the plurality each comprise a unique volume and/or width, which may be configured to receive a unique micro-object. In some embodiments, the isolation regions of the plurality each have substantially the same volume and/or width.

Figure 10:
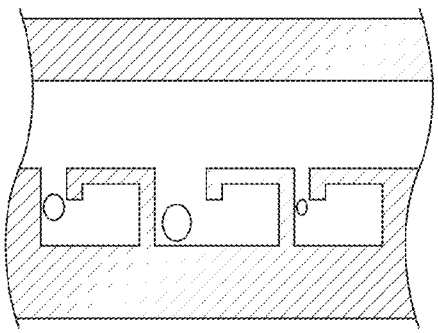
FIG. 10 is a cross-section view of a microfluidic device having a microfluidic channel and a set of sequestration pens, wherein the opening of each connection region to the microfluidic channel is unique according to some embodiments of the invention.

Some embodiments of the present invention provide a microfluidic circuit 120 comprising a plurality of microfluidic sequestration pens having unique dimensions, wherein each sequestration pen comprises a proximal opening 252 and/or connection region 254 having a unique width (and/or volume, in the case of the connection region 254), each of which may be configured to accommodate a unique micro-object, as shown in FIG. 10.

Various embodiments of the present invention further comprise one or more micro-object traps 132, as discussed above. Traps 132 may comprise any structure in accordance with the teachings of the instant invention. In some embodiments, microfluidic device 100 comprises one or more traps 132 positioned within flow path 106, and having a structure configured to encourage flow of fluidic medium 180 into or through the one or more traps 132.

Figure 11A:
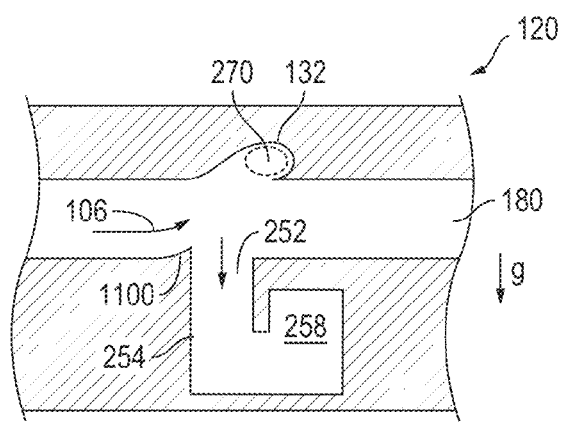
FIGS. 11A and 11B provide cross-section views of a microfluidic device having a microfluidic channel, a sequestration pen, and a micro-object trap located across the channel from the opening to the pen, according to some embodiments of the invention.

For example, FIG. 11A shows a micro-object trap 132 comprising a notch formed on a wall at the boundary of flow path 106. The trap 132 may be positioned opposite the proximal opening 252 of a sequestration pen. In some embodiments, the flow path 106 further comprises a ramped surface 1100 located adjacent to the proximal opening 252 and having a ramped angle configured to divert the flow path 106 of fluidic medium 180 towards trap 132. The diverted medium carries micro-objects 270 up to trap 132 where they become trapped. Upon stopping the flow of fluidic medium 180 through the flow path 106, the captured target micro-object 270 can be displaced from trap 132 and guided into isolation region 258 via proximal opening 252 and connection region 254.

Figure 11B:
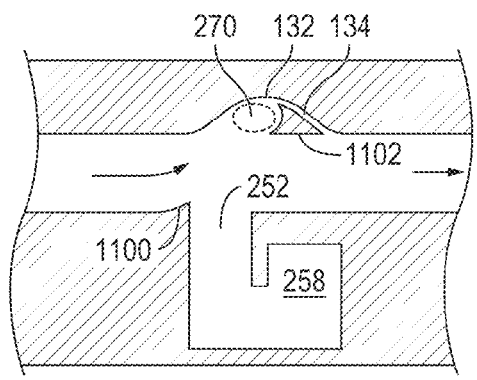

FIG. 11B provides an additional example of a micro-object trap 132 in accordance with the present invention. Trap 132 also comprises a notch formed on a wall of flow path 106 and positioned opposite proximal opening 252 of a sequestration pen. However, trap 132 further comprises a side passage 134 that allows fluid to flow past a catch (or barrier) 1102. Side passage 134 eliminates aberrant currents that may otherwise occur as fluid enters and exits the same opening of trap 132 of FIG. 11A. These aberrant currents may prevent a micro-object 270 from being trapped within trap 132. Accordingly, side passage 134 can eliminate these currents and thereby increase the likelihood of capturing target micro-objects 270.

Figure 12:
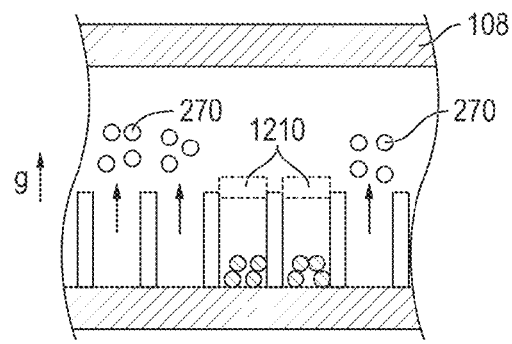
FIG. 12, is a cross-section view of a microfluidic device having a microfluidic channel and a set of sequestration pens, demonstrating the use of OET forces to maintain the position of micro-objects within a pair of sequestration pens according to some embodiments of the invention.

Further control of micro-object loading and unloading can be achieved by combining the various gravity-based techniques discussed herein with additional techniques such as DEP and/or OET. For example, in some embodiments micro-objects are initially loaded, and subsequently unloaded via gravity, but a small, select subset of micro-objects are held in place by OET force 1210, and therefore are prevented from being unloaded by gravity, as shown in FIG. 12. This technique could also be used to selectively retain micro-objects of interest after assaying for some component or characteristic of interest, such as an antibody secretion. In alternate embodiments, the structure of the microfluidic circuit 120 shown in FIG. 12 (i.e., having pens formed by linearly-shaped walls) can be used to generate uniform particle density within flow path 106. For example, in some embodiments, flow path 106 comprises one or more sequestration pens having linear walls and equivalent volumes and extending along the entire length of flow path 106. The sequestration pens may be filled with micro-objects via gravity loading techniques discussed herein. Once the pens are filled, fluid shear will push micro-objects downstream to fill up downstream sequestration pens. Once all the pens are full (e.g., to an amount permitted by secondary flow into the connection regions of the pens), the microfluidic device 100 is tilted in the opposite direction to release all of the micro-objects into the flow path at the same time. The simultaneous entry of the micro-objects into the flow path 106 creates a substantially uniform density (at least initially) along the entire length of the flow path. In other embodiments, this method is used to concentrate cells spatially, whereby cells may enter the sequestration pens at a given density, but upon tilting, the cells are physically forced into close proximity with one another in the sequestration pens.

Figure 13A:
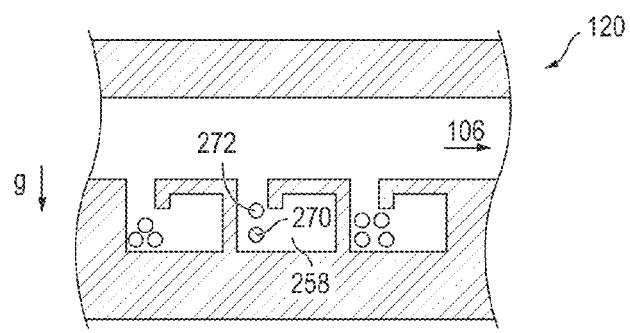
FIGS. 13A-13D provide cross-section views of a microfluidic device having a microfluidic channel and a set of sequestration pens, demonstrating the combined use of gravitational and OET forces to position of a single target micro-object within an isolation region of a sequestration pen, according to some embodiments of the invention.
Figure 13B:
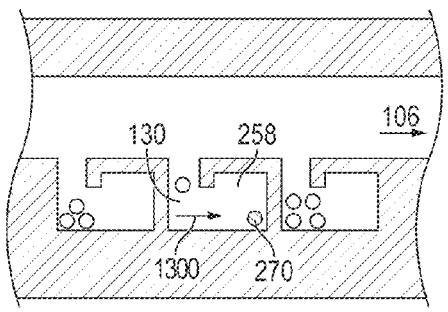
Figure 13C:
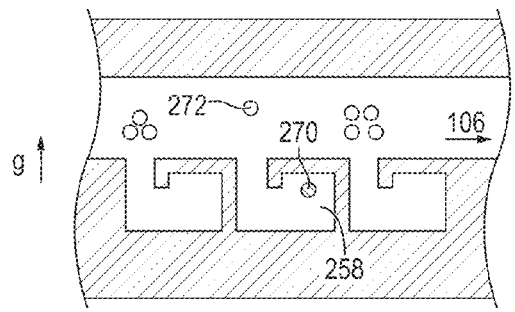
Figure 13D:
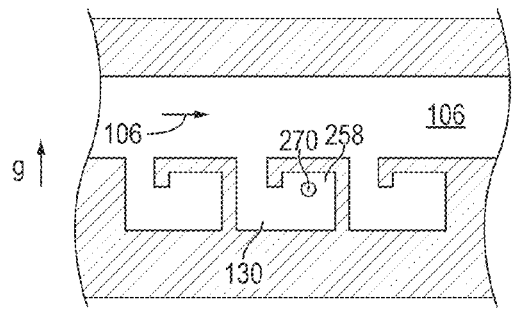

Referring now to FIGS. 13A-13D, some embodiments of the present invention provide a method which utilizes gravitational and DEP (e.g., OET) forces to selectively move and retain a target micro-object 270 with a sequestration pen 130. With reference to FIG. 13A, microfluidic device 100 (and hence microfluidic circuit 120) is tilted to position flow path 106 above sequestration pens 130, thereby directing the gravitational force towards the sequestration pens 130 and causing non-target micro-objects 272 and target micro-object 270 alike to settle into the sequestration pens 130. DEP forces 1300 are then used to select and move a target micro-object 270 into isolation region 258, as shown in FIG. 13B. Microfluidic device 100 is then tilted to position the sequestration pens 130 above the flow path 106, such that the direction of the gravitational force is towards flow path 106, thereby causing non-target micro-objects 272 to exit pens 130, as shown in FIG. 13C. Target micro-object 270 remains within isolation region 258. A flow of fluidic medium 180 is provided through flow path 106 to remove the non-target micro-objects 272, as shown in FIG. 13D. Of course, variations on this method are possible. For example, the target micro-object 270 and non-target micro-objects 272 can be moved into the isolation region 258 as a group. Then, DEP forces can be used to select and move non-target micro-objects 272 back into the connection region 254. Finally, the microfluidic device 100 can be tilted such that the flow path 106 is below the connection region 254 such that the non-target micro-objects 272 settle into the flow path 106 while the target micro-object 270 is retained in the isolation region 258. Regardless of the timing of the selection step, the foregoing methods can be used to achieve supra-Poisson loading of the sequestration pens (e.g., the pens can be loaded with a larger variance than a Poisson distribution but the same mean). For example, the fluidic medium 180 can comprise a micro-object density such that no more than 35%, or no more than 13%, of the plurality of sequestration pens lack target micro-objects after gravity loading the micro-objects (as shown in FIG. 13A). Furthermore, the gravity loading and unloading steps (e.g., as shown in FIGS. 13A-D) can optionally be repeated at least once, thereby ensuring that an even greater percentage of the pens (e.g., at least 90%, 91%, 92%, 93%, 94%, 95%, 96%, 97%, 98%, 99%, or more) contain a single target micro-object 270. In some embodiments, repeated loading does not result in micro-objects being added to isolation regions which already have micro-objects loaded therein. Prior to gravity loading the micro-objects, a homogenous flow of micro-objects (at a known density or concentration) can be provided within flow path 106. For example, in some instances the fluidic medium 180 can comprise a micro-object concentration from about $1.0 \times 10^5$ to about $5.0 \times 10^6$, about $2.5 \times 10^5$ to about $1.0 \times 10^7$, about $5.0 \times 10^5$ to about $2.0 \times 10^7$, or about $7.5 \times 10^5$ to about $3.0 \times 10^7$.

Figure 14:
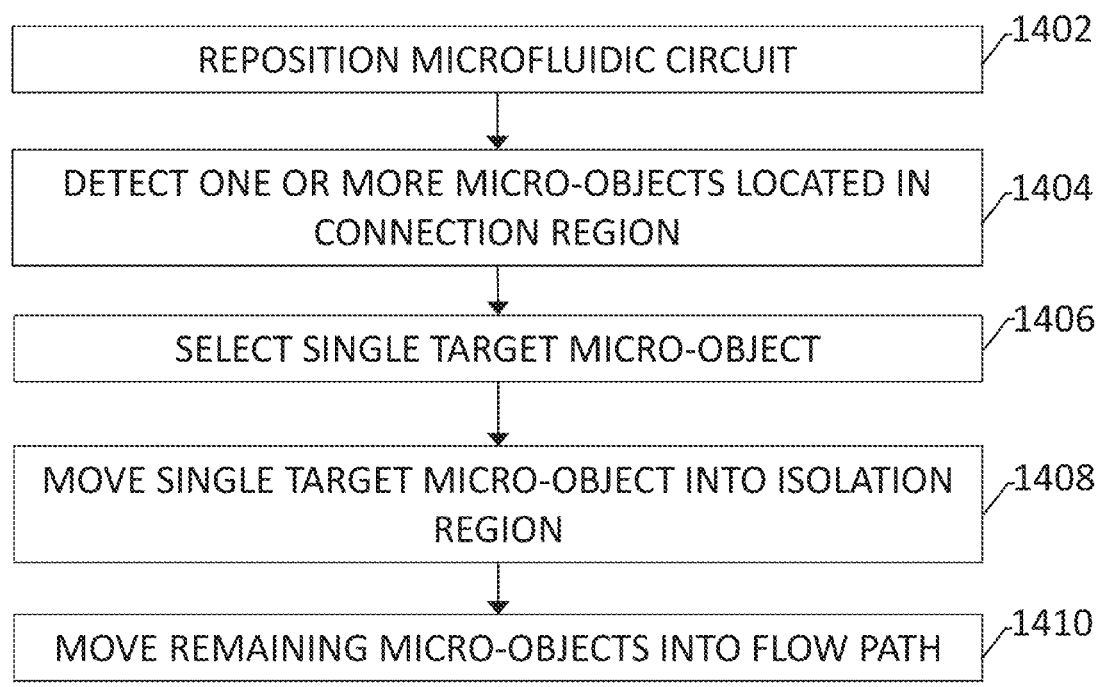
FIG. 14 illustrates a process for selecting and moving a single target micro-object into the isolation region of a sequestration pen utilizing gravitational forces, according to some embodiments of the invention.

FIG. 14 illustrates an example of a process 1400 for moving one or more target micro-objects in an isolation region of a sequestration pen of a microfluidic circuit 120. As shown, at step 1402, the process 1400 includes a first step for optionally repositioning the microfluidic circuit 120 (e.g., by tilting the microfluidic device 100), such as to shift or redirect a gravitational force on a target micro-object. In some instances, step 1402 may be performed multiple times to correctly position a target micro-object within a connection region of the sequestration pen. In some instances, step 1402 comprises moving the microfluidic circuit 120 to a level location suitable for microscopic analysis of the enclosure and/or moving micro-objects by means of electrokinetic force, such as DEP and/or OET. For example, the step of repositioning can involve "un-tilting" the microfluidic circuit 120. In some embodiments, an instrument is provided for generating an electrokinetic force, the instrument comprising a spatial light modulator and a controller for controlling the spatial light modulator.

A second step 1404 comprises detecting one or more target micro-objects located in a connection region of a sequestration pen. Once a target micro-object has been detected, the single target micro-object is selected from one or more target micro-objects (at step 1406). The selected, single target micro-object is then moved from the connection region of the sequestration pen to the isolation region (at step 1408). In some instances this step is accomplished via gravitational forces by tilting microfluidic circuit 120. In other instances, this step is accomplished via DEP and/or OET forces. The choice between gravitational force and DEP and/or OET forces can be driven by the average number of micro-objects in the connection regions. For example, if most of the connection regions have a single micro-object, then the micro-objects can be moved to the isolation regions of the sequestration pens using gravitation force. DEP and/or OET force can then be applied to remove non-target micro-objects from the relatively small number of isolation regions that contain more than one micro-object. A final step 1410 involves moving any target micro-objects remaining in the connection region back into the flow path of microfluidic circuit 120, which can be performed by application of gravitational force and, optionally, DEP and/or OET forces, as discussed above.

In some instances, the selected target micro-object in step 1406 does not move into the flow path when the step is executed. Accordingly, in some embodiments the selected target micro-object is manually moved by an electrokinetic force, such as a bar of dielectrophoresis or OET forces sweeping the length of the connection region.

Figure 15:
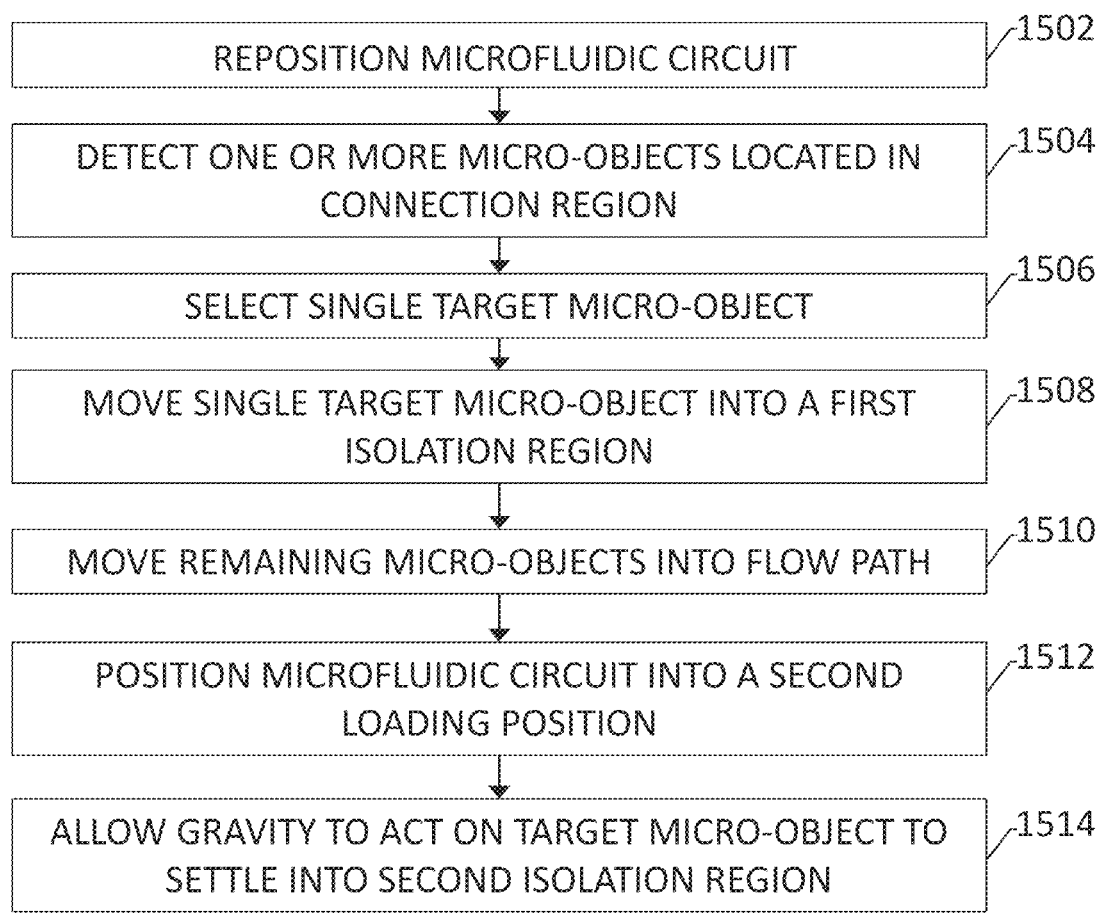
FIG. 15 illustrates a process for selecting and moving multiple target micro-objects utilizing gravitational forces according to some embodiments of the invention.

Referring now to FIG. 15, method 1500 includes two steps additional to the steps of method 1400. In particular, method 1500 includes a step 1512 for repositioning microfluidic device 100 into a second loading position. Step 1514 then allows for gravity to act on target micro-objects located in the first portion of the isolation region for an amount of time sufficient for any such target micro-objects (which would be located above an opening to a secondary isolation region) to settle into the secondary isolation region.

Figure 16A:
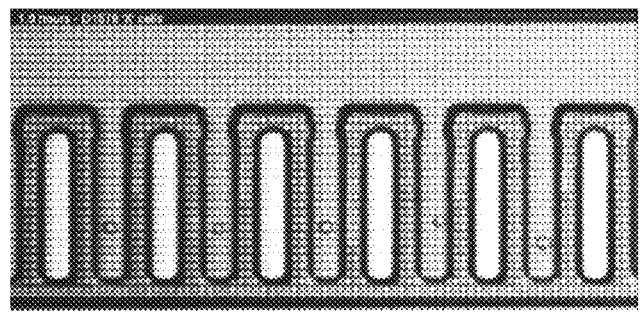
FIGS. 16A-16D show time elapsed photographs of cell division and growth in sequestration pens that have been tilted according to a specific embodiment of the invention.
Figure 16B:
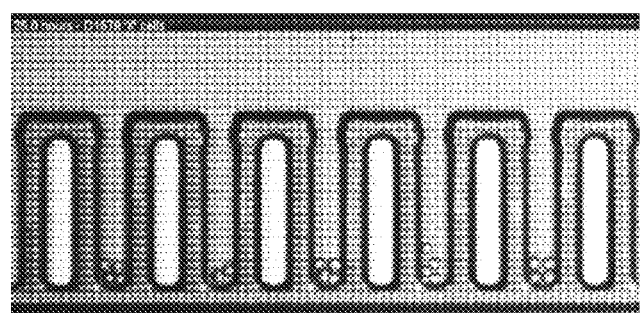
Figure 16C:
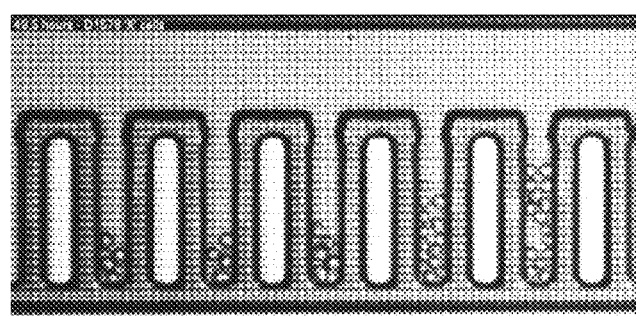
Figure 16D:
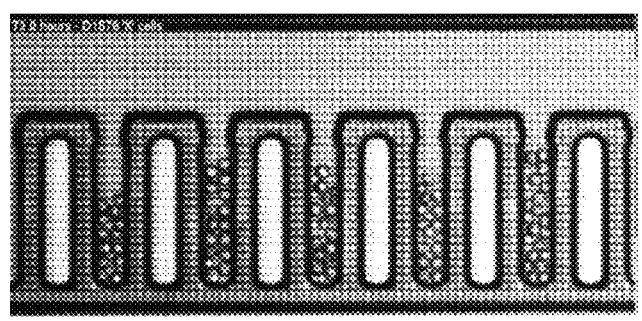

FIGS. 16A-D illustrate experimental results using the tilting apparatus 190 of the above-described system. In FIGS. 16A-D, the microfluidic circuit 120 has been tilted at a very minor degree (1° relative to a Z axis defined by the force of gravity). The small tilt is sufficient to retain cells within the sequestration pens as the cells undergo cell division and expansion. At the 1.50 hour time point, shown in FIG. 16A, there is one cell in each sequestration pen. At the 25-hour time point, shown in FIG. 16B, the cells have undergone cell division and growth, producing two to four cells which remain in the sequestration pen due to the minor tilt of the sequestration pen relative to the force of gravity. As shown in FIGS. 16C and 16D, the cells continue to proliferate through the 49.5 hour and 73 hour time points, but remain within their sequestration pens due to the minor (1°) tilt of the microfluidic device.

FIGS. 17A-D likewise illustrate experimental results using the tilting apparatus 190. As shown, the sequestration pens of the microfluidic device are configured to retain micro-objects, such as cells, when the device is tilted. In FIGS. 17A-D, the microfluidic device has been tilted at a very minor degree (−1° relative to a Z-axis defined by the force of gravity). At the 2.08 hour time point, shown in FIG. 17A, there is only one cell in each sequestration pen. At the 27.17 hour time point, shown in FIG. 17B, there are two to four cells in each sequestration pen, and the tilt causes the cells to be disposed towards the lower left hand corner of the sequestration pens. Due to the combination of the tilt and the shape of the sequestration pens, the cells in the sequestration pens pictured at left are favorably retained in comparison to the cells in the sequestration pens pictured at right. At the 51.25 hour time point, shown in FIG. 17C, the sequestration pens contain even larger numbers of cells due to proliferation, yet the cells remain disposed in the lower left hand corner of the sequestration pens due to the minor tilt. FIG. 17D shows the cells at a more advanced stage of proliferation, with the cells in the sequestration pens pictured at left retained in the left corner of the sequestration pens.

Although specific embodiments and applications of the invention have been described in this specification, these embodiments and applications are exemplary only, and many variations are possible. For example, the use of gravitational force can be replaced with the use of centrifugal force in any of the disclosed embodiments.

The invention claimed is:

1. A microfluidic device comprising an enclosure, wherein said enclosure comprises:
- a flow path configured to contain a flow of a fluidic medium; and
- a microfluidic sequestration pen comprising:
  - an isolation region; and
  - a connection region fluidically connecting said isolation region to said flow path,
- wherein said isolation region includes an opening that interfaces with said connection region and said sequestration pen further comprises an obstruction or a constriction located at the interface between said connection region and the opening of said isolation region,
- wherein said isolation region has a volume sufficient to hold at least one target micro-object, said target micro-object being a mammalian cell, and
- wherein, when said microfluidic device is tilted such that said flow path is located below said sequestration pen, target micro-objects located in said isolation region are retained in said isolation region while target micro-objects located in said connection region settle into said flow path.

2. The microfluidic device of claim 1, wherein said sequestration pen has a boot-like shape.

3. The microfluidic device of claim 1, wherein said sequestration pen has a nautilus-like shape.

4. The microfluidic device of claim 1, wherein the opening of said connection region to said isolation region has a width of less than about 50 microns.

5. The microfluidic device of claim 1, wherein said obstruction or constriction has a width that is less than about 50 microns.

6. The microfluidic device of claim 1, wherein said isolation region comprises a distal end having a volume configured to receive a single target micro-object.

7. The microfluidic device of claim 6, wherein said isolation region or the distal end of said isolation region has a volume of about 10,000 $\mu m^3$ to about 20,000 $\mu m^3$.

8. The microfluidic device of claim 1, wherein said microfluidic sequestration pen comprises a plurality of said isolation regions.

9. The microfluidic device of claim 8, wherein the isolation regions of said plurality have substantially the same volume.

10. The microfluidic device of claim 1, further comprising a plurality of said microfluidic sequestration pens, each comprising a corresponding isolation region and a corresponding connection region fluidically connecting said corresponding isolation region to said flow path.

11. The microfluidic device of claim 1, wherein said flow path is defined by a channel, said channel further comprising a trap formed in a wall of said channel opposite an opening to said sequestration pen, said trap comprising an opening that is approximately equal to or greater than the diameter of said target micro-object.

12. The microfluidic device of claim 11, wherein said trap further comprises a side passage comprising a width that is less than the diameter of said target micro-object.

13. The microfluidic device of claim 11, wherein said microfluidic device comprises a plurality of traps.

14. The microfluidic device of claim 1, further comprising a support structure and a microfluidic structure that together define said enclosure, wherein said support structure and said microfluidic structure are configured to support the generation of an electrokinetic force within at least a portion of said enclosure.

15. The microfluidic device of claim 14, wherein the portion of said enclosure in which said electrokinetic force can be generated includes said sequestration pen.

16. The microfluidic device of claim 14, where said support structure comprises an electrode connected to an array of transistors.

17. The microfluidic device of claim 16, wherein the transistors of said array are phototransistors.

18. The microfluidic device of claim 14, wherein said microfluidic structure comprises walls and a cover, and wherein said cover is transparent and comprises an electrode.

19. The device of claim 1, wherein a surface of said sequestration pen further comprises a functional moiety that specifically binds to said target micro-objects, said functional moiety comprising a polymer, a carbohydrate, an antibody, an extracellular matrix component or derivative thereof, or any combination thereof.

20. A microfluidic device comprising an enclosure, wherein said enclosure comprises:
   a flow path configured to contain a flow of a fluidic medium; and
   a microfluidic sequestration pen comprising an isolation region and a plurality of connection regions, each connection region fluidically connecting said isolation region to said flow path.

21. A method for loading a target micro-object into a microfluidic sequestration pen, the method comprising:
   flowing a fluidic medium containing target micro-objects into a flow path of a microfluidic device, wherein said device comprises a microfluidic sequestration pen fluidically connected to said flow path;
   positioning said microfluidic device into a first loading position such that a first portion of fluidic medium in said flow path is located above an opening of said sequestration pen to said flow path; and
   allowing gravity to act on said target micro-objects for an amount of time sufficient for any target micro-objects located in the first portion of fluidic medium in said flow path to settle into said sequestration pen.

22. The method of claim 21 further comprising slowing or substantially stopping the flow of said fluidic medium through said flow path prior to positioning said microfluidic device into the first loading position.

23. The method of claim 21, wherein positioning said microfluidic device into the first loading position comprises tilting said microfluidic device along an axis of said flow path.

24. The method of claim 21, wherein:
   said sequestration pen comprises an isolation region and a connection region fluidically connecting said isolation region to said flow path, the isolation region and connection region configured such that target micro-objects that settled into said sequestration pen collect in said connection region; and
   said method further comprises:
      optionally repositioning said microfluidic device; and
      moving one or more target micro-objects located in said connection region into said isolation region.

25. The method of claim 24, wherein moving said one or more target micro-objects into said isolation region comprises:
   detecting said one or more target micro-objects located in said connection region;
   selecting a single target micro-object from said one or more target micro-objects;
   moving said selected target micro-object from said connection region into said isolation region; and
   moving any target micro-objects remaining in said connection region back into said flow path.

26. The method of claim 25, wherein said selected target micro-object is moved using electrokinetic force, said electrokinetic force selected from the group consisting of dielectrophoresis (DEP) and optoelectronic tweezers (OET).

27. The method of claim 25, wherein moving any target micro-objects remaining in said connection region back into said flow path comprises:
   positioning said microfluidic device into an unloading position such that the first portion of fluidic medium in said flow path is located beneath the opening of said sequestration pen to said flow path; and
   allowing gravity to act on any target micro-objects remaining in said connection region for an amount of time sufficient for such target micro-objects to settle into the first portion of fluidic medium in said flow path.

28. The method of claim 24, wherein moving said one or more target micro-objects into said isolation region comprises:
   positioning said microfluidic device into a second loading position such that a first portion of said connection region is located above an opening of said isolation region to said connection region; and
   allowing gravity to act on target micro-objects located in the first portion of said connection region, for an amount of time sufficient for any such target micro-objects to settle into said isolation region.

29. The method of claim 28, wherein positioning said microfluidic device into a second loading position comprises:
   tilting said microfluidic device along an axis substantially perpendicular to an axis defined by the opening of said isolation region to said connection region; or
   tilting said microfluidic device along an axis substantially perpendicular to the axis of said flow path.

30. The method of claim 28, further comprising:
   detecting one or more target micro-objects located in said isolation region;
   selecting a single target micro-object from said one or more target micro-objects;
   moving all target micro-objects other than said selected target micro-object from said isolation region back into said connection region; and
   moving any target micro-objects returned to said connection region back into said flow path.

31. The method of claim 30, wherein target micro-objects moved back into said connection region are moved using electrokinetic force, said electrokinetic force selected from the group consisting of dielectrophoresis (DEP) and optoelectronic tweezers (OET).

32. The method of claim 30, wherein moving any target micro-objects returned to said connection region back into said flow path comprises:
   positioning said microfluidic device into an unloading position such that the first portion of fluidic medium in said flow path is located beneath the opening of said sequestration pen to said flow path; and
   allowing gravity to act on any target micro-objects remaining in said connection region for an amount of time sufficient for such target micro-objects to settle into the first portion of said flow path.

33. The method of claim 21, wherein said microfluidic device comprises a plurality of said sequestration pens, and wherein said plurality of sequestration pens are loaded with target micro-objects in parallel.

* * * * *